US010695550B2

(12) United States Patent
Gardner et al.

(10) Patent No.: US 10,695,550 B2
(45) Date of Patent: Jun. 30, 2020

(54) CAPS FOR NEEDLELESS CONNECTORS

(71) Applicant: Excelsior Medical Corporation, San Clemente, CA (US)

(72) Inventors: Christopher E. Gardner, Manalapan, NJ (US); Chirag Sanjay Walawalkar, Jackson, NJ (US); Larry Colquitt, West Henrietta, NY (US); Mark Wilson, Rochester, NY (US); William Anderson, Cary, IL (US); Sofi Enroth, Conshohocken, PA (US)

(73) Assignee: Excelsior Medical Corporation, San Clemente, CA (US)

( * ) Notice: Subject to any disclaimer, the term of this patent is extended or adjusted under 35 U.S.C. 154(b) by 0 days.

(21) Appl. No.: 16/016,960

(22) Filed: Jun. 25, 2018

(65) Prior Publication Data
US 2018/0369562 A1    Dec. 27, 2018

Related U.S. Application Data

(62) Division of application No. 13/476,772, filed on May 21, 2012, now Pat. No. 10,016,587.
(Continued)

(51) Int. Cl.
*A61M 39/20* (2006.01)
*A61M 25/00* (2006.01)
*A61M 39/16* (2006.01)

(52) U.S. Cl.
CPC ......... *A61M 39/20* (2013.01); *A61M 25/0097* (2013.01); *A61M 39/162* (2013.01);
(Continued)

(58) Field of Classification Search
CPC ............... A61M 39/162; A61M 39/20; A61M 2039/0288; A61M 2039/205;
(Continued)

(56) References Cited

U.S. PATENT DOCUMENTS

| 877,946 A | 2/1908 | Overton |
| 1,793,068 A | 2/1931 | Dickinson |

(Continued)

FOREIGN PATENT DOCUMENTS

| CA | 2 148 847 | 12/1995 |
| CA | 2 169 689 | 8/1996 |

(Continued)

OTHER PUBLICATIONS

Australian Examination Report re AU Applicaton No. 2008269133, dated Aug. 27, 2012 (4 pages).
(Continued)

*Primary Examiner* — Kami A Bosworth
(74) *Attorney, Agent, or Firm* — Knobbe Martens Olson & Bear, LLP

(57) ABSTRACT

An antiseptic cap and packaging for use with a connector are provided. The antiseptic cap includes a material containing an antiseptic solution. Upon application of the cap to the connector, the material compresses thereby releasing the antiseptic solution. Packaging of the antiseptic cap typically includes a cap holder and a lid. A user could remove the cap from the cap holder before applying it to a connector. Alternatively, the cap holder may be used to apply the cap to the connector.

16 Claims, 29 Drawing Sheets

Related U.S. Application Data

(60) Provisional application No. 61/519,324, filed on May 20, 2011.

(52) U.S. Cl.
CPC ... *A61M 39/165* (2013.01); *A61M 2025/0018* (2013.01); *A61M 2025/0056* (2013.01)

(58) Field of Classification Search
CPC .. A61M 2025/0056; A61M 2005/3104; A61M 2005/3118; A61M 2005/312; A61M 2005/3121; A61L 2/18; A61L 2202/18; A61L 2202/182; A61L 2202/20; A61L 2202/23; A61L 2202/24; A61B 1/00137; A61B 5/150351; A61B 90/70; A61B 2090/701; B65D 41/16; B65D 41/165; B65D 41/18; B65D 41/185; B65D 41/46; B65D 41/465; B65D 41/48; B65D 41/485
See application file for complete search history.

(56) References Cited

U.S. PATENT DOCUMENTS

| | | |
|---|---|---|
| 2,098,340 A | 11/1937 | Henahan |
| 2,436,297 A | 2/1948 | Guarnaschelli |
| 2,457,052 A | 12/1948 | Le Clair |
| 2,771,644 A | 11/1956 | Martin |
| 2,842,382 A | 7/1958 | Franck |
| 2,968,497 A | 1/1961 | Treleman |
| 3,127,892 A | 4/1964 | Bellamy, Jr. et al. |
| 3,270,743 A | 9/1966 | Gingras |
| 3,301,392 A | 1/1967 | Eddingfield |
| 3,304,047 A | 2/1967 | Martin |
| 3,334,860 A | 8/1967 | Bolton, Jr. |
| 3,411,665 A | 11/1968 | Blum |
| 3,538,950 A | 11/1970 | Porteners |
| 3,604,582 A | 9/1971 | Boudin |
| 3,707,972 A | 1/1973 | Villari et al. |
| 3,729,031 A | 4/1973 | Baldwin |
| 3,882,858 A | 5/1975 | Klemm |
| 3,977,401 A | 8/1976 | Pike |
| 3,987,930 A | 10/1976 | Fuson |
| 4,041,934 A | 8/1977 | Genese |
| 4,066,067 A | 1/1978 | Micheli |
| 4,076,285 A | 2/1978 | Martinez |
| 4,095,810 A | 6/1978 | Kulle |
| 4,121,585 A | 10/1978 | Becker, Jr. |
| 4,133,441 A | 1/1979 | Mittleman et al. |
| 4,143,853 A | 3/1979 | Abramson |
| 4,150,845 A | 4/1979 | Kopacz et al. |
| 4,192,443 A | 3/1980 | McLaren |
| 4,195,632 A | 4/1980 | Parker et al. |
| 4,233,982 A | 11/1980 | Bauer et al. |
| 4,243,035 A | 1/1981 | Barrett |
| 4,245,635 A | 1/1981 | Kontos |
| 4,280,632 A | 7/1981 | Yuhara |
| 4,294,370 A | 10/1981 | Toeppen |
| 4,317,446 A | 3/1982 | Ambrosio et al. |
| 4,324,239 A | 4/1982 | Gordon et al. |
| 4,334,551 A | 6/1982 | Pfister |
| 4,335,756 A | 6/1982 | Sharp et al. |
| 4,340,049 A | 7/1982 | Munsch |
| 4,379,458 A | 4/1983 | Bauer et al. |
| 4,384,589 A | 5/1983 | Morris |
| 4,387,879 A | 6/1983 | Tauschinski |
| 4,397,442 A | 8/1983 | Larkin |
| 4,402,691 A | 9/1983 | Rosenthal et al. |
| 4,417,890 A | 11/1983 | Dennehey et al. |
| 4,427,126 A | 1/1984 | Ostrowsky |
| 4,430,073 A | 2/1984 | Bemis et al. |
| 4,432,764 A | 2/1984 | Lopez |
| 4,432,766 A | 2/1984 | Bellotti et al. |
| 4,436,125 A | 3/1984 | Blenkush |
| 4,439,184 A | 3/1984 | Wheeler |
| 4,440,207 A | 4/1984 | Genatempo et al. |
| 4,444,310 A | 4/1984 | Odell |
| 4,457,749 A | 7/1984 | Bellotti et al. |
| 4,461,368 A | 7/1984 | Plourde |
| 4,480,940 A | 11/1984 | Woodruff |
| 4,507,111 A | 3/1985 | Gordon et al. |
| 4,511,359 A | 4/1985 | Vaillancourt |
| 4,538,836 A | 9/1985 | Kruetten |
| 4,610,469 A | 9/1986 | Wolff-Mooij |
| 4,619,640 A | 10/1986 | Potolsky et al. |
| 4,623,332 A | 11/1986 | Lindmayer et al. |
| 4,624,664 A | 11/1986 | Peluso et al. |
| 4,629,159 A | 12/1986 | Wellenstam |
| 4,660,803 A | 4/1987 | Johnston et al. |
| 4,662,878 A | 5/1987 | Lindmayer |
| 4,666,057 A | 5/1987 | Come et al. |
| 4,666,427 A | 5/1987 | Larsson et al. |
| 4,671,306 A | 6/1987 | Spector |
| 4,700,744 A | 10/1987 | Rutter et al. |
| 4,703,762 A | 11/1987 | Rathbone et al. |
| 4,723,603 A | 2/1988 | Plummer |
| 4,728,075 A | 3/1988 | Paradis |
| 4,728,321 A | 3/1988 | Chen |
| 4,745,950 A | 5/1988 | Mathieu |
| 4,747,502 A | 5/1988 | Luenser |
| 4,752,983 A | 6/1988 | Crieshaber |
| 4,774,964 A | 10/1988 | Bonaldo |
| 4,774,965 A | 10/1988 | Rodriguez et al. |
| 4,778,447 A | 10/1988 | Velde et al. |
| 4,781,702 A | 11/1988 | Herrli |
| 4,799,926 A | 1/1989 | Haber |
| 4,804,015 A | 2/1989 | Albinsson |
| 4,810,241 A | 3/1989 | Rogers |
| 4,811,847 A | 3/1989 | Reif et al. |
| 4,813,933 A | 3/1989 | Turner |
| 4,816,024 A | 3/1989 | Sitar et al. |
| 4,834,271 A | 5/1989 | Litwin |
| 4,862,913 A | 9/1989 | Wildfang |
| 4,883,483 A | 11/1989 | Lindmayer |
| 4,915,687 A | 4/1990 | Sivert |
| 4,917,669 A | 4/1990 | Bonaldo |
| 4,927,019 A | 5/1990 | Haber et al. |
| 4,935,010 A | 6/1990 | Cox et al. |
| 4,950,260 A | 8/1990 | Bonaldo |
| 4,957,637 A | 9/1990 | Cornell |
| D313,277 S | 12/1990 | Haining |
| D314,050 S | 1/1991 | Sone |
| 4,983,161 A | 1/1991 | Dadson et al. |
| 4,989,733 A | 2/1991 | Patry |
| 4,991,629 A | 2/1991 | Ernesto et al. |
| 5,006,114 A | 4/1991 | Rogers et al. |
| 5,021,059 A | 6/1991 | Kensey et al. |
| 5,047,021 A | 9/1991 | Utterberg |
| 5,065,783 A | 11/1991 | Ogle, II |
| 5,070,885 A | 12/1991 | Bonaldo |
| 5,098,385 A | 3/1992 | Walsh |
| 5,108,376 A | 4/1992 | Bonaldo |
| 5,122,123 A | 6/1992 | Vaillancourt |
| 5,139,483 A | 8/1992 | Ryan |
| 5,143,104 A | 9/1992 | Iba et al. |
| 5,147,333 A | 9/1992 | Raines |
| 5,154,703 A | 10/1992 | Bonaldo |
| 5,184,742 A | 2/1993 | DeCaprio et al. |
| 5,190,534 A | 3/1993 | Kendell |
| RE34,223 E | 4/1993 | Bonaldo |
| 5,199,948 A | 4/1993 | McPhee |
| 5,201,725 A | 4/1993 | Kling |
| 5,203,775 A | 4/1993 | Frank et al. |
| 5,205,821 A | 4/1993 | Kruger et al. |
| 5,211,634 A | 5/1993 | Vaillancourt |
| 5,215,537 A | 6/1993 | Lynn et al. |
| 5,242,421 A | 9/1993 | Chan |
| 5,242,425 A | 9/1993 | White et al. |
| 5,246,011 A | 9/1993 | Caillouette |
| 5,251,873 A | 10/1993 | Atkinson et al. |
| D342,134 S | 12/1993 | Mongeon |
| 5,269,771 A | 12/1993 | Thomas et al. |
| 5,281,206 A | 1/1994 | Lopez |
| 5,284,475 A | 2/1994 | Mackal |

(56) References Cited

U.S. PATENT DOCUMENTS

| | | |
|---|---|---|
| 5,295,657 A | 3/1994 | Atkinson |
| 5,301,686 A | 4/1994 | Newman |
| 5,306,243 A | 4/1994 | Bonaldo |
| 5,312,377 A | 5/1994 | Dalton |
| 5,324,270 A | 6/1994 | Kayan et al. |
| 5,330,235 A | 7/1994 | Wagner et al. |
| 5,330,450 A | 7/1994 | Lopez |
| 5,344,414 A | 9/1994 | Lopez et al. |
| 5,352,410 A | 10/1994 | Hansen et al. |
| 5,360,413 A | 11/1994 | Leason et al. |
| 5,370,636 A | 12/1994 | Von Witzleben |
| 5,380,306 A | 1/1995 | Brinon |
| 5,391,150 A | 2/1995 | Richmond |
| 5,402,826 A | 4/1995 | Molnar et al. |
| 5,405,331 A | 4/1995 | Behnke et al. |
| 5,405,333 A | 4/1995 | Richmond |
| 5,411,499 A | 5/1995 | Dudar et al. |
| 5,417,673 A | 5/1995 | Gordon |
| 5,425,465 A | 6/1995 | Healy |
| 5,433,330 A | 7/1995 | Yatsko et al. |
| 5,439,451 A | 8/1995 | Collinson et al. |
| 5,441,487 A | 8/1995 | Vedder |
| 5,445,623 A | 8/1995 | Richmond |
| 5,456,668 A | 10/1995 | Ogle, II |
| 5,456,675 A | 10/1995 | Wolbring et al. |
| 5,464,399 A | 11/1995 | Boettger |
| 5,470,327 A | 11/1995 | Helgren et al. |
| 5,471,706 A | 12/1995 | Wallock et al. |
| 5,474,536 A | 12/1995 | Bonaldo |
| 5,480,393 A | 1/1996 | Bommarito |
| 5,492,147 A | 2/1996 | Challender et al. |
| 5,501,426 A | 3/1996 | Atkinson et al. |
| 5,507,744 A | 4/1996 | Tay et al. |
| 5,514,177 A | 5/1996 | Kurz et al. |
| 5,518,026 A | 5/1996 | Benjey |
| 5,520,665 A | 5/1996 | Fleetwood |
| 5,520,666 A | 5/1996 | Choudhury et al. |
| 5,533,708 A | 7/1996 | Atkinson et al. |
| 5,533,983 A | 7/1996 | Haining |
| 5,535,785 A | 7/1996 | Werge et al. |
| 5,536,258 A | 7/1996 | Folden |
| 5,540,661 A | 7/1996 | Tomisaka et al. |
| 5,549,566 A | 8/1996 | Elias et al. |
| 5,549,651 A | 8/1996 | Lynn |
| 5,552,115 A | 9/1996 | Malchesky |
| 5,552,118 A | 9/1996 | Mayer |
| 5,554,135 A | 9/1996 | Menyhay |
| 5,555,908 A | 9/1996 | Edwards et al. |
| 5,569,235 A | 10/1996 | Ross et al. |
| 5,573,516 A | 11/1996 | Tyner |
| 5,575,769 A | 11/1996 | Vaillancourt |
| 5,578,059 A | 11/1996 | Patzer |
| 5,580,530 A | 12/1996 | Kowatsch et al. |
| 5,584,819 A | 12/1996 | Kopfer |
| 5,591,137 A | 1/1997 | Stevens |
| 5,591,143 A | 1/1997 | Trombley, III et al. |
| 5,597,536 A | 1/1997 | Mayer |
| 5,616,130 A | 4/1997 | Mayer |
| 5,620,088 A | 4/1997 | Martin et al. |
| 5,624,402 A | 4/1997 | Imbert |
| RE35,539 E | 6/1997 | Bonaldo |
| 5,645,538 A | 7/1997 | Richmond |
| 5,674,206 A | 10/1997 | Allton et al. |
| 5,676,346 A | 10/1997 | Leinsing |
| 5,685,868 A | 11/1997 | Lundquist |
| 5,688,253 A | 11/1997 | Paradis |
| 5,694,978 A | 12/1997 | Heilmann et al. |
| 5,699,821 A | 12/1997 | Paradis |
| 5,700,248 A | 12/1997 | Lopez |
| 5,702,017 A | 12/1997 | Goncalves |
| 5,722,537 A | 3/1998 | Sigler |
| 5,735,826 A | 4/1998 | Richmond |
| 5,738,144 A | 4/1998 | Rogers |
| 5,749,861 A | 5/1998 | Guala et al. |
| 5,776,116 A | 7/1998 | Lopez |
| 5,782,816 A | 7/1998 | Werschmidt et al. |
| 5,785,693 A | 7/1998 | Haining |
| 5,792,120 A | 8/1998 | Menyhay |
| 5,806,831 A | 9/1998 | Paradis |
| 5,810,792 A | 9/1998 | Fangrow, Jr. et al. |
| 5,814,024 A | 9/1998 | Thompson et al. |
| 5,820,601 A | 10/1998 | Mayer |
| 5,820,604 A | 10/1998 | Fox et al. |
| 5,827,244 A | 10/1998 | Boettger |
| 5,839,715 A | 11/1998 | Leinsing |
| 5,848,994 A | 12/1998 | Richmond |
| 5,941,857 A | 8/1999 | Nguyen et al. |
| 5,947,954 A | 9/1999 | Bonaldo |
| 5,951,519 A * | 9/1999 | Utterberg ............... A61M 39/20 604/167.01 |
| 5,954,957 A | 9/1999 | Chin-Loy et al. |
| 5,971,972 A | 10/1999 | Rosenbaum |
| D416,086 S | 11/1999 | Parris et al. |
| 5,989,229 A | 11/1999 | Chiappetta |
| 6,029,946 A | 2/2000 | Doyle |
| 6,036,171 A | 3/2000 | Weinheimer et al. |
| 6,041,805 A | 3/2000 | Gydesen et al. |
| 6,045,539 A | 4/2000 | Menyhay |
| 6,050,978 A | 4/2000 | Orr et al. |
| 6,063,062 A | 5/2000 | Paradis |
| 6,068,011 A | 5/2000 | Paradis |
| 6,068,475 A | 5/2000 | Stoyka, Jr. et al. |
| 6,068,617 A | 5/2000 | Richmond |
| 6,079,432 A | 6/2000 | Paradis |
| 6,106,502 A | 8/2000 | Richmond |
| 6,113,068 A | 9/2000 | Ryan |
| 6,116,468 A | 9/2000 | Nilson |
| 6,117,114 A | 9/2000 | Paradis |
| 6,126,640 A | 10/2000 | Tucker |
| 6,142,446 A | 11/2000 | Leinsing |
| 6,152,913 A | 11/2000 | Feith et al. |
| 6,158,614 A | 12/2000 | Haines et al. |
| 6,170,522 B1 | 1/2001 | Tanida |
| 6,171,287 B1 * | 1/2001 | Lynn ..................... A61M 39/02 251/149 |
| 6,179,141 B1 | 1/2001 | Nakamura |
| 6,202,870 B1 | 3/2001 | Pearce |
| 6,206,134 B1 | 3/2001 | Stark et al. |
| 6,206,860 B1 | 3/2001 | Richmond |
| 6,227,391 B1 | 5/2001 | King |
| 6,242,393 B1 | 6/2001 | Ishida et al. |
| 6,245,048 B1 | 6/2001 | Fangrow, Jr. et al. |
| 6,245,056 B1 | 6/2001 | Walker et al. |
| 6,248,380 B1 | 6/2001 | Kocher et al. |
| 6,250,315 B1 | 6/2001 | Ernster |
| 6,299,132 B1 | 10/2001 | Weinheimer et al. |
| 6,315,761 B1 | 11/2001 | Shcherbina et al. |
| 6,394,983 B1 | 5/2002 | Mayoral et al. |
| 6,402,207 B1 | 6/2002 | Segal et al. |
| 6,428,520 B1 | 8/2002 | Lopez |
| 6,431,219 B1 | 8/2002 | Redler et al. |
| 6,499,719 B1 | 12/2002 | Clancy et al. |
| 6,508,792 B2 | 1/2003 | Szames et al. |
| 6,541,802 B2 | 4/2003 | Doyle |
| 6,543,745 B1 | 4/2003 | Enerson |
| 6,550,493 B2 | 4/2003 | Williamson et al. |
| 6,555,504 B1 | 4/2003 | Ayai et al. |
| 6,581,906 B2 | 6/2003 | Pott et al. |
| 6,585,691 B1 | 7/2003 | Vitello |
| 6,595,964 B2 | 7/2003 | Finley et al. |
| 6,595,981 B2 | 7/2003 | Huet |
| 6,609,696 B2 | 8/2003 | Enerson |
| 6,666,852 B2 | 12/2003 | Niedospial, Jr. |
| 6,679,395 B1 | 1/2004 | Pfefferkorn et al. |
| 6,679,870 B1 | 1/2004 | Finch et al. |
| 6,681,803 B2 | 1/2004 | Taneya et al. |
| 6,685,694 B2 | 2/2004 | Finch et al. |
| 6,692,468 B1 | 2/2004 | Waldenburg |
| 6,695,817 B1 | 2/2004 | Fangrow |
| 6,716,396 B1 | 4/2004 | Anderson |
| 6,745,998 B2 | 6/2004 | Doyle |
| 6,827,766 B2 | 12/2004 | Carnes et al. |
| 6,840,501 B2 | 1/2005 | Doyle |
| 6,875,205 B2 | 4/2005 | Leinsing |

(56) References Cited

U.S. PATENT DOCUMENTS

| | | |
|---|---|---|
| 6,899,315 B2 | 5/2005 | Mailville et al. |
| 6,911,025 B2 | 6/2005 | Miyahar |
| 6,943,035 B1 | 9/2005 | Davies et al. |
| 6,955,669 B2 | 10/2005 | Curutcharry |
| 6,964,406 B2 | 11/2005 | Doyle |
| 7,004,934 B2 | 2/2006 | Vaillancourt |
| 7,037,302 B2 | 5/2006 | Vaillancourt |
| 7,040,598 B2 | 5/2006 | Raybuck |
| 7,044,441 B2 | 5/2006 | Doyle |
| 7,056,308 B2 | 6/2006 | Utterberg |
| 7,083,605 B2 | 8/2006 | Miyahara |
| 7,100,891 B2 | 9/2006 | Doyle |
| 7,125,396 B2 | 10/2006 | Leinsing et al. |
| 7,140,592 B2 | 11/2006 | Phillips |
| 7,160,272 B1 | 1/2007 | Eyal et al. |
| 7,182,313 B2 | 2/2007 | Doyle |
| 7,198,611 B2 | 4/2007 | Connell et al. |
| 7,244,249 B2 | 7/2007 | Leinsing et al. |
| 7,282,186 B2 | 10/2007 | Lake, Jr. et al. |
| 7,306,197 B2 | 12/2007 | Parrino et al. |
| 7,306,198 B2 | 12/2007 | Doyle |
| 7,306,566 B2 | 12/2007 | Raybuck |
| 7,309,326 B2 | 12/2007 | Fangrow, Jr. |
| 7,347,458 B2 | 3/2008 | Rome et al. |
| 7,350,764 B2 | 4/2008 | Raybuck |
| 7,361,164 B2 | 4/2008 | Simpson et al. |
| 7,431,712 B2 | 10/2008 | Kim |
| 7,452,349 B2 | 11/2008 | Miyahar |
| 7,497,484 B2 | 3/2009 | Ziman |
| 7,516,846 B2 | 4/2009 | Hansen |
| 7,588,563 B2 | 9/2009 | Guala |
| 7,614,426 B2 | 11/2009 | Kitani et al. |
| 7,635,344 B2 | 12/2009 | Tennican et al. |
| D607,325 S | 1/2010 | Rogers et al. |
| 7,645,274 B2 | 1/2010 | Whitley |
| 7,651,481 B2 | 1/2010 | Raybuck |
| 7,666,170 B2 | 2/2010 | Guala |
| 7,708,714 B2 | 5/2010 | Connell et al. |
| 7,731,678 B2 | 6/2010 | Tennican et al. |
| 7,731,679 B2 | 6/2010 | Tennican et al. |
| 7,749,189 B2 | 7/2010 | Tennican et al. |
| 7,753,891 B2 | 7/2010 | Tennican et al. |
| 7,758,566 B2 | 7/2010 | Simpson et al. |
| 7,763,006 B2 | 7/2010 | Tennican |
| 7,766,182 B2 | 8/2010 | Trent et al. |
| 7,766,897 B2 | 8/2010 | Ramsey et al. |
| 7,776,011 B2 | 8/2010 | Tennican et al. |
| 7,780,794 B2 | 8/2010 | Rogers et al. |
| 7,794,675 B2 | 9/2010 | Lynn |
| 7,799,010 B2 | 9/2010 | Tennican |
| 7,803,139 B2 | 9/2010 | Fangrow, Jr. |
| 7,803,140 B2 | 9/2010 | Fangrow, Jr. |
| 7,815,614 B2 | 10/2010 | Fangrow, Jr. |
| 7,857,793 B2 | 12/2010 | Raulerson et al. |
| 7,922,701 B2 | 4/2011 | Buchman |
| 7,959,026 B2 | 6/2011 | Bertani |
| 7,985,302 B2 | 7/2011 | Rogers et al. |
| 7,993,309 B2 | 8/2011 | Schweikert |
| 7,998,134 B2 | 8/2011 | Fangrow et al. |
| 8,065,773 B2 | 11/2011 | Vaillancourt et al. |
| 8,066,670 B2 | 11/2011 | Cluff et al. |
| 8,069,523 B2 | 12/2011 | Vaillancourt et al. |
| 8,113,837 B2 | 2/2012 | Zegarelli |
| 8,162,899 B2 | 4/2012 | Tennican |
| 8,167,847 B2 | 5/2012 | Anderson et al. |
| 8,172,825 B2 | 5/2012 | Solomon et al. |
| 8,177,772 B2 | 5/2012 | Christensen et al. |
| 8,206,514 B2 | 6/2012 | Rogers et al. |
| 8,231,587 B2 | 7/2012 | Solomon et al. |
| 8,231,602 B2 | 7/2012 | Anderson et al. |
| 8,262,628 B2 | 9/2012 | Fangrow, Jr. |
| 8,262,643 B2 | 9/2012 | Tennican |
| 8,273,303 B2 | 9/2012 | Ferlic et al. |
| 8,281,824 B2 | 10/2012 | Molema et al. |
| 8,328,767 B2 | 12/2012 | Solomon et al. |
| 8,336,152 B2 | 12/2012 | Kerr et al. |
| 8,343,112 B2 | 1/2013 | Solomon et al. |
| 8,361,408 B2 | 1/2013 | Lynn |
| 8,372,045 B2 | 2/2013 | Needle et al. |
| 8,377,040 B2 | 2/2013 | Burkholz et al. |
| 8,419,713 B1 | 4/2013 | Solomon et al. |
| 8,480,968 B2 | 7/2013 | Lynn |
| 8,523,830 B2 | 9/2013 | Solomon et al. |
| 8,523,831 B2 | 9/2013 | Solomon et al. |
| 8,533,887 B2 | 9/2013 | Hirst |
| 8,545,479 B2 | 10/2013 | Kitani et al. |
| 8,641,681 B2 | 2/2014 | Solomon et al. |
| 8,647,308 B2 | 2/2014 | Solomon et al. |
| 8,647,326 B2 | 2/2014 | Solomon et al. |
| 8,671,496 B2 | 3/2014 | Kerr et al. |
| 8,740,864 B2 | 6/2014 | Hoang et al. |
| 8,777,504 B2 | 7/2014 | Shaw et al. |
| 8,845,593 B2 | 9/2014 | Anderson et al. |
| 8,910,919 B2 | 12/2014 | Bonnal et al. |
| 8,968,268 B2 | 3/2015 | Anderson et al. |
| 9,072,296 B2 | 7/2015 | Mills et al. |
| 9,078,992 B2 | 7/2015 | Ziebol et al. |
| 9,095,667 B2 | 8/2015 | Von Schuckmann |
| 9,114,915 B2 | 8/2015 | Solomon et al. |
| 9,125,600 B2 | 9/2015 | Steube et al. |
| 9,149,624 B2 | 10/2015 | Lewis |
| 9,180,252 B2 | 11/2015 | Gelblum et al. |
| 9,192,449 B2 | 11/2015 | Kerr et al. |
| 9,216,440 B2 | 12/2015 | Ma et al. |
| 9,242,084 B2 | 1/2016 | Solomon et al. |
| 9,259,284 B2 | 2/2016 | Rogers et al. |
| 9,259,535 B2 | 2/2016 | Anderson et al. |
| 9,283,367 B2 | 3/2016 | Hoang et al. |
| 9,283,368 B2 | 3/2016 | Hoang et al. |
| 9,283,369 B2 | 3/2016 | Ma et al. |
| 9,289,588 B2 | 3/2016 | Chen |
| 9,302,049 B2 | 4/2016 | Tekeste |
| 9,320,858 B2 | 4/2016 | Grimm et al. |
| 9,320,859 B2 | 4/2016 | Grimm et al. |
| 9,320,860 B2 | 4/2016 | Grimm et al. |
| 9,352,140 B2 | 5/2016 | Kerr et al. |
| 9,352,141 B2 | 5/2016 | Wong |
| 9,399,125 B2 | 7/2016 | Burkholz |
| 9,408,971 B2 | 8/2016 | Carlyon |
| 9,527,660 B2 | 12/2016 | Tennican |
| 9,592,375 B2 | 3/2017 | Tennican |
| 9,700,676 B2 | 7/2017 | Anderson et al. |
| 9,700,677 B2 | 7/2017 | Anderson et al. |
| 9,700,710 B2 | 7/2017 | Anderson et al. |
| 9,707,348 B2 | 7/2017 | Anderson et al. |
| 9,707,349 B2 | 7/2017 | Anderson et al. |
| 9,707,350 B2 | 7/2017 | Anderson et al. |
| 9,809,355 B2 | 11/2017 | Solomon et al. |
| 9,867,975 B2 | 1/2018 | Gardner et al. |
| 9,933,094 B2 | 4/2018 | Fangrow |
| 10,016,587 B2 | 7/2018 | Gardner et al. |
| 10,046,156 B2 | 8/2018 | Gardner |
| 10,166,381 B2 | 1/2019 | Gardner et al. |
| 2002/0148514 A1 | 10/2002 | Taneya et al. |
| 2002/0193752 A1 | 12/2002 | Lynn |
| 2003/0062376 A1 | 4/2003 | Sears et al. |
| 2003/0153865 A1 | 8/2003 | Connell et al. |
| 2003/0208165 A1 | 11/2003 | Christensen et al. |
| 2004/0034042 A1 | 2/2004 | Tsuji et al. |
| 2004/0048542 A1 | 3/2004 | Thomascheisky et al. |
| 2004/0215148 A1 | 10/2004 | Hwang et al. |
| 2004/0258560 A1 | 12/2004 | Lake, Jr. et al. |
| 2005/0013836 A1 | 1/2005 | Raad |
| 2005/0015075 A1 | 1/2005 | Wright et al. |
| 2005/0065479 A1 | 3/2005 | Schiller et al. |
| 2005/0124942 A1 | 6/2005 | Richmond |
| 2005/0124970 A1 | 6/2005 | Kunin et al. |
| 2005/0147524 A1 | 7/2005 | Bousquet |
| 2005/0148930 A1 | 7/2005 | Hseih et al. |
| 2005/0203460 A1 | 9/2005 | Kim |
| 2005/0214185 A1 | 9/2005 | Castaneda |
| 2005/0228362 A1 | 10/2005 | Vaillancourt |
| 2006/0030827 A1 | 2/2006 | Raulerson et al. |
| 2006/0058734 A1 | 3/2006 | Phillips |

(56) References Cited

U.S. PATENT DOCUMENTS

| | | |
|---|---|---|
| 2006/0129109 A1 | 6/2006 | Shaw et al. |
| 2006/0142730 A1 | 6/2006 | Proulx et al. |
| 2006/0157984 A1* | 7/2006 | Rome ............ A61M 39/105 |
| | | 285/390 |
| 2006/0161115 A1 | 7/2006 | Fangrow |
| 2006/0195117 A1* | 8/2006 | Rucker ............ A61B 1/00137 |
| | | 606/108 |
| 2006/0202146 A1 | 9/2006 | Doyle |
| 2006/0253084 A1 | 11/2006 | Nordgren |
| 2006/0261076 A1 | 11/2006 | Anderson |
| 2007/0088292 A1 | 4/2007 | Fangrow |
| 2007/0088293 A1 | 4/2007 | Fangrow |
| 2007/0088294 A1 | 4/2007 | Fangrow |
| 2007/0112333 A1 | 5/2007 | Hoang et al. |
| 2007/0167910 A1 | 7/2007 | Tennican et al. |
| 2007/0179453 A1 | 8/2007 | Lim et al. |
| 2007/0187353 A1 | 8/2007 | Fox et al. |
| 2007/0249996 A1 | 10/2007 | Tennican et al. |
| 2007/0265578 A1 | 11/2007 | Tennican et al. |
| 2007/0282280 A1 | 12/2007 | Tennican |
| 2007/0287989 A1 | 12/2007 | Crawford et al. |
| 2008/0019889 A1 | 1/2008 | Rogers et al. |
| 2008/0027399 A1 | 1/2008 | Harding et al. |
| 2008/0033371 A1 | 2/2008 | Updegraff et al. |
| 2008/0039803 A1 | 2/2008 | Lynn |
| 2008/0058733 A1 | 3/2008 | Vogt et al. |
| 2008/0086091 A1 | 4/2008 | Anderson et al. |
| 2008/0093245 A1 | 4/2008 | Periasamy et al. |
| 2008/0095680 A1 | 4/2008 | Steffens et al. |
| 2008/0097315 A1 | 4/2008 | Miner et al. |
| 2008/0103485 A1 | 5/2008 | Kruger |
| 2008/0287920 A1 | 5/2008 | Fangrow et al. |
| 2008/0128646 A1 | 6/2008 | Clawson |
| 2008/0132880 A1 | 6/2008 | Buchman |
| 2008/0147047 A1 | 6/2008 | Davis et al. |
| 2008/0177250 A1 | 7/2008 | Howlett et al. |
| 2008/0190485 A1 | 8/2008 | Guala |
| 2008/0235888 A1 | 10/2008 | Vaillancourt et al. |
| 2009/0008393 A1 | 1/2009 | Howlett et al. |
| 2009/0012426 A1 | 1/2009 | Tennican |
| 2009/0062766 A1 | 3/2009 | Howlett et al. |
| 2009/0093757 A1 | 4/2009 | Tennican |
| 2009/0099529 A1 | 4/2009 | Anderson et al. |
| 2009/0137969 A1 | 5/2009 | Colantonio et al. |
| 2009/0205151 A1 | 8/2009 | Fisher et al. |
| 2009/0205656 A1 | 8/2009 | Nishibayashi et al. |
| 2009/0259194 A1 | 10/2009 | Pinedjian et al. |
| 2009/0270832 A1 | 10/2009 | Vancaillie et al. |
| 2010/0003067 A1 | 1/2010 | Shaw et al. |
| 2010/0004510 A1* | 1/2010 | Kuroshima ............ A61B 1/012 |
| | | 600/158 |
| 2010/0047123 A1 | 2/2010 | Solomon et al. |
| 2010/0049170 A1 | 2/2010 | Solomon et al. |
| 2010/0050351 A1 | 3/2010 | Colantonio et al. |
| 2010/0059474 A1 | 3/2010 | Brandenburger et al. |
| 2010/0064456 A1 | 3/2010 | Ferlic |
| 2010/0152670 A1 | 6/2010 | Low |
| 2010/0160894 A1 | 6/2010 | Julian et al. |
| 2010/0172794 A1 | 7/2010 | Ferlic et al. |
| 2010/0242993 A1 | 9/2010 | Hoang et al. |
| 2010/0253070 A1 | 10/2010 | Cheon et al. |
| 2010/0292673 A1* | 11/2010 | Korogi ............ A61M 39/165 |
| | | 604/533 |
| 2010/0306938 A1 | 12/2010 | Rogers et al. |
| 2011/0030726 A1 | 2/2011 | Vaillancourt et al. |
| 2011/0044850 A1 | 2/2011 | Solomon et al. |
| 2011/0046564 A1 | 2/2011 | Zhong |
| 2011/0046603 A1 | 2/2011 | Felsovalyi et al. |
| 2011/0062703 A1 | 3/2011 | Lopez |
| 2011/0062703 A1 | 3/2011 | Shaw et al. |
| 2011/0082431 A1 | 4/2011 | Burgess et al. |
| 2011/0175347 A1 | 7/2011 | Okiyama |
| 2011/0217212 A1 | 9/2011 | Solomon et al. |
| 2011/0232020 A1 | 9/2011 | Rogers et al. |
| 2011/0265825 A1 | 11/2011 | Rogers et al. |
| 2011/0277788 A1 | 11/2011 | Rogers et al. |
| 2011/0290799 A1 | 12/2011 | Anderson et al. |
| 2011/0311602 A1 | 12/2011 | Mills et al. |
| 2011/0314619 A1 | 12/2011 | Schweikert |
| 2012/0031904 A1 | 2/2012 | Kuhn et al. |
| 2012/0039764 A1 | 2/2012 | Solomon et al. |
| 2012/0157965 A1 | 6/2012 | Wotton et al. |
| 2012/0195807 A1 | 8/2012 | Ferlic |
| 2012/0216359 A1 | 8/2012 | Rogers et al. |
| 2012/0216360 A1 | 8/2012 | Rogers et al. |
| 2012/0283693 A1 | 11/2012 | Anderson et al. |
| 2012/0283696 A1 | 11/2012 | Cronenberg et al. |
| 2012/0296284 A1 | 11/2012 | Anderson et al. |
| 2012/0302970 A1 | 11/2012 | Tennican |
| 2012/0302997 A1 | 11/2012 | Gardner et al. |
| 2013/0030414 A1 | 1/2013 | Gardner et al. |
| 2013/0035667 A1 | 2/2013 | Anderson et al. |
| 2013/0053751 A1 | 2/2013 | Holtham |
| 2013/0072908 A1 | 3/2013 | Solomon et al. |
| 2013/0085313 A1 | 4/2013 | Fowler et al. |
| 2013/0098398 A1 | 4/2013 | Kerr et al. |
| 2013/0098938 A1 | 4/2013 | Efthimiadis |
| 2013/0123754 A1 | 5/2013 | Solomon et al. |
| 2013/0171030 A1 | 7/2013 | Ferlic et al. |
| 2013/0183635 A1 | 7/2013 | Wilhoit |
| 2013/0274686 A1 | 10/2013 | Ziebol et al. |
| 2014/0052074 A1 | 2/2014 | Tekeste |
| 2014/0101876 A1 | 4/2014 | Rogers et al. |
| 2014/0227144 A1 | 8/2014 | Liu et al. |
| 2014/0228809 A1 | 8/2014 | Wong |
| 2015/0018774 A1 | 1/2015 | Anderson et al. |
| 2015/0165127 A1 | 6/2015 | Haefele et al. |
| 2015/0217106 A1 | 8/2015 | Banik et al. |
| 2015/0237854 A1 | 8/2015 | Mills et al. |
| 2015/0258324 A1 | 9/2015 | Chida et al. |
| 2015/0314119 A1 | 11/2015 | Anderson et al. |
| 2015/0314120 A1 | 11/2015 | Gardner et al. |
| 2015/0374968 A1 | 12/2015 | Solomon et al. |
| 2016/0001058 A1 | 1/2016 | Ziebol et al. |
| 2016/0015931 A1 | 1/2016 | Ryan et al. |
| 2016/0015959 A1 | 1/2016 | Solomon et al. |
| 2016/0045629 A1 | 2/2016 | Gardner et al. |
| 2016/0067365 A1 | 3/2016 | Ma et al. |
| 2016/0067471 A1 | 3/2016 | Ingram et al. |
| 2016/0088995 A1 | 3/2016 | Ueda et al. |
| 2016/0089530 A1 | 3/2016 | Sathe |
| 2016/0101276 A1 | 4/2016 | Tekeste |
| 2016/0106969 A1 | 4/2016 | Neftel |
| 2016/0121097 A1 | 5/2016 | Steele |
| 2016/0144118 A1 | 5/2016 | Solomon et al. |
| 2016/0158520 A1 | 6/2016 | Ma et al. |
| 2016/0158521 A1 | 6/2016 | Hoang et al. |
| 2016/0158522 A1 | 6/2016 | Hoang et al. |
| 2016/0184527 A1 | 6/2016 | Tekeste |
| 2016/0213912 A1 | 7/2016 | Daneluzzi |
| 2016/0250420 A1 | 9/2016 | Maritan et al. |
| 2017/0143447 A1 | 5/2017 | Rogers et al. |
| 2017/0239443 A1 | 8/2017 | Abitabilo et al. |
| 2017/0361023 A1 | 12/2017 | Anderson et al. |
| 2019/0038888 A1 | 2/2019 | Gardner |
| 2019/0111245 A1 | 4/2019 | Gardner et al. |
| 2019/0282795 A1 | 9/2019 | Fangrow |

FOREIGN PATENT DOCUMENTS

| | | |
|---|---|---|
| CA | 2 583 601 | 4/2006 |
| CA | 2 626 864 | 5/2007 |
| CA | 2 651 192 | 11/2007 |
| CA | 2 615 146 | 6/2008 |
| CN | 2402327 Y | 10/2000 |
| CN | 2815392 Y | 9/2006 |
| CN | 201150420 Y | 11/2008 |
| CN | 201519335 U | 7/2010 |
| DE | 89 06 628 U1 | 9/1989 |
| DE | 29617133 | 1/1997 |
| EP | 0 108 785 | 5/1984 |
| EP | 0 227 219 | 7/1987 |
| EP | 0 245 872 | 11/1987 |
| EP | 0 639 385 | 2/1995 |

(56) References Cited

FOREIGN PATENT DOCUMENTS

| | | |
|---|---|---|
| EP | 0 769 265 | 4/1997 |
| EP | 1 061 000 | 10/2000 |
| EP | 1 331 020 | 7/2003 |
| EP | 1 977 714 | 10/2008 |
| EP | 2 444 117 | 4/2012 |
| EP | 2 606 930 | 6/2013 |
| FR | 2 493 149 A | 5/1982 |
| FR | 2 782 910 | 3/2000 |
| GB | 123221 | 2/1919 |
| GB | 2 296 182 | 6/1996 |
| GB | 2 333 097 | 7/1999 |
| GB | 2 387 772 | 10/2003 |
| JP | 57-131462 U | 8/1982 |
| JP | 04-99950 | 2/1992 |
| JP | 09-216661 A | 8/1997 |
| JP | 2000157630 A | 6/2000 |
| JP | 2002-234567 A | 8/2002 |
| JP | 2002-291906 | 10/2002 |
| JP | 2006-182663 A | 7/2006 |
| JP | 2014-117461 | 6/2014 |
| RU | 2 246 321 C1 | 2/2005 |
| WO | WO 1983/03975 | 11/1983 |
| WO | WO 1985/05040 | 11/1985 |
| WO | WO 1998/12125 | 3/1998 |
| WO | WO 2004/035129 | 4/2004 |
| WO | WO 2004/112846 | 12/2004 |
| WO | WO 2006/007690 | 1/2006 |
| WO | WO 2006/044236 | 4/2006 |
| WO | WO 2007/008511 | 1/2007 |
| WO | WO 2007/056773 | 5/2007 |
| WO | WO 2007/137056 | 11/2007 |
| WO | WO 2008/042285 | 4/2008 |
| WO | WO 2008/086631 | 7/2008 |
| WO | WO 2008/089196 | 7/2008 |
| WO | WO 2008/100950 | 8/2008 |
| WO | WO 2008/140807 | 11/2008 |
| WO | WO 2009/002474 | 12/2008 |
| WO | WO 2009/117135 | 9/2009 |
| WO | WO 2009/123709 | 10/2009 |
| WO | WO 2009/136957 | 11/2009 |
| WO | WO 2009/153224 | 12/2009 |
| WO | WO 2010/002757 | 1/2010 |
| WO | WO 2010/002808 | 1/2010 |
| WO | WO 2010/034470 | 4/2010 |
| WO | WO 2010/039171 | 4/2010 |
| WO | WO 2011/028722 | 3/2011 |
| WO | WO 2011/053924 | 5/2011 |
| WO | WO 2011/119021 | 9/2011 |
| WO | WO 2012/162006 | 11/2012 |
| WO | WO 2012/184716 | 12/2013 |
| WO | WO 2013/192574 | 12/2013 |
| WO | WO 2014/140949 | 9/2014 |
| WO | WO 2015/119940 | 8/2015 |
| WO | WO 2017/015047 | 1/2017 |
| WO | WO 2018/009653 | 1/2018 |
| WO | WO 2018/071717 | 4/2018 |
| WO | WO 2018/237090 | 12/2018 |
| WO | WO 2019/178560 | 9/2019 |

OTHER PUBLICATIONS

Australian Examination Report (No. 2) re AU Applicaton No. 2008269133, dated Jan. 9, 2013 (3 pages).
Australian Examination Report (No. 3) re AU Applicaton No. 2008269133, dated May 1, 2013 (3 pages).
Australian Examination Report (Notice of Acceptance) re AU Applicaton No. 2008269133, dated Nov. 14, 2013 (2 pages).
Australian Examination Report re AU Applicaton No. 2012258435, dated Apr. 18, 2013 (4 pages).
Australian Examination Report re AU Applicaton No. 2013100345, dated Apr. 18, 2013 (4 pages).
Baxter Minicap: Photographs of the Baxter Minicap (Sep. 1, 1998) (4 pages).
Baxter, "Peritoneal Dialysis Patient Connectology," Product Descriptions in 1 page, downloaded Jul. 1, 2011.
Canadian Examination Report, re CA Application No. 2,692,157, dated Apr. 27, 2011 (2 pages).
Canadian Examination Report, re CA Application No. 2,692,157, dated Jun. 6, 2011 (2 pages).
Canadian Examination Report, re CA Application No. 2,692,157, dated Jan. 23, 2013 (4 pages).
Canadian Notice of Allowance, re CA Application No. 2,692,157, dated Oct. 2, 2013 (4 pages).
Catheter Connections, "Introducing DualCap," Product Brochure in 1 page, Copyright 2011.
Chinese Office Action, re CN Application No. 200880103854.5, dated Aug. 3, 2011 (5 pages).
Chinese Second Office Action, re CN Application No. 200880103854.5, dated Apr. 16, 2012 (4 pages).
Chinese Third Office Action, re CN Application No. 200880103854.5, dated Nov. 1, 2012 (4 pages).
Chinese Office Action, re CN Application No. 201310087320.0, dated May 4, 2014 (20 pages).
Colombian Office Action, re CO Application No. 10.000.937, dated Oct. 2012 (9 pages).
Conical Fittings: International Standard, "Conical fittings with 6% (Luer) Taper for Syringes, Needles and certain Other Medical Equipment—Part 2: Lock Fittings", Ref. No. ISO 594-2:1998. International Organization for Standardization (Sep. 1, 1998) 2nd ed. (16 pages).
Devine, redacted version of letter from David A. Divine, Esq. of Lee & Hayes, dated May 16, 2011 (3 pages).
Devine, redacted version of letter from David A. Divine, Esq. of Lee & Hayes, dated May 27, 2011 (3 pages).
Hospira, "You Work in Neverland," Lifeshield Product Brochure in 2 pages, Published 2009.
Hyprotek, "Port Protek," Product Brochure in 1 page, downloaded Sep. 19, 2011 from http://www.hyprotek.com/products.html.
International Search Report re PCT/US08/07797, dated Sep. 11, 2008 (3 pages).
International Written Opinion re PCT/US08/07797, dated Sep. 11, 2008 (3 pages).
International Preliminary Report on Patentability re PCT/US08/07797, dated Dec. 22, 2009 (4 pages).
International Search Report re PCT/US2012/037772, dated Oct. 26, 2012 (5 pages).
International Written Opinion re PCT/US2012/037772, dated Oct. 26, 2012 (5 pages).
International Preliminary Report on Patentability re PCT/US2012/037772, dated Nov. 26, 2012 (7 pages).
International Search Report re PCT/US2012/038880, dated Nov. 19, 2012 (5 pages).
International Written Opinion re PCT/US2012/038880, dated Nov. 19, 2012 (8 pages).
International Preliminary Report on Patentability re PCT/US2012/038880, dated Nov. 20, 2013 (1 pages).
International Search Report re PCT/US2012/062078, dated Feb. 14, 2013 (3 pages).
International Written Opinion re PCT/US2012/062078, dated Feb. 14, 2013 (3 pages).
International Preliminary Report on Patentability re PCT/US2012/062078, dated May 6, 2014 (3 pages).
International Search Report re PCT/US2014/23140, dated Jul. 28, 2014 (3 pages).
International Written Opinion re PCT/US2014/23140, dated Jul. 28, 2014 (6 pages).
Japanese Office Action, re JP Application No. 2013-162527, dated Nov. 21, 2014 (2 pages).
Menyhay et al., "Disinfection of Needleless Catheter Connectors and Access Ports with Alcohol May Not Prevent Microbial Entry: The Promise of a Novel Antiseptic-Barrier Cap" Infection Control Hospital and Epidemiology, vol. 27, No. 1 (Jan. 2006) (5 pages).
Mexican Office Action (Memo [2nd] concerning OA) re MX Application No. MX/a/2010/000171, dated Oct. 22, 2013 (1 pages).
Mexican Office Action (Memo concerning OA) re MX Application No. MX/a/2010/000171, dated Feb. 25, 2013 (2 pages).

(56) References Cited

OTHER PUBLICATIONS

New Zealand Examination Report and Notice of Acceptance, re NZ Application No. 582395, dated Jun. 13, 2011 (2 pages).
New Zealand Examination Report, re NZ Application No. 582395, dated Nov. 8, 2012 (2 pages).
New Zealand Examination Report and Notice of Acceptance, re NZ Application No. 582395, dated Dec. 5, 2012 (1 page).
New Zealand Examination Report re NZ Application No. 603404, dated Nov. 8, 2012 (2 pages).
New Zealand Examination Report (1st) re NZ Application No. 623139, dated Apr. 8, 2014 (1 pages).
New Zealand Examination Report (1st) re NZ Application No. 623141, dated Apr. 9, 2014 (1 pages).
New Zealand Examination Report (1st) re NZ Application No. 624449, dated Dec. 5, 2014 (2 pages).
Photographs of the Baxter Minicap (Sep. 1, 1998) (4 pages).
U.S. Office Action, re U.S. Appl. No. 11/821,190, dated Dec. 17, 2009 (10 pages).
U.S. Office Action, re U.S. Appl. No. 11/821,190, dated Aug. 2, 2010 (14 pages).
U.S. Interview Summary, re U.S. Appl. No. 11/821,190, dated Nov. 18, 2010 (4 pages).
U.S. Office Action, re U.S. Appl. No. 11/821,190, dated Mar. 7, 2011 (16 pages).
U.S. Office Action/Notice of Allowance, re U.S. Appl. No. 11/821,190, dated Apr. 26, 2011 (9 pages).
U.S. Notice of Allowance, re U.S. Appl. No. 11/821,190, dated Jul. 29, 2011 (6 pages).
U.S. Office Action, re U.S. Appl. No. 12/214,526, dated Jun. 9, 2011 (7 pages).
U.S. Final Office Action, re U.S. Appl. No. 12/214,526, dated Oct. 31, 2011 (8 pages).
U.S. Interview Summary, re U.S. Appl. No. 12/214,526, dated Mar. 23, 2012 (3 pages).
U.S. Office Action, re U.S. Appl. No. 13/095,516, dated Dec. 21, 2011 (27 pages).
U.S. Office Action/Notice of Allowance, re U.S. Appl. No. 13/095,516, dated May 16, 2012 (18 pages).
U.S. Office Action/Non-Final, re U.S. Appl. No. 13/113,777, dated Dec. 3, 2013 (13 pages).
U.S. Office Action/Final, re U.S. Appl. No. 13/113,777, dated Aug. 25, 2014 (9 pages).
U.S. Office Action/Non-Final, re U.S. Appl. No. 13/456,853, dated Dec. 14, 2012 (16 pages).
U.S. Office Action/Final, re U.S. Appl. No. 13/456,853, dated Aug. 27, 2013 (18 pages).
U.S. Office Action, re U.S. Appl. No. 13/456,853, dated Mar. 27, 2014 (14 pages).
U.S. Office Action/Notice of Allowance, re U.S. Appl. No. 13/456,853, dated Dec. 3, 2014 (9 pages).
U.S. Office Action, re U.S. Appl. No. 13/473,057, dated Feb. 8, 2013 (20 pages).
U.S. Office Action/Final, re U.S. Appl. No. 13/473,057, dated Dec. 3, 2013 (19 pages).
U.S. Office Action, re U.S. Appl. No. 13/547,650, dated Jan. 29, 2015 (9 pages).
U.S. Office Action, re U.S. Appl. No. 13/649,569, dated May 3, 2013 (15 pages).
U.S. Office Action/Final, re U.S. Appl. No. 13/649,569, dated Aug. 23, 2013 (19 pages).
U.S. Office Action, re U.S. Appl. No. 13/649,569, dated Apr. 14, 2014 (27 pages).
U.S. Office Action, re U.S. Appl. No. 13/649,569, dated Jan. 29, 2015 (14 pages).
BD Nexvia Closed IV Catheter System, http://www.bd.com/infusion/products/ivcatheters/nexiva/index.asp, downloaded Sep. 6, 2013 in 19 pages.
Charney, "Baxter Healthcare InterlinkTM IV Access System" in 1 page, from Handbook of Modern Hospital Safety. Published Mar. 1999.
European Extended Search Report, re EP Application No. 15746055.1, dated Nov. 29, 2017.

\* cited by examiner

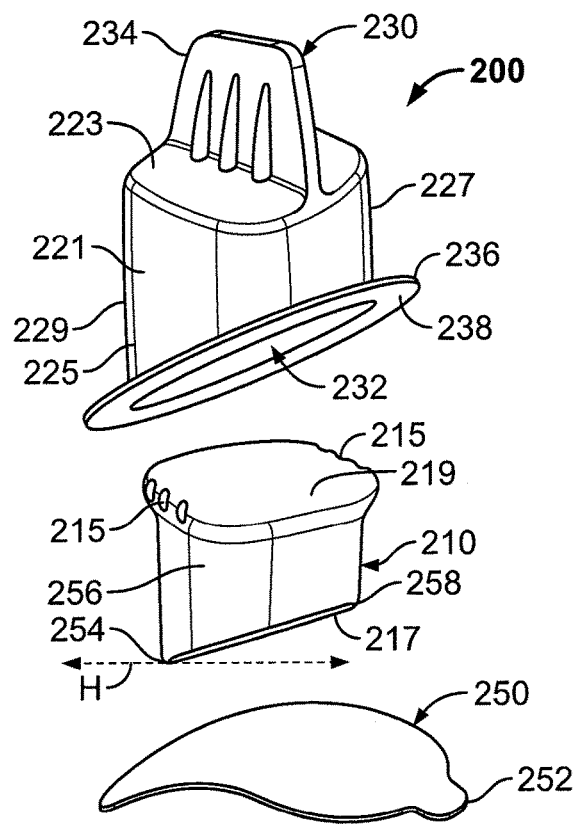
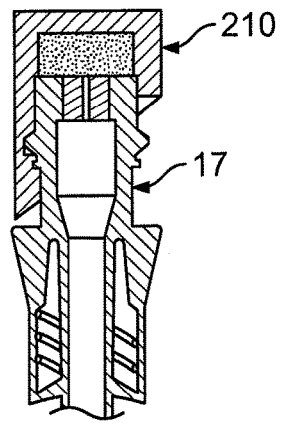
FIG. 3
FIG. 4A
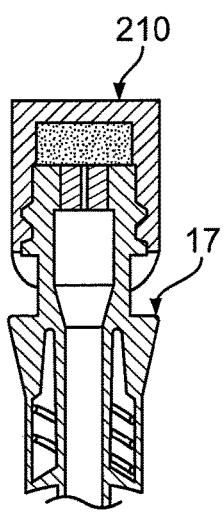
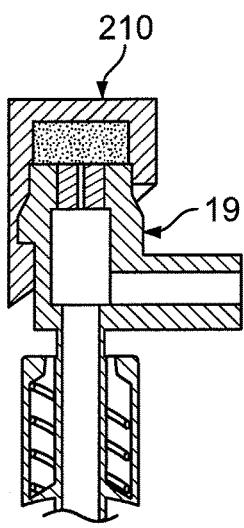
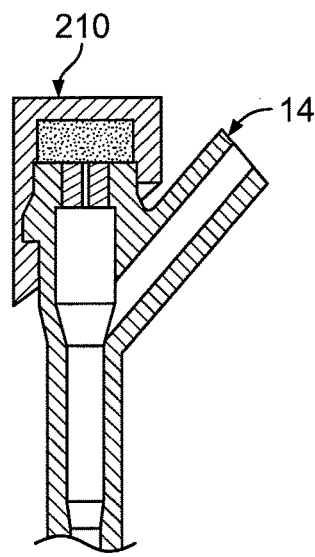
FIG. 4B
FIG. 4C
FIG. 4D

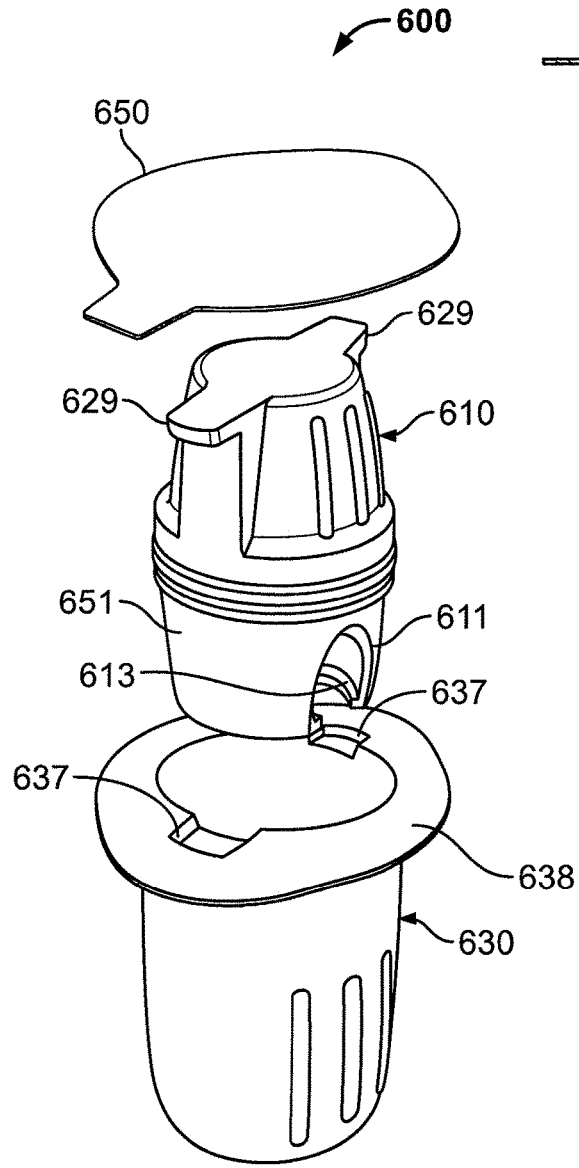
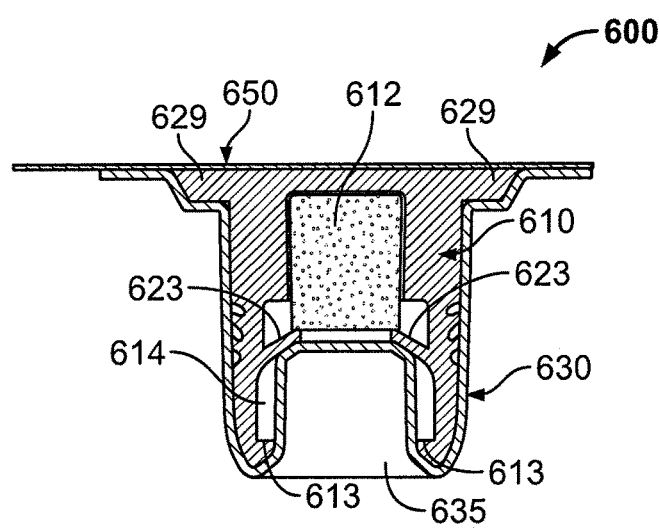
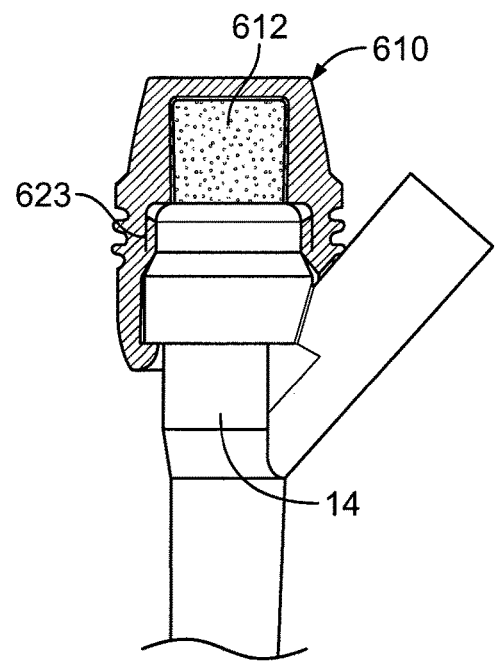
FIG. 8A
FIG. 8B
FIG. 8C

CAPS FOR NEEDLELESS CONNECTORS

CROSS-REFERENCE TO RELATED APPLICATIONS

This application is a divisional application of U.S. patent application Ser. No. 13/476,772, filed on May 21, 2012 and issued as U.S. Pat. No. 10,016,587 on Jul. 10, 2018, which claims the benefit of U.S. Provisional Application Ser. No. 61/519,324 filed May 20, 2011, the entire disclosures of each of which are all expressly incorporated herein by reference.

BACKGROUND

Field of the Invention

The present invention relates to caps for cannula access devices, and, more particularly, to antiseptic caps for cannula access devices.

Description of the Related Art

Intravenous (IV) devices are widely used to administer fluids to patients. In an IV dispensing system, a catheter is commonly caped into central veins (such as the vena cava) from peripheral vein sites to provide access to a patient's vascular system. The catheter could be connected to an injection site, such as a needleless cannula access device, which includes a split septum accessible by one end of a blunt tip plastic cannula. The other end of the blunt cannula could be connected to a fluid source, such as a conventional syringe or a fluid line in communication with a IV bag filled with fluid.

When the connectors are attached to each other, fluid from the fluid source can flow into the patient. These connectors are often separated from each other at various times, for example, when a patient needs to use the bathroom. When the connectors are disengaged from each other, the connectors are exposed and are prone to contamination. Current procedures to reduce contamination of the connectors involve swabbing the connectors with a disinfecting pad. These procedures are prone to human error and are often not implemented. Also, antiseptic caps such as Excelsior's SwabCap antiseptic cap are used to clean and cover access points. However, when a cannula access device is disengaged from a blunt cannula, there is no standard manner in which to store the cannula access device, and protect it, until it is reattached to the blunt cannula.

SUMMARY

The present invention relates to an antiseptic cap and packaging for use with a connector. The antiseptic cap includes a material containing an antiseptic solution. Upon application of the cap to the connector, the material compresses thereby releasing the antiseptic solution. Packaging of the antiseptic cap typically comprises a cap holder and a lid. In some embodiments a user could remove the cap from the cap holder before applying it to a connector. In other embodiments the cap holder may be used to aid in application of the cap to the connector. A variety of embodiments could be used to facilitate different types of connectors. A number of different types of caps can be used to assist with cap application or removal.

In one embodiment, an antiseptic cap for a cannula access device includes a sidewall defining a chamber, an undercut defining a channel formed in the sidewall, and a retention protrusion extending radially inwardly from an internal surface of the sidewall. The retention protrusion is sized to engage a surface of the cannula access device. The retention protrusion could contact a surface of the cannula access device below the septum. A cap holder or a lid could be provided as part of an antiseptic cap assembly. The cap holder has a sidewall defining a chamber sized to receive the antiseptic cap.

In another embodiment, an antiseptic cap assembly for a cannula access device includes an antiseptic cap having a sidewall with an angled bottom surface having one end and an opposite end sloped with respect to the one end. The one end is at a first horizontal level, and the opposite end is at a second horizontal level with respect to the first horizontal level.

Additionally, in another embodiment, an antiseptic cap assembly for a cannula access device includes an antiseptic cap having a sidewall, and a 'H' clip with a first side portion, a second side portion, and a hinge section. The first side portion and the second side portion are sized to pivot about the hinge portion.

In another embodiment, an antiseptic cap could include a first aperture and an absorbent material having a second aperture. The antiseptic cap could include a pin in communication with the first aperture and the second aperture, the pin having a tip.

In yet another embodiment, an antiseptic cap could include a sidewall and an undercut defining a channel formed in the sidewall, the cap configured to engage a 'Y' connector injection site and a 'T' connector injection site. In another embodiment, an antiseptic cap could include a sidewall and an angled bottom surface, the cap configured to engage a 'Y' connector injection site and a 'T' connector injection site.

A method of cleaning and covering a cannula access device is provided. The method includes the steps of applying an antiseptic cap to a 'Y' connector injection site, and allowing the antiseptic cap to remain on and cover the 'Y' connector injection site. The antiseptic cap has an antiseptic fluid therein. The antiseptic cap could be applied to other cannula access devices, such as a 'T' connector injection site.

BRIEF DESCRIPTION OF THE DRAWINGS

FIG. 3 is an exploded perspective view showing a cap assembly of the present invention, where an antiseptic cap and a cap holder each have an angled bottom surface;

FIG. 4A is a cross-sectional view of the antiseptic cap of FIG. 3 applied to an injection site;

FIG. 4B is a cross-sectional view of the antiseptic cap of FIG. 3 applied to the injection site, taken from the right side of the cap shown in FIG. 4A;

FIG. 4C is a cross-sectional view of the antiseptic cap of FIG. 3 applied to a 'T' connector injection site;

FIG. 4D is a cross-sectional view of the antiseptic cap of FIG. 3 applied to a 'Y' connector injection site;

FIG. 8A is an exploded perspective view showing another embodiment of the cap assembly, where a cap has grip protrusions;

FIG. 8B is a cross-sectional assembled view of the cap assembly of FIG. 8A;

FIG. 8C is a cross-sectional view of the cap of FIG. 8A applied to an injection site;

DETAILED DESCRIPTION

Figure 1A:
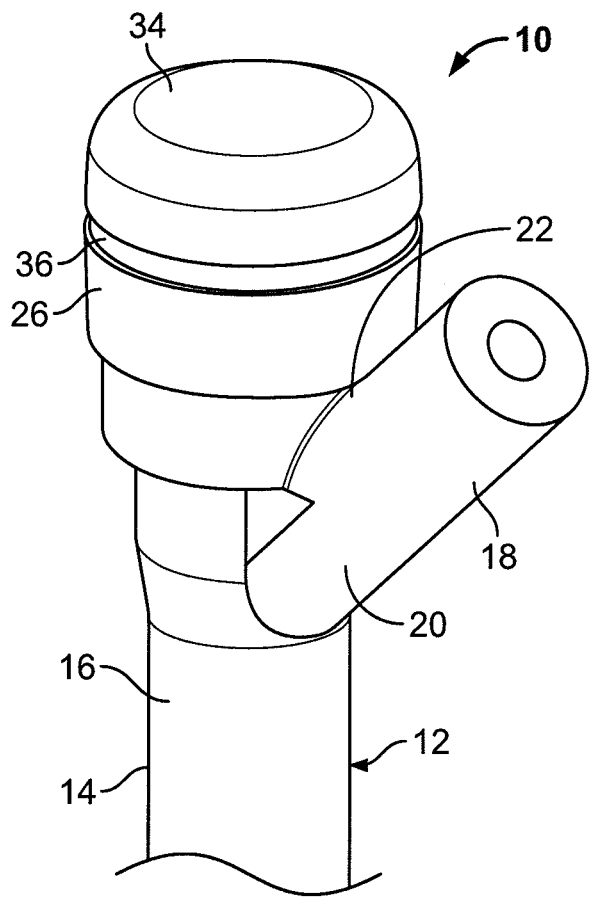
FIG. 1A is a perspective view of an antiseptic cap engaged to an injection site according to the present invention.
Figure 1B:
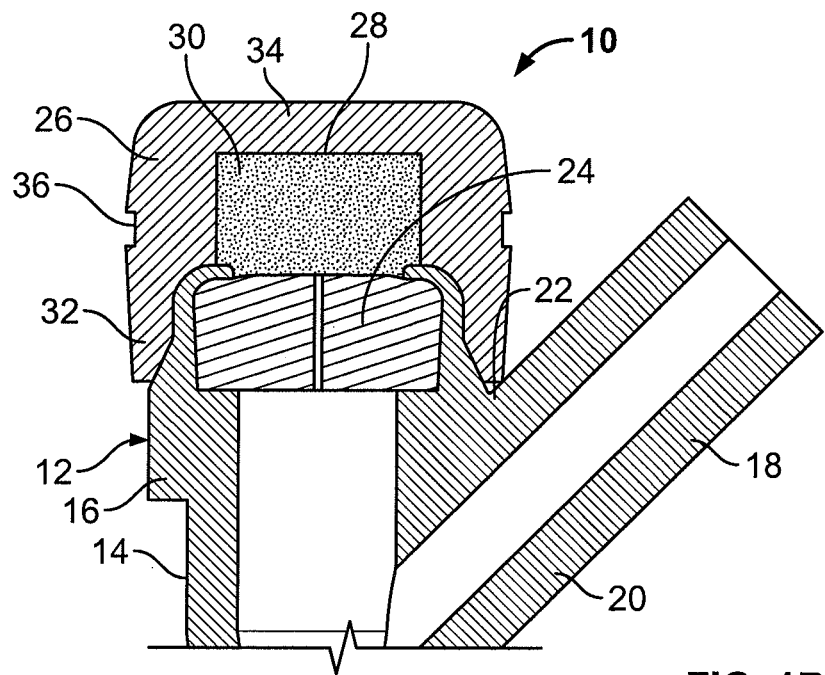
FIG. 1B is a cross-sectional view of the antiseptic cap of FIG. 1A engaged to an injection site.

FIGS. 1A-1B are views of an antiseptic cap 10 engaged to an injection site 12. The injection site 12 could be a needleless cannula access device. One type of a cannula access device is known as INTERLINK, which is available from Baxter Healthcare Corp., based in Round Lake, Ill.

Other types of cannula access devices are known as SAFE-LINE, which is available from B. Braun Medical Inc., based in Bethlehem, Pa. and LIFESHIELD, which is available from Hospira, Inc., based in Lake Forest, Ill.

The injection site 12 could be a conventional access connector, a connector known as a 'T' injection site, a connector known as a 'Y' site 14 (as shown in FIGS. 1A-1B), or a manifold which contains a plurality of connectors. The 'Y' connector injection site 14 includes a main arm 16, an angled branch 18 having one end 20 attached to the main arm 16 at an intersection 22, and a split septum 24 (FIG. 1B) accessible by one end of a blunt tip plastic cannula (not shown). The other types of injection sites will be described hereinafter.

The antiseptic cap 10 has a generally cylindrically shaped sidewall 26 that defines a chamber 28 sized to accommodate the injection site 12. The chamber 28 contains an antiseptic which could be carried by an absorbent material, such as a sponge 30, positioned within the chamber 28. Alternatively, the antiseptic cap 10 could be fully or partially formed of an adsorbent material. The sidewall 26 has an edge 32 that defines an open end. The antiseptic cap could include a substantially flat surface 34 that defines an opposite, closed end. The antiseptic cap could include a cylindrical groove 36 formed therein. The antiseptic cap 10 could be made from a thermoplastic elastomer, such as the thermoplastic elastomer sold by ExxonMobil under the trademark Santoprene, plastic, a plastic and thermoplastic elastomer combination, silicone, or any other suitable material.

The absorbent material could be made from foam, cotton, regenerated cellulose, porous plastic, urethane, silicone, bonded fiber, plastic non-woven, polyester, cellulose, or any other suitable material. A suitable porous plastic is a medical grade sintered porous plastic, which is available from Porex Corporation, based in Fairburn, Ga. Other suitable manufacturers of the porous plastic material include Filtrona, Genpore, and Thermopore. The porous plastic material could be made of any suitable polymer, such as polyethylene, polypropylene, nylon, etc. A suitable manufacturer of the bonded fiber material is Filtrona Porous Technologies, based in Richmond, Va. It is desirable that the absorbent material can retain a fluid such as a disinfectant. It is also desirable that the absorbent material is compressible and that the absorbed fluid is released on compression. The absorbent material could be natural or synthetic.

The absorbent material could be impregnated with an antiseptic fluid, an anticoagulant fluid, and/or an antimicrobial fluid. An example of a suitable antiseptic fluid is isopropyl alcohol. The concentration of the isopropyl alcohol could vary. It will be understood that other materials could be used, such as other alcohols, including ethanol, propanol, and/or butanol, or iodine, hydrogen peroxide, chlorhexidine, chlorhexidine gluconate, chlorhexidine acetate, silver, triclosan, etc. The antiseptic, anticoagulant, and/or antimicrobial agent could be in liquid or solid form.

The use of the absorbent material is only exemplary. It will be understood that the absorbent material could be replaced with a material, which contains an antiseptic fluid, an anticoagulant fluid, and/or an antimicrobial fluid. Suitable materials include alcohols, including ethanol, propanol, isopropyl, and/or butanol, or iodine, hydrogen peroxide, chlorhexidine, chlorhexidine gluconate, chlorhexidine acetate, silver, triclosan, etc. It will also be understood that an antiseptic fluid, an anticoagulant fluid, and/or an antimicrobial fluid could be applied directly to the antiseptic cap. For example, the antiseptic cap 10 could be made from an absorbent material, or the antiseptic cap 10 could be coated or impregnated with an antiseptic fluid, an anticoagulant fluid, and/or an antimicrobial fluid.

Referring to FIG. 1B, the antiseptic cap 10 is shown attached to the 'Y' connector injection site 14 such that the sidewall 26 is adjacent the intersection 22 between the main arm 16 and the angled branch 18. In this position, the sponge 30 is compressed between the substantially flat surface 34 of the antiseptic cap 10 and the septum 24, which releases at least a portion of the antiseptic fluid to disinfect the surface of the septum 24 and areas adjacent to the septum 24. The antiseptic cap 10 can be allowed to remain attached to the 'Y' connector injection site 14 for any suitable period of time where the antiseptic cap 10 disinfects and protects the 'Y' connector injection site 14 until the next time the 'Y' connector injection site 14 is accessed. When the antiseptic cap 10 is attached to the 'Y' connector injection site 14, the septum 24 is exposed to the antiseptic fluid. Also, when the antiseptic cap 10 is engaged to the 'Y' connector injection site 14, the antiseptic cap 10 serves as a physical barrier from contamination. The antiseptic cap 10 could be secured to the injection site 12 by vacuum or an interference fit. The antiseptic cap 10 could be configured with threads (not shown).

Although the embodiment of the antiseptic cap 10 shown in FIGS. 1A-1B is engaged to a 'Y' connector injection site 14, it will be understood that the antiseptic cap 10 could engage other types of injection sites, as will be described hereinafter.

Figure 2A:
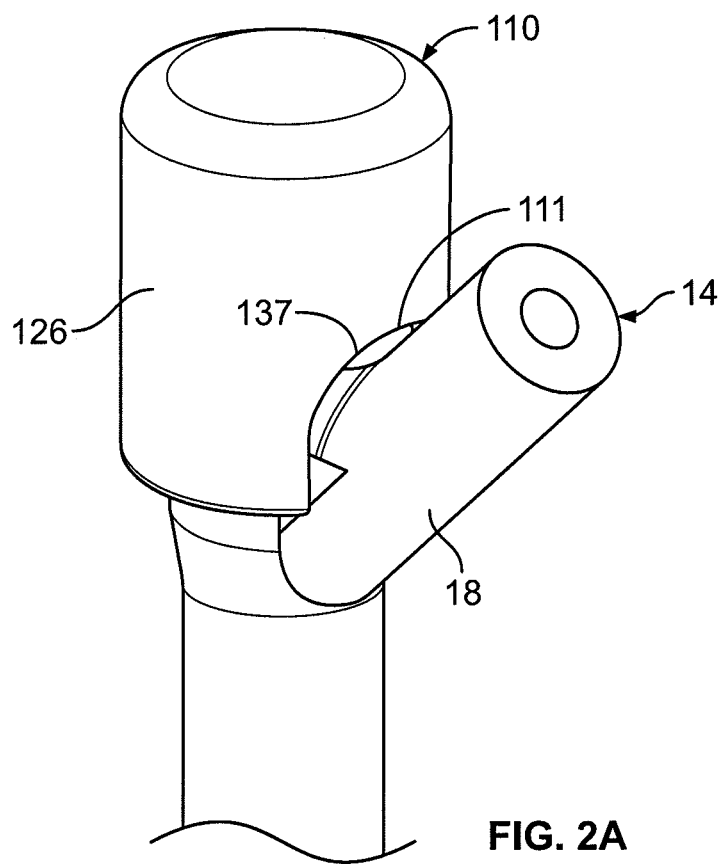
FIG. 2A is a perspective view showing another embodiment of the antiseptic cap engaged to an injection site, where the antiseptic cap has one channel.
Figure 2B:
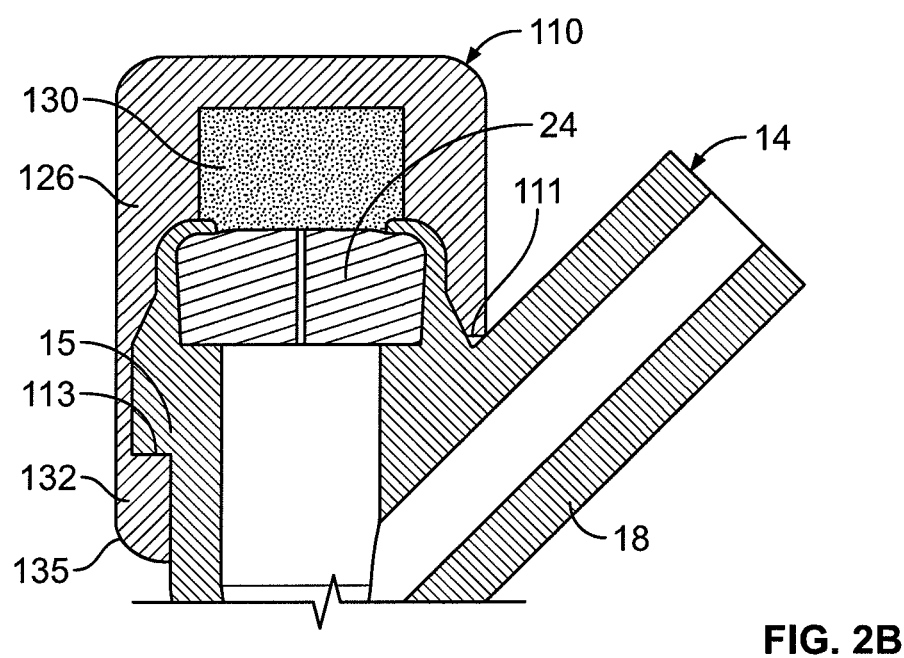
FIG. 2B is a cross-sectional view of an antiseptic cap of FIG. 2A engaged to an injection site.

FIGS. 2A-2B show another embodiment of an antiseptic cap, indicated generally as 110, that is sized to engage and disinfect an injection site, such as the 'Y' connector injection site 14. The antiseptic cap 110 operates and is constructed in manners consistent with the antiseptic cap 10 shown in FIGS. 1A-1B, unless stated otherwise Like the antiseptic cap 10, the antiseptic cap 110 includes a sponge 130.

The antiseptic cap 110 could include an undercut 111 defining a channel formed in the generally cylindrical sidewall 126. The undercut 111 allows the antiseptic cap 110 to clear the angled branch 18 of the 'Y' connector injection site 14, as shown, or a 'T' connector injection site, thereby allowing additional areas below the septum 24 to be disinfected and protected, relative to the areas of the 'Y' connector injection site 14 by the antiseptic cap 10 (FIGS. 1A-1B). In this position, the antiseptic cap 110 covers additional areas of the 'Y' connector injection site 14 and is retained securely on the 'Y' connector injection site 14. The antiseptic cap 110 could include an annular engagement protrusion 113 protruding internally from the edge 132 of the generally cylindrical sidewall 126. The engagement protrusion 113 can engage an exterior surface 15 of the 'Y' connector injection site 14 further securing the cap 110 thereto.

The sidewall 126 has one bottom end 135 and an opposite bottom end 137 defined by the undercut 111. The one bottom end 135 is at a different height or horizontal level than the opposite bottom end 137. The one bottom end 135 of the sidewall 126 is sized to engage a surface of the injection site 14 at a first horizontal level, and the opposite bottom end 137 is sized to engage another surface of the injection site 14 at a second horizontal level with respect to the first horizontal level.

FIG. 3 shows a cap assembly 200 that includes another embodiment of an antiseptic cap, generally indicated as 210. The cap assembly includes a cap holder 230 and the antiseptic cap 210 is sized to be positioned within the cap holder 230.

The cap holder 230 includes a sidewall 221 that defines a chamber 232 sized to receive the antiseptic cap 210 therein. The cap holder 230 could include a gripping area, such as a fin 234 extending from a top closed surface 223 of the cap holder 230. In one embodiment, the fin 234 is a vertical wall extending from a central surface of the top closed surface 223 of the cap holder 230. The fin 234 is configured for gripping the cap holder 230 to facilitate attachment of the cap holder 230 to the injection site 12. The cap holder 230 includes an annular flange 236 extending radially outwardly from a distal end 225 of the sidewall 221 and forming a bottom surface 238 of the cap holder 230. The annular flange 236 defines an opening formed in the chamber 232. The annular flange 236 can be angled such that one end 227 of the sidewall 221 is sloped with respect to an opposite end 229 of the sidewall 221. The cap holder 230 could be made from a rigid or semi-rigid material, such as high-density polyethylene, or any other suitable material.

In this embodiment, the antiseptic cap 210 includes an angled bottom surface 217. The angle formed by the bottom surface 217 of the antiseptic cap 210 could be the same as the angle formed by the annular flange 236 of the cap holder 230, or it could be different. In one embodiment, the angle formed by the bottom surface 217 of the antiseptic cap 210 is between one to eighty-nine degrees relative to a horizontal axis H. The angled bottom surface 217 can be angled such that one end 254 of the sidewall 256 is sloped with respect to an opposite end 258 of the sidewall 256. The one end 254 is at a different height or horizontal level than the opposite end 258. The one bottom end 254 of the sidewall 256 is sized to engage a surface of the injection site 14 at a first horizontal level, and the opposite bottom end 258 is sized to engage another surface of the injection site 14 at a second horizontal level with respect to the first horizontal level.

The antiseptic cap 210 could include finger gripping areas, such as a plurality of indentations 215 along a surface 219 of the antiseptic cap 210. The indentations 215 could be configured for gripping the antiseptic cap 210 to facilitate removal of the antiseptic cap 210 from the injection site 12.

The angled annular flange 236 of the cap holder 230 and the angled bottom surface 217 of the antiseptic cap 210 allow for compatibility with various injection sites, such as the 'Y' connector injection site and the 'T' connector injection site, as described herein.

As shown in FIG. 3, the cap holder 230 could be sealed with a material, such as a lid 250, which could be formed of a foil material, or a lid stock material, which can be applied to the annular flange of the cap holder by any suitable method such as by adhesive or by conductive or inductive heat sealing techniques. A pull tab 252 could be provided to facilitate removal of the lid 250 to provide access to the antiseptic cap 210.

The cap holder 230 could be used to aseptically apply the antiseptic cap 210 to an injection site. The cap holder 230 and the lid 250 cover and protect the antiseptic cap 210 to provide a sterile barrier.

The cap holder 230 could be configured to be removably attached to the antiseptic cap 210. For example, the cap holder 230 could be removed from the antiseptic cap 210 after the cap assembly 200 engages the injection site 12. Alternatively, the cap holder 230 could remain on the injection site 12 after the cap assembly 200 engages the injection site 12. As another alternative, a user may remove the antiseptic cap 210 from the cap holder 230 and then apply the antiseptic cap 210 to an injection site 12.

FIGS. 4A-4E are cross-sectional views of the antiseptic cap assembly 210 engaged to various types of injection sites.

Figure 4E:
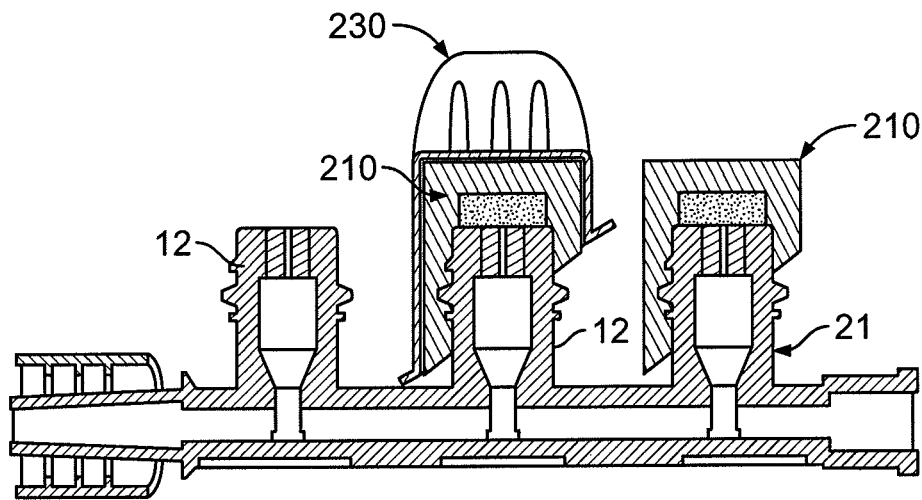
FIG. 4E is cross-sectional view of the antiseptic cap and the cap holder of FIG. 3 applied to an injection manifold.

The angled annular flange of the cap holder and the angled bottom surface of the antiseptic cap allow the antiseptic cap 210 to attach to a conventional injection site 17 (as shown in FIGS. 4A-4B), the 'T' site connector 19 (as shown in FIG. 4C), and the 'Y' site connector 14 (as shown in FIG. 4D). Further, the cap 210 could be applied to an injection manifold 21 (as shown in FIG. 4E), which includes a plurality of injection sites. The antiseptic cap 210 is sized so that there is sufficient space for an antiseptic cap 210 to be applied to each injection site of the manifold 21. The sidewall 126 has one bottom end 135 and an opposite bottom end 137 defined by the undercut 111.

Figure 5:
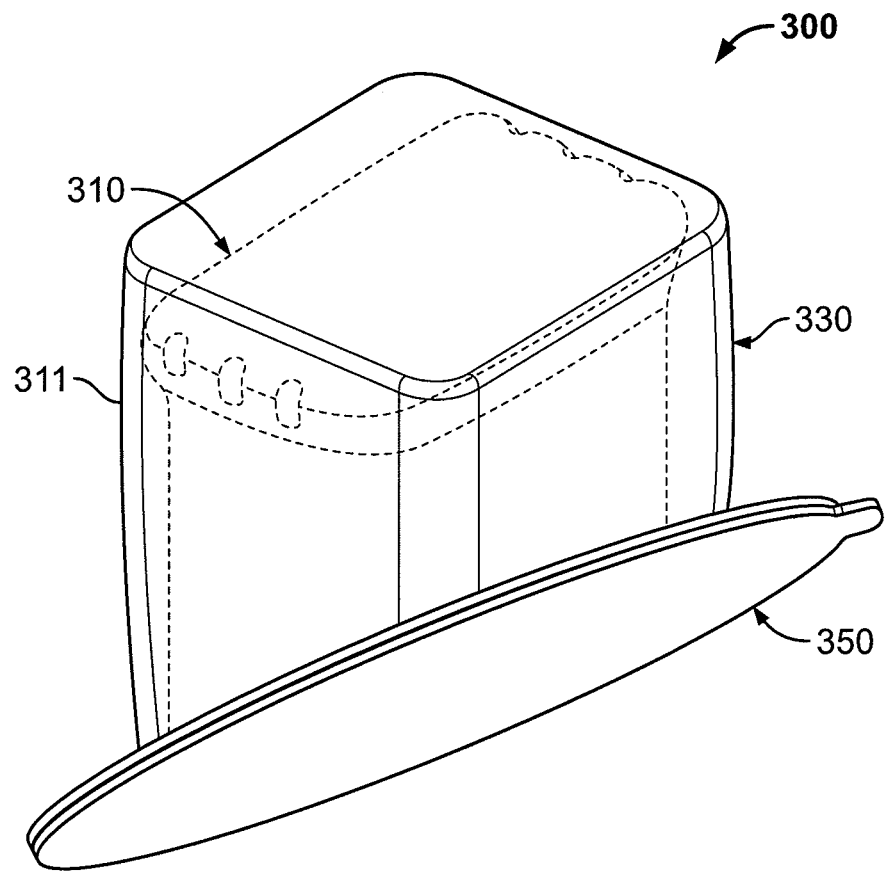
FIG. 5 is a perspective view showing another embodiment of the antiseptic cap assembly, where a cap holder has a generally planar top surface.

FIG. 5 shows another embodiment of a cap assembly, generally indicated as 300. The cap assembly 300 operates and is constructed in manners consistent with the cap assembly 200 shown in FIG. 3, unless stated otherwise. The cap assembly 300 includes a cap holder 330, an antiseptic cap 310 sized to be positioned within the cap holder 330, and a lid 350. In this embodiment, the cap holder 330 has a generally planar upper surface. A user could use an exterior surface 311 of the cap holder 330 to apply the cap 310 to an injection site.

Figure 6A:
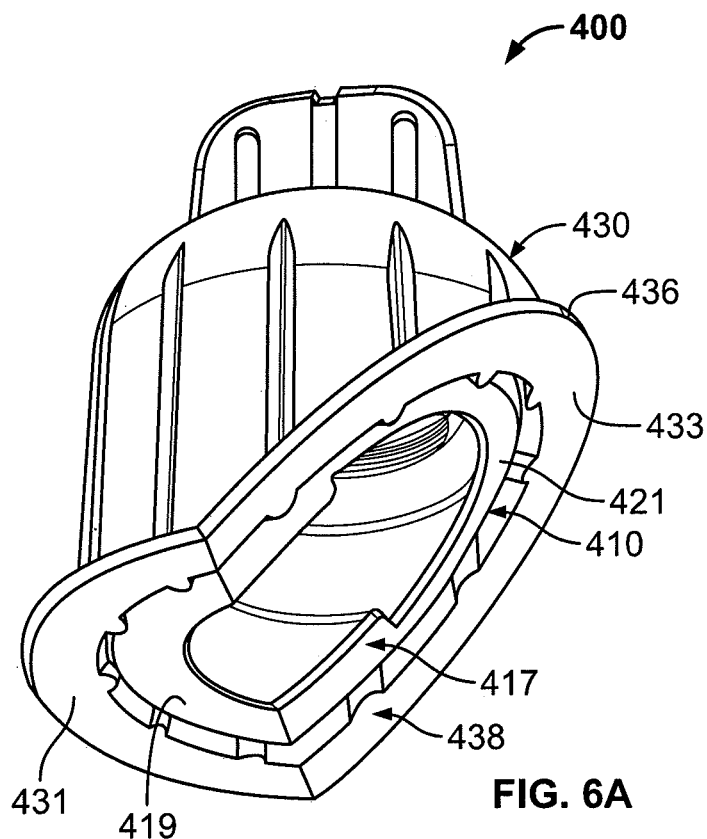
FIG. 6A is a perspective view showing another embodiment of the antiseptic cap assembly, where a cap and a cap holder each have a bottom surface comprising a flat portion and an angled portion.
Figure 6B:
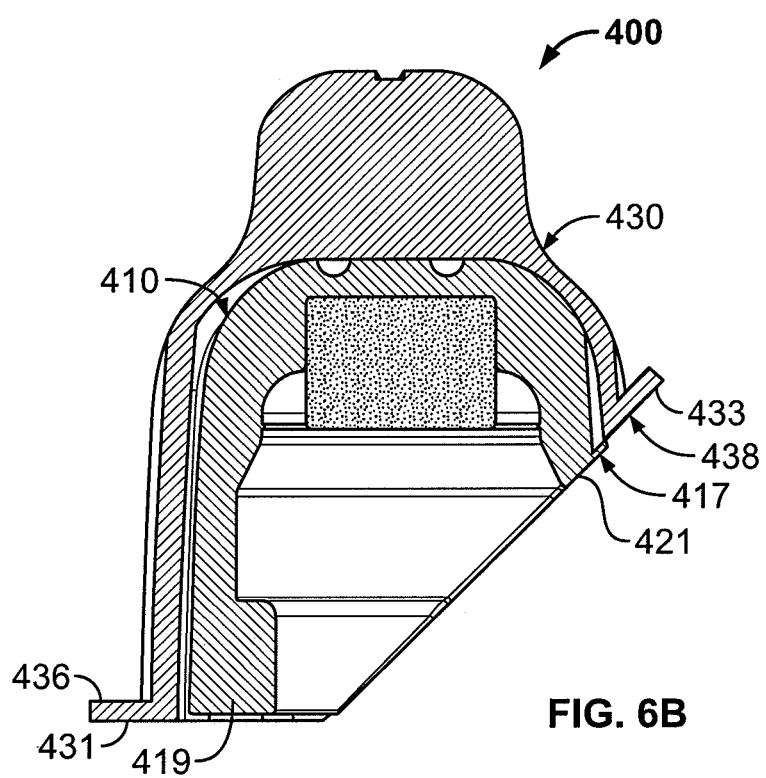
FIG. 6B is cross-sectional view of the cap assembly of FIG. 6A.

FIGS. 6A-6B show another embodiment of a cap assembly, generally indicated as 400. The cap assembly 400 operates and is constructed in manners consistent with the cap assembly 200 shown in FIG. 3, unless stated otherwise. A bottom surface 438 of a flange 436 of the cap holder 430 is partially angled such that the bottom surface 438 is split into a flat portion 431 and an angled portion 433. Likewise, a bottom surface 417 of the antiseptic cap 410 is partially angled such that the bottom surface 417 is split into a flat portion 419 and an angled portion 421. The partially angled flange 436 of the cap holder 430 and the partially angled bottom surface 417 of the antiseptic cap 410 allow for compatibility with various injection sites, such as the 'Y' connector injection site and the 'T' connector injection site.

Figure 7A:
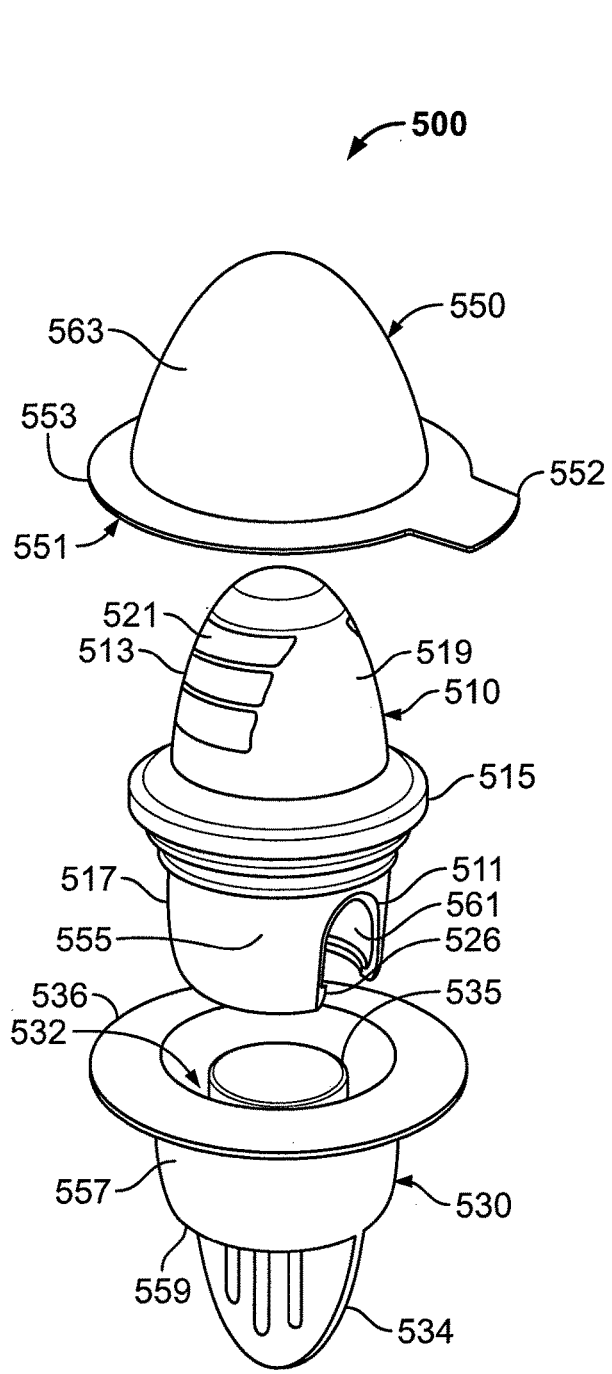
FIG. 7A is an exploded perspective view showing another embodiment of the cap assembly, where a cap comprises a compressible top portion.
Figure 7B:
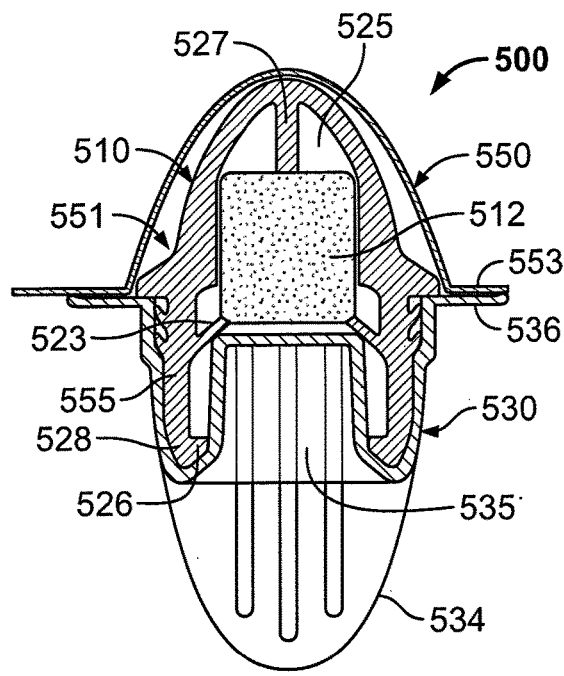
FIG. 7B is a cross-sectional view of the cap assembly of FIG. 7A.

FIGS. 7A-7B show another embodiment of a cap assembly, generally indicated as 500. The cap assembly 500 operates and is constructed in manners consistent with the cap assembly 200 shown in FIG. 3, unless stated otherwise. The cap assembly 500 includes an antiseptic cap 510, a cap holder 530, and a lid 550.

Figure 7C:
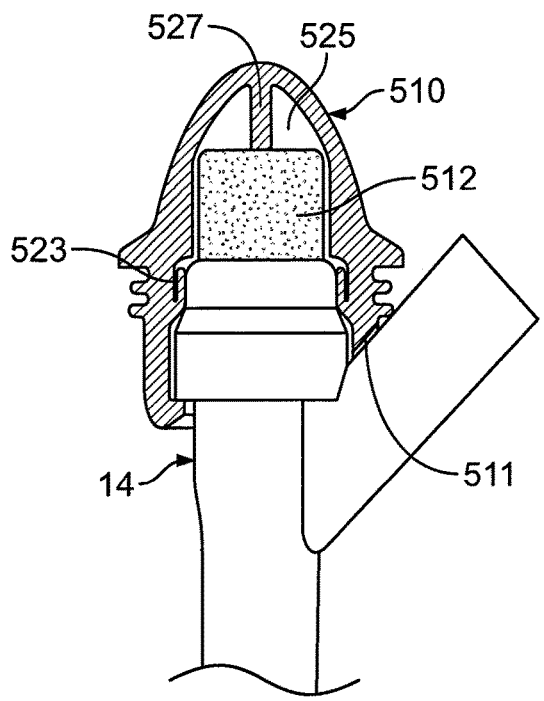
FIG. 7C is a cross-sectional view of the cap of FIG. 7A applied to an injection site.

The antiseptic cap 510 could include a top portion 513, a bottom portion 517, and a plurality of flanges 515 located between the top portion 513 and the bottom portion 517. The top portion 513 includes a generally ellipsoid-shaped sidewall 519 extending from the flanges 515. The generally ellipsoid-shaped sidewall 519 tapers (becomes smaller) upwardly and in a direction away from the flanges 515. The sidewall 519 defines a cavity 525 (FIGS. 7B-7C) to allow the sidewall 519 to be compressible, and facilitates gripping and removal of the antiseptic cap 510. The cap 510 could include an internal wall or protrusion 527 (FIGS. 7B-7C) extending downwardly into the cavity 525. When the antiseptic cap 510 engages the injection site 14, the absorbent material 512 compresses between the internal wall 527 and the top of the injection site 14. The antiseptic cap 510 could include finger grips 521 on an outer surface of the top portion 513.

The bottom portion 517 includes a sidewall 555 defining a chamber 561 with an annular retention protrusion 526 protruding from an edge 528 of an internal surface of the sidewall 555. The annular retention protrusion 526 is sized to mate against a bottom of the septum 24 and serves to retain the antiseptic cap 510 against the septum 24. The cap 510 could further include an undercut 511 defining a channel formed in the sidewall 555. The channel 511 allows for application to the 'Y' connector injection site and to the 'T' connector injection site. The antiseptic cap 510 could include a sealing blade 523 extending inwardly, and distally, from an internal surface of the sidewall 555. In one embodiment, the sealing blade 523 extends radially inwardly.

The cap holder 530 could include a sidewall 557 defining a chamber 532 sized to receive the sidewall 555 of the cap 510, a fin 534 extending from a bottom closed surface 559, and a flange 536 defining an open end into the chamber 532. Additionally, the cap holder 530 could include an axial protrusion 535 shaped to correspond to the chamber 561 of the antiseptic cap 510 to prevent deformation of the antiseptic cap 510, and to maintain the antiseptic solution in the antiseptic material 512. The cap holder 530 is sized to receive the sidewall 555 of the antiseptic cap 510 such that the channel formed in the sidewall 555 is situated over the axial protrusion 535.

When the antiseptic cap 510 is engaged to the cap holder 530, the sealing blade 523 is positioned between the sponge 512 (FIGS. 7B-7C) and the protrusion 535 formed in the cap holder 530. In this position, the internal sealing blade 523 serves to assist with retaining the sponge 512 in the cap 510 prior to engagement with an injection site 14. The sealing blade 523 also assists with maintaining the sponge 512 in position when the antiseptic cap 510 is engaged to the injection site. The sealing blade 523 provides constricting pressure against the external surface of the injection site 14 to secure the cap 510 to the injection site 14. The sealing blade 523 could be formed at any location along the length of the antiseptic cap 510 and could be a continuous or interrupted interior annular protrusion. While one sealing blade 523 is shown, it will be understood that the number of sealing blades, and the orientation thereof, could vary. The sealing blade 523 could be made from a flexible material or any other suitable material.

The lid 550 includes a generally ellipsoid-shaped outer wall 563 defining a chamber 551 sized to accommodate the sidewall 519 of the cap 510. The generally ellipsoid-shaped outer wall 563 tapers (becomes smaller) upwardly. The shape of the lid 550 is generally complimentary to the shape of the sidewall 519 of the antiseptic cap 510. The lid 550 further includes a flange 553 which can be applied to the flange 536 of the cap holder 530, and a tab 552 for removal of the lid 550. The lid 550 and the cap holder 530 cooperate to seal the antiseptic cap 510 within the cap holder 530.

FIGS. 8A-8C show another embodiment of a cap assembly, generally indicated as 600. The cap assembly 600 operates and is constructed in manners consistent with the cap assembly 500 shown in FIGS. 7A-7C, unless stated otherwise. The cap assembly 600 includes an antiseptic cap 610, a cap holder 630, and a lid 650.

Like the cap 510, the cap 610 could include engagement protrusions 613, an undercut 611 formed in the sidewall 651, and a sealing blade 623. Additionally, the cap 610 includes diametrically opposed grip protrusions 629 to assist a user in removal of the antiseptic cap 610 from the cap holder 630.

The cap holder 630 includes a flange 638, which could be pliable, with recesses 637 to accommodate the grip protrusions 629 of the antiseptic cap 610. The flange 635 assists a user in removing the antiseptic cap 610 from the cap holder 630. Like the cap holder 530, the cap holder 630 includes an axial protrusion 635 (FIG. 8B) shaped to correspond to the chamber 614 of the antiseptic cap 610 to retain the antiseptic material 612 in place, and to retain the antiseptic solution in the antiseptic material 612.

Figure 9A:
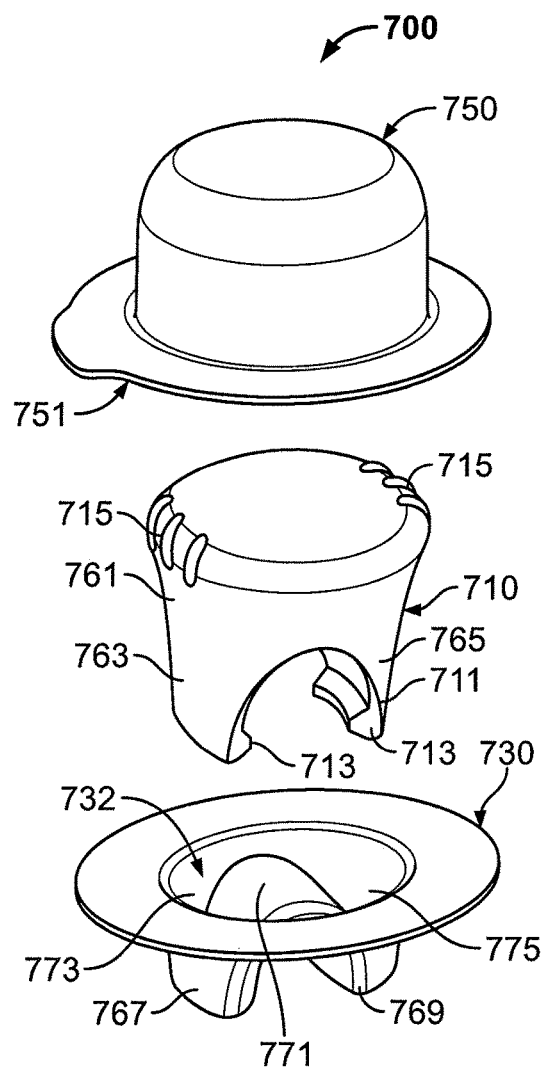
FIG. 9A is an exploded perspective view showing another embodiment of the cap assembly, where a cap has two channels.
Figure 9B:
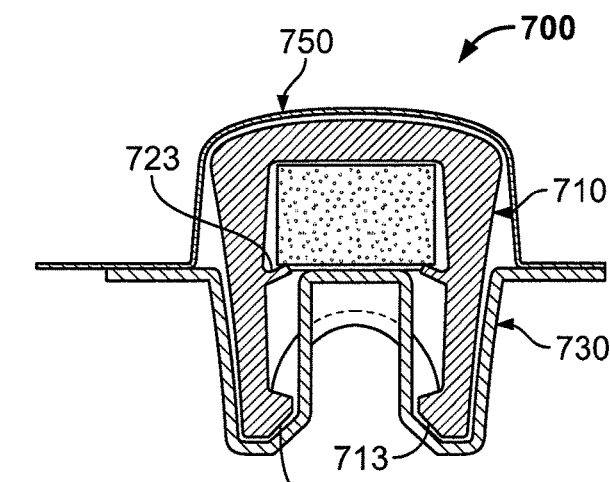
FIG. 9B is a cross-sectional assembled view of the cap assembly of FIG. 9A.
Figure 9C:
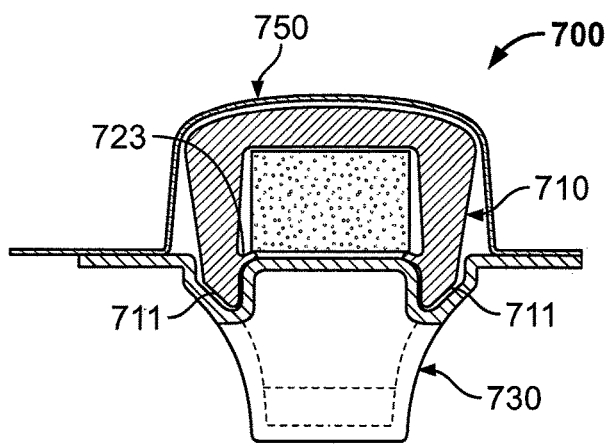
FIG. 9C is a cross-sectional assembled view of the cap assembly of FIG. 9A from the right side of the cap shown in FIG. 9B.

FIGS. 9A-9C show another embodiment of a cap assembly, generally indicated as 700. The cap assembly 700 operates and is constructed in manners consistent with the cap assembly 600 shown in FIGS. 8A-8C, unless stated otherwise. The cap assembly 700 includes an antiseptic cap 710, a cap holder 730, and a lid 750.

Like the antiseptic cap 610, the cap 710 comprises engagement protrusions 713, finger grips 715, and a sealing blade 723, as well as two diametrically opposed undercuts 711 defining two channels formed in a sidewall 761 and two legs 763, 765 extending from the sidewall 761. The sealing blade 723 (FIG. 9B) extends distally from an internal surface of the sidewall 761. It will be understood that more than one sealing blade 723 could be provided. The channels allow for application to the 'Y' connector injection site and to the 'T' connector injection site.

The cap holder 730 includes two outer legs 767, 769 and an internal protrusion 771 forming chambers 773, 775 within the two outer legs 767, 769. The chambers 773, 775 are sized to accommodate the legs 763, 765 of the antiseptic cap 710. The central chamber 732 of the cap holder 730 has a shallow depth to facilitate easy removal of the cap 710 from the cap holder 730. The lid 750 has a chamber 751 and is shaped to accommodate the shape of the cap 710 and to seal the cap 710 within the cap holder 730. The protrusion 771 can contact and form a seal for retaining antiseptic material within the antiseptic cap 710.

Figure 10:
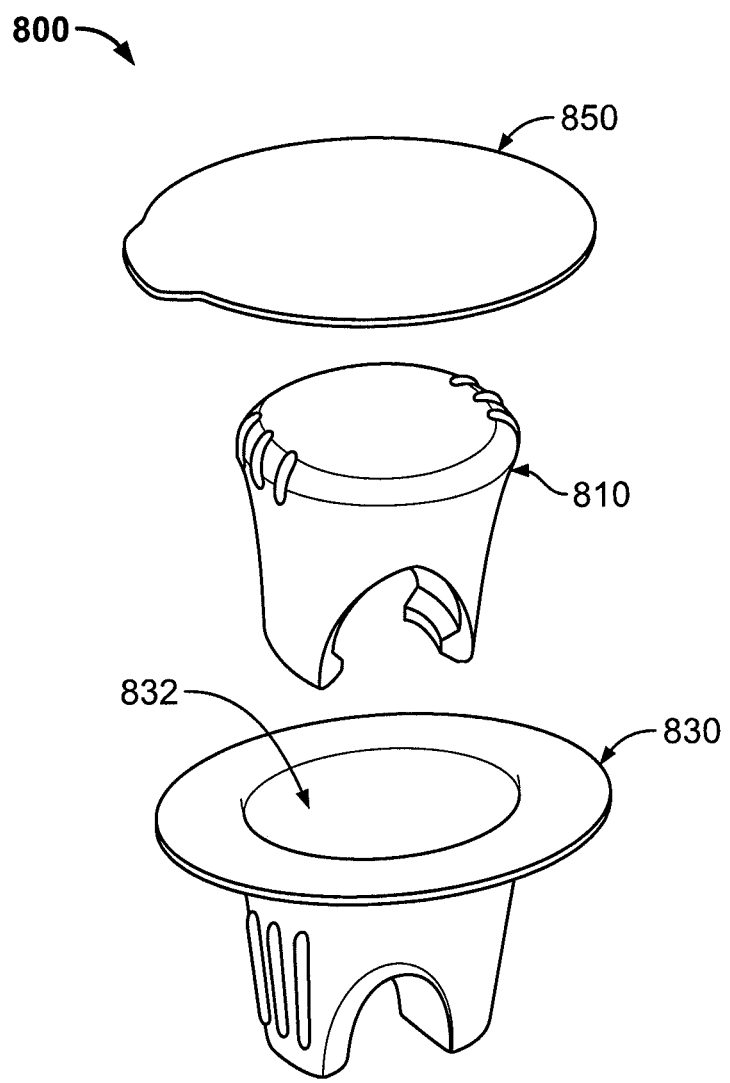
FIG. 10 is an exploded perspective view showing another embodiment of the cap assembly, where a cap has two channels.

FIG. 10 shows another embodiment of a cap assembly, generally indicated as 800. The cap assembly 800 operates and is constructed in manners consistent with the cap assembly 700 shown in FIGS. 9A-9C, unless stated otherwise. Here, the cap assembly 800 has a packaging configuration having a chamber 832 of the cap holder 830 with a depth comparable to the height of the antiseptic cap 810, and the cap 810 could be sealed therein by a lid 850 of foil or other flat material.

Figure 11A:
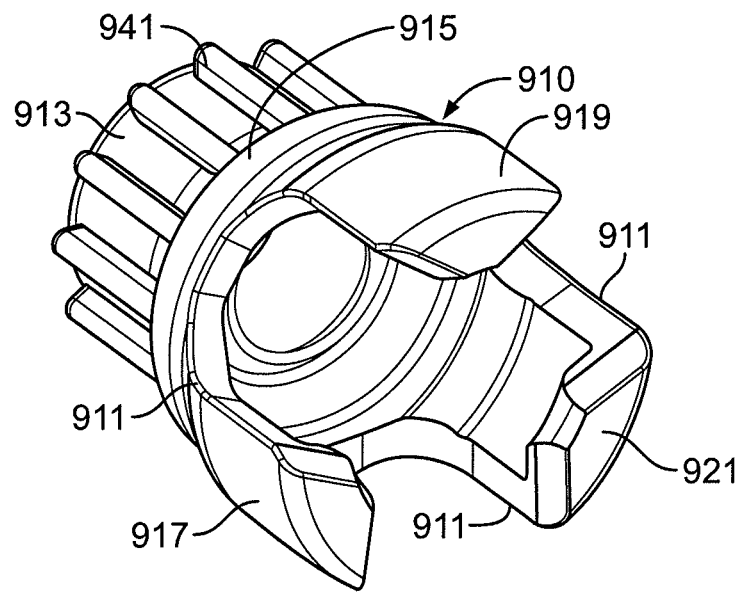
FIG. 11A is a perspective view showing another embodiment of the antiseptic cap, where an antiseptic cap has three channels.
Figure 11B:
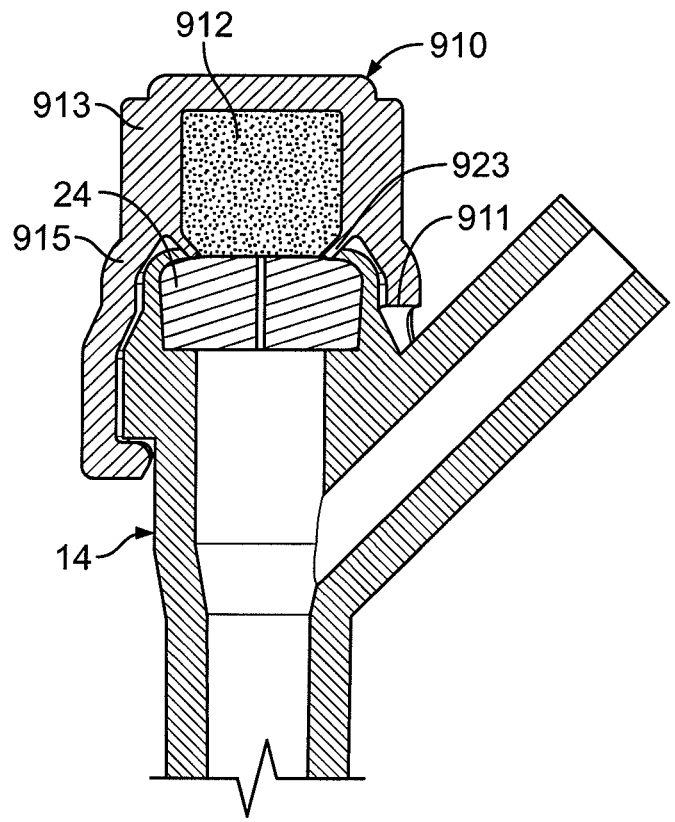
FIG. 11B is a cross-sectional view of the cap of FIG. 11A applied to an injection site, wherein the cap has retaining tabs that extend centrally within the cap.

FIGS. 11A-11B show another embodiment of an antiseptic cap, generally indicated as 910. The antiseptic cap 910 includes a generally cylindrical wall 913, a central outer wall 915, and three undercuts 911 extending from the central outer wall 915. The undercuts 911 define three channels and three legs 917, 919, 921. The undercuts 911 allow for compatibility with INTERLINK valve types, such as the 'Y' connector injection site and the 'T' connector injection site. The antiseptic cap 910 could include gripping areas, such as a plurality of circumferentially spaced ribs 941 extending radially outwardly and axially along a peripheral surface of the generally cylindrical wall 913 of the cap 910. The cap 910 includes a sealing blade 923 extending proximally from an internal surface of the cap 910. The sealing blade 923 extends radially inwardly toward the center of the antiseptic cap 910. When the antiseptic cap 910 is engaged to an injection site, the sealing blade 923 is positioned between the sponge 512 and the top of the injection site 14.

Figure 11D:
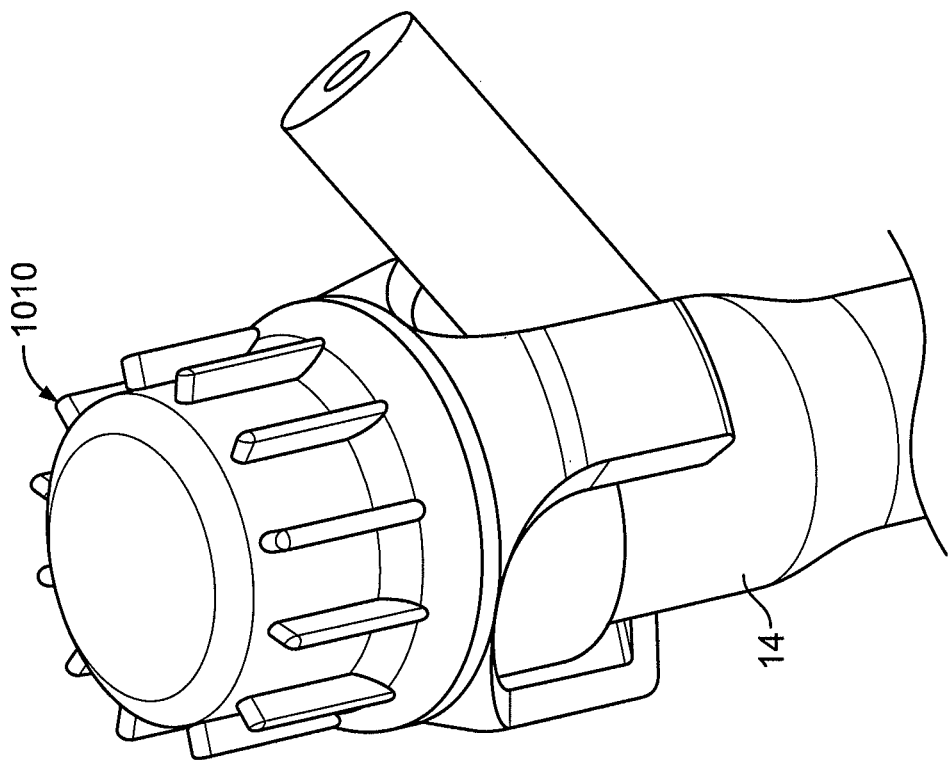
FIG. 11D is a cross-sectional view of the cap of FIG. 11C applied to an injection site.
Figure 11C:
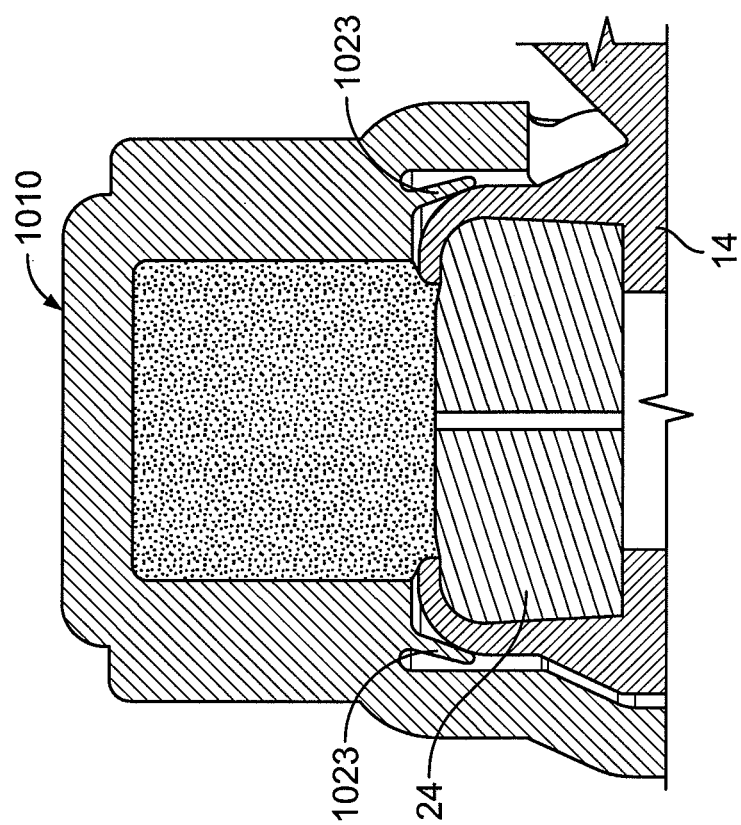
FIG. 11C is a cross-sectional view showing another embodiment of the antiseptic cap of FIG. 11A applied to an injection site, wherein a cap has retaining tabs that extend downwardly within the cap.

FIGS. 11C-11D show another embodiment of an antiseptic cap, generally indicated as 1010. The antiseptic cap 1010 operates and is constructed in manners consistent with the antiseptic cap 910 shown in FIGS. 11A-11B, unless stated otherwise. Here, the sealing blade 1023 of the antiseptic cap 1010 is positioned such that the sealing blade 1023 extends proximally away from the center of the cap 1010. When the antiseptic cap 1010 is engaged to an injection site, the sealing blade 1023 is positioned adjacent the side of the injection site.

Figure 11E:
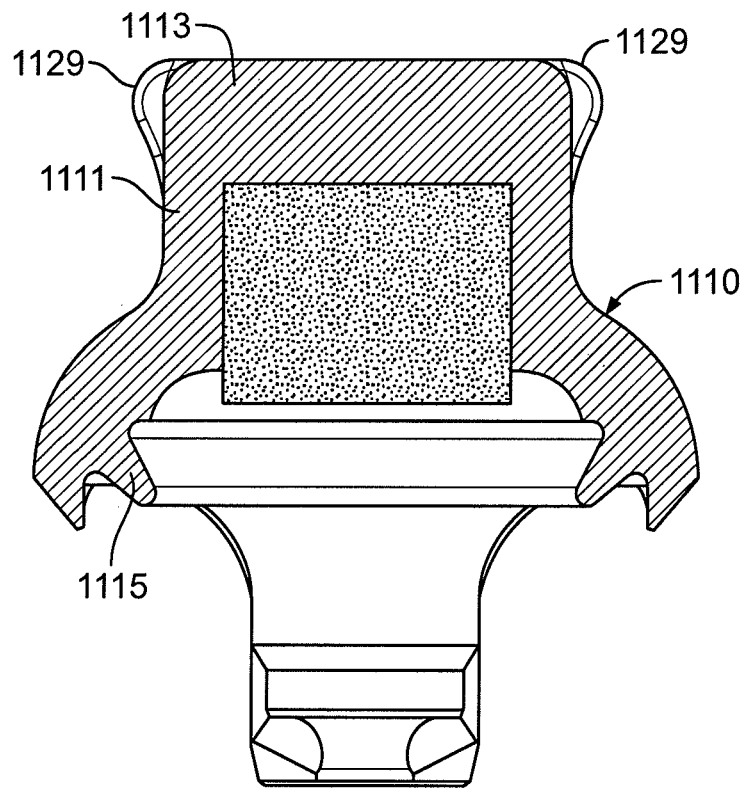
FIG. 11E is a cross-sectional view showing another embodiment of the antiseptic cap of FIG. 11A with annular gripping protrusions.
Figure 11F:
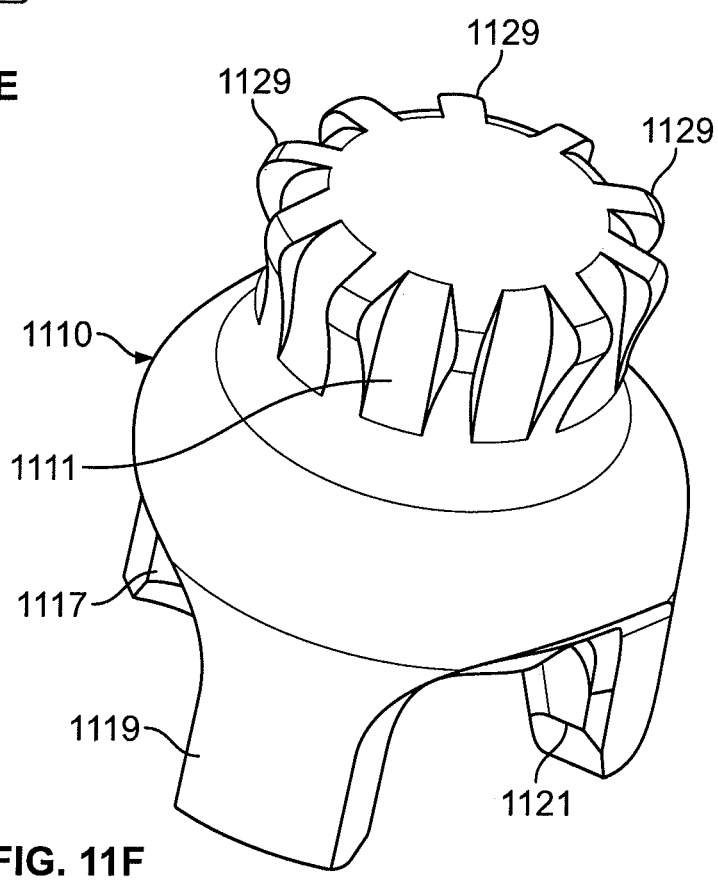
FIG. 11F is a perspective view of the cap of FIG. 11E.

FIGS. 11E-11F show another embodiment of an antiseptic cap, generally indicated as 1110. The antiseptic cap 1110 operates and is constructed in manners consistent with the antiseptic cap 910 shown in FIGS. 11A-11B, unless stated otherwise. The antiseptic cap includes a gripping area, such as a circumferentially spaced axial finger grip 1129 extending radially outwardly from an edge 1113 of a sidewall 1111 of the cap 1110. The finger grip 1129 could be hollow and compressible, thereby facilitating gripping for application and removal of the cap 1110. It will be understood that more than one axial finger grip 1129 could be provided and that the finger grip 1129 could be solid.

The antiseptic cap 1110 includes sealing blades 1115 extending from an internal surface of the legs 1117, 1119, 1121. The sealing blades 1115 extend proximally and radially inwardly toward the center of the cap 1110. When the antiseptic cap 1110 is engaged to an injection site, the sealing blades 1115 are positioned against a sidewall of the injection site. The sealing blades 1115 maintain antiseptic volume on the entire top surface of an injection site, including the septum.

Figure 12B:
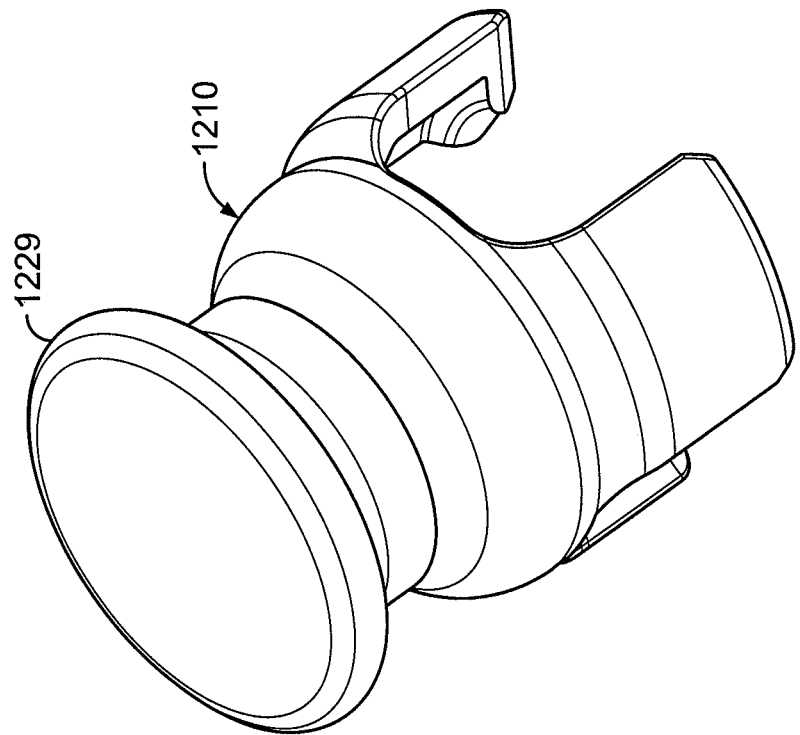
FIG. 12B is a perspective view of the cap of FIG. 12A.
Figure 12A:
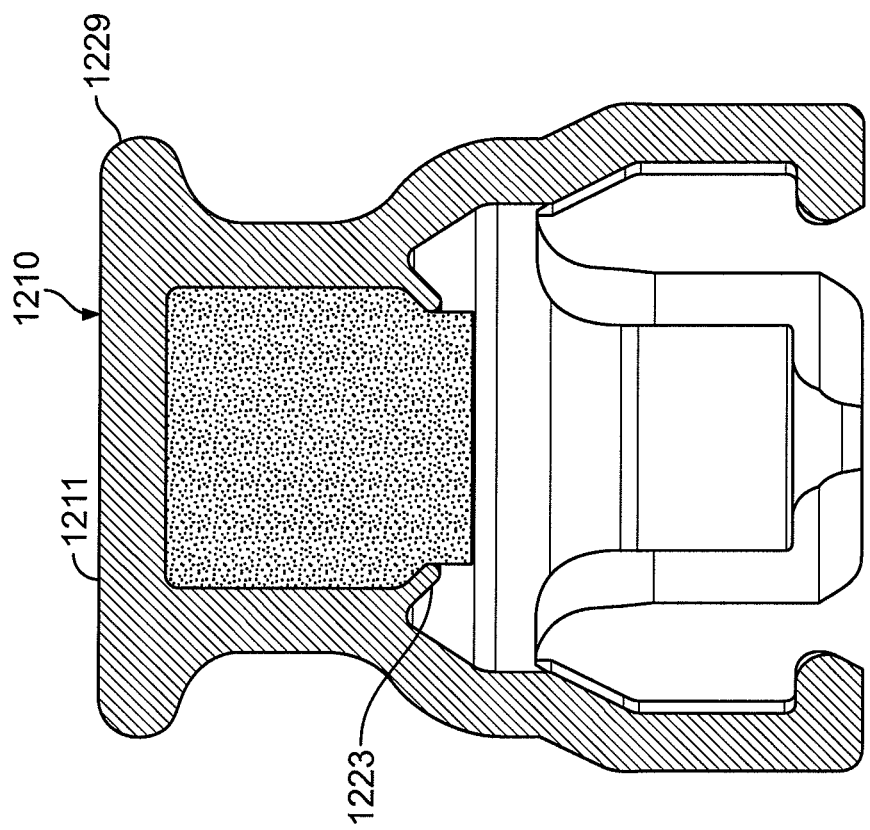
FIG. 12A is a cross-sectional view showing another embodiment of the antiseptic cap with a solid annular protrusion.

FIGS. 12A-12B show another embodiment of an antiseptic cap, generally indicated as 1210. The antiseptic cap 1210 operates and is constructed in manners consistent with the antiseptic cap 1110 shown in FIGS. 11E-11F, unless stated otherwise. The antiseptic cap includes a gripping area, such as a solid annular protrusion 1229 extending radially outwardly from a top surface 1211. The annular protrusion 1229 facilitates removal of the cap 1210 by providing a gripping surface for a user to pull up and remove the cap 1210 from an injection site, and an increased top surface by which to push down and apply the cap 1210 to an injection site. The antiseptic cap 1210 includes a sealing blade 1223 extending from an internal surface of the cap 1210. It will be understood that the protrusion 1229 could be hollow.

Figure 13A:
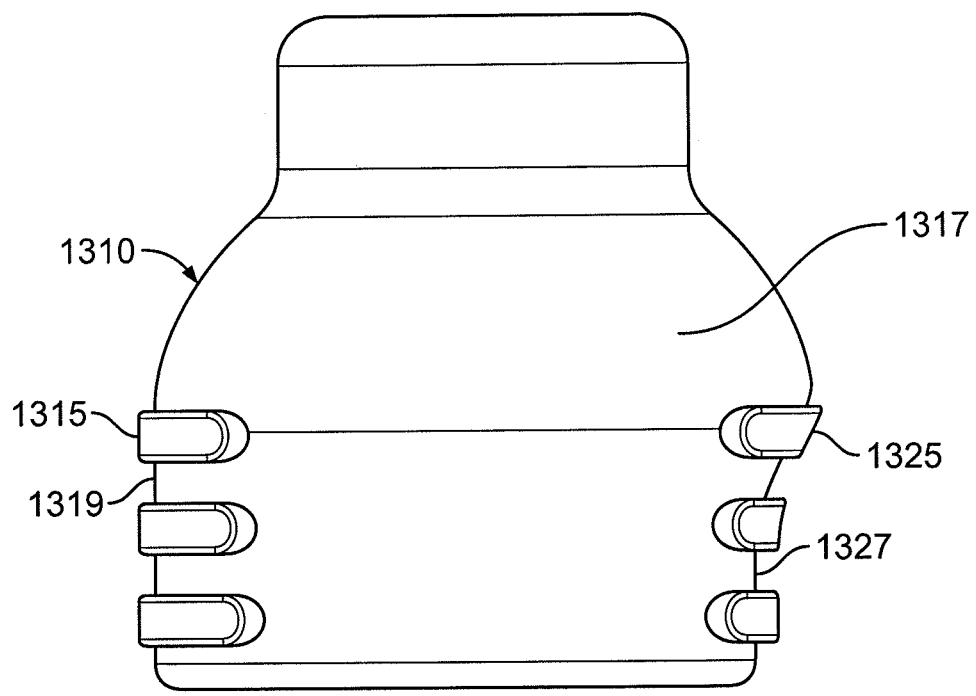
FIG. 13A is a side view showing another embodiment of the antiseptic cap with squeeze grips and two engagement protrusions.
Figure 13B:
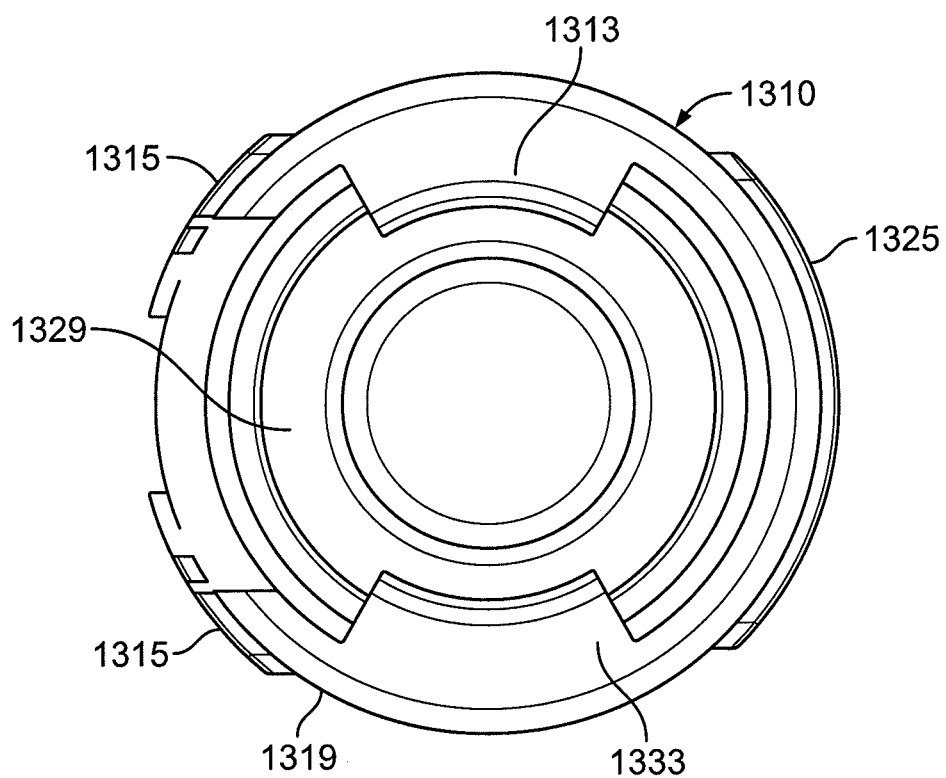
FIG. 13B is a bottom view of the cap of FIG. 13A.
Figure 13C:
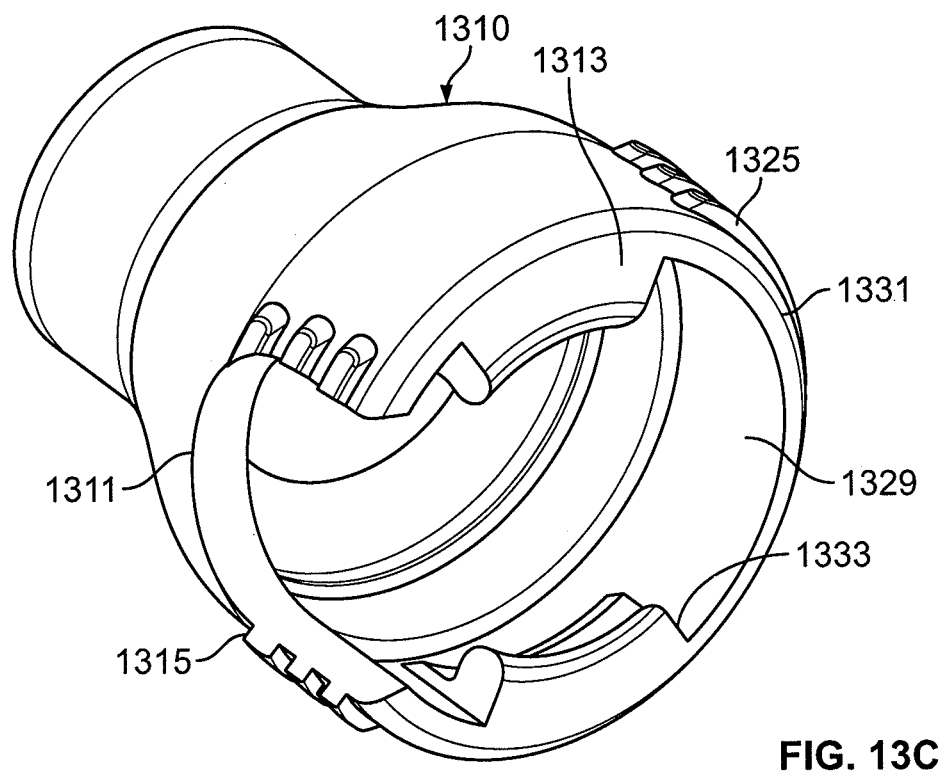
FIG. 13C is a perspective view of the cap of FIG. 13A.

FIGS. 13A-13C show another embodiment of an antiseptic cap, generally indicated as 1310. The cap 1310 includes a sidewall 1317 that has a section 1319 extending toward a bottom surface 1331. The sidewall 1317 includes a plurality of squeeze grips 1315 on a section 1319 and a plurality of squeeze grips 1325 on an opposite section 1327 of the sidewall 1317. The sidewall 1317 defines a chamber 1329.

The antiseptic cap 1310 includes an undercut 1311 (FIG. 13C) defining a channel in the bottom edge 1331. Two diametrically opposed engagement protrusions 1313, 1333 extend from the bottom edge 1331 into the chamber 1329. It will be understood that the number of squeeze grips and engagement protrusions could vary.

When a radial force is applied to the squeeze grips 1315, 1325, the cap 1310 temporarily deforms into a generally oval shape so that the distance between the engagement protrusions 1313, 1333 increases until a user is able to apply, or remove, the cap 1310 from the injection site. Upon application and release of the cap 1310, the distance between the engagement protrusions 1313, 1333 decreases to secure the cap 1310 to the injection site.

Figure 14A:
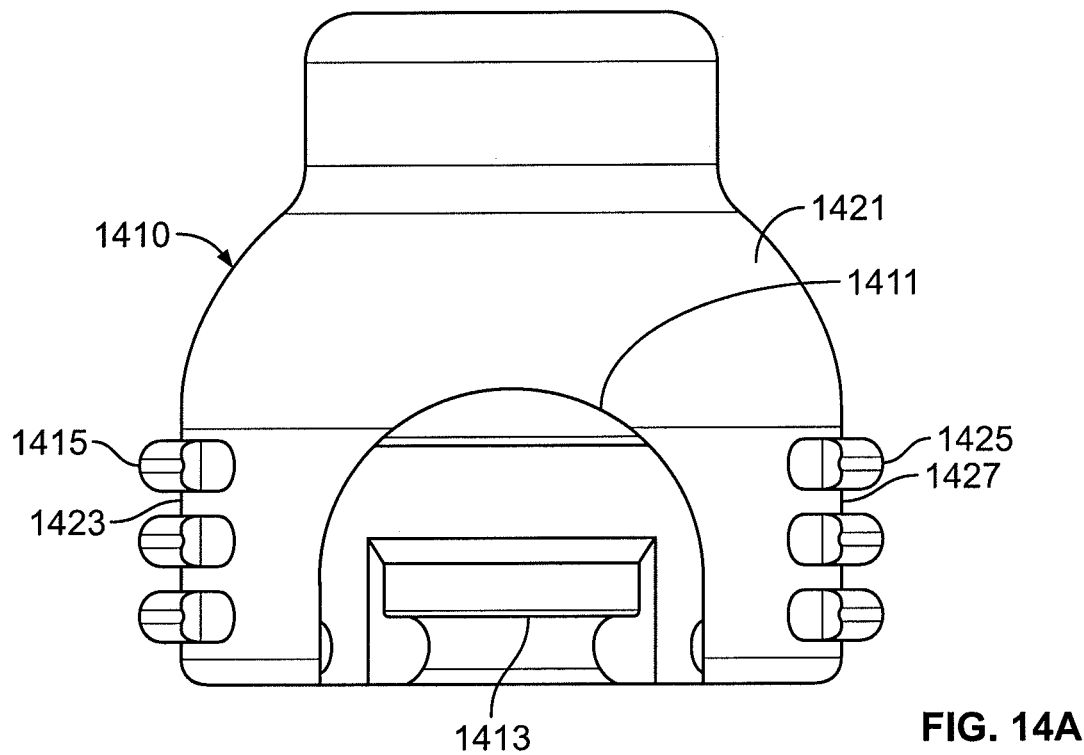
FIG. 14A is a side view showing another embodiment of the antiseptic cap with squeeze grips.
Figure 14B:
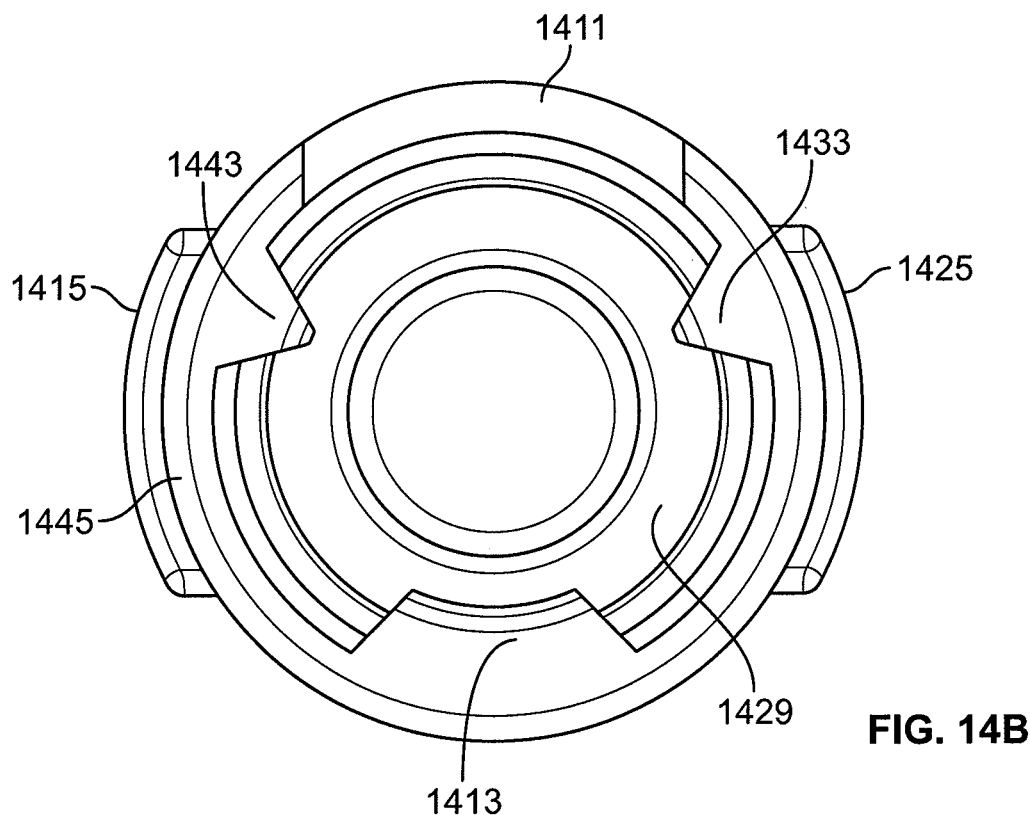
FIG. 14B is a bottom view of the cap of FIG. 14A showing three engagement protrusions.
Figure 14C:
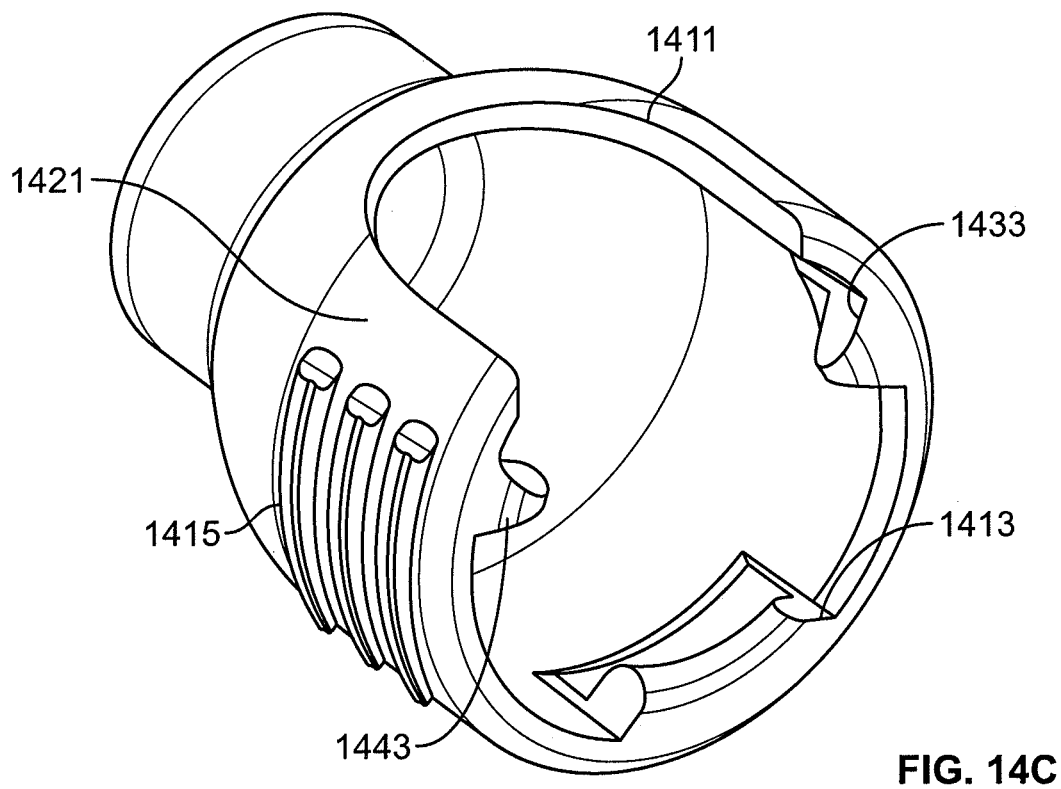
FIG. 14C is a perspective view of the cap of FIG. 14A.

FIGS. 14A-14C show another embodiment of an antiseptic cap, generally indicated as 1410. The cap 1410 includes a sidewall 1421 that has plurality of squeeze grips 1415 on one section 1423 of the sidewall 1421 and a plurality of squeeze grips 1425 on an opposite section 1427 of the sidewall 1421. The sidewall 1421 defines a chamber 1429.

The cap 1410 could include three engagement protrusions 1413, 1433, 1443 that extend from the bottom edge 1445 into the chamber 1429. The protrusions 1413, 1433, 1443 are approximately radially evenly spaced and one of the protrusions 1413 is opposite an undercut 1411 defining a channel formed in the sidewall 1421. While one of the protrusions 1413 has a trapezoidal shape and two of the protrusions 1433, 1443 have a triangular shape, each of the protrusions 1413, 1433, 1443 could be of varying sizes or the same size. When a radial force is applied at each of the squeeze grips 1415, 1425, the resulting deformation of the cap 1410 results in the distance between the engagement protrusions 1413, 1433, 1443 changing sufficiently to allow application or removal of the cap 1410 from an injection site. In one embodiment, one or more of the protrusions 1413, 1433, 1443 are not movable. It will be understood that the number of squeeze grips and engagement protrusions could vary.

Figure 15A:
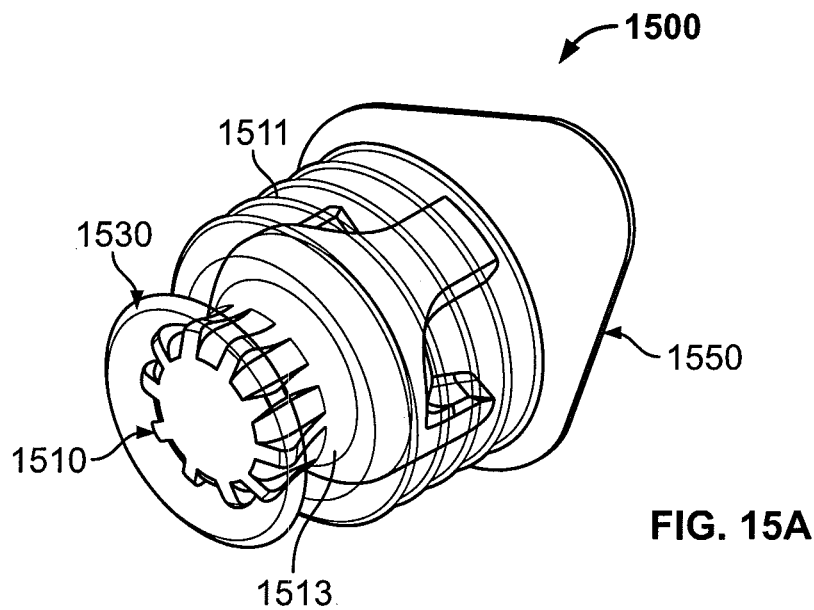
FIG. 15A is a perspective view showing another embodiment of the cap assembly, wherein the cap holder includes bellows.
Figure 15B:
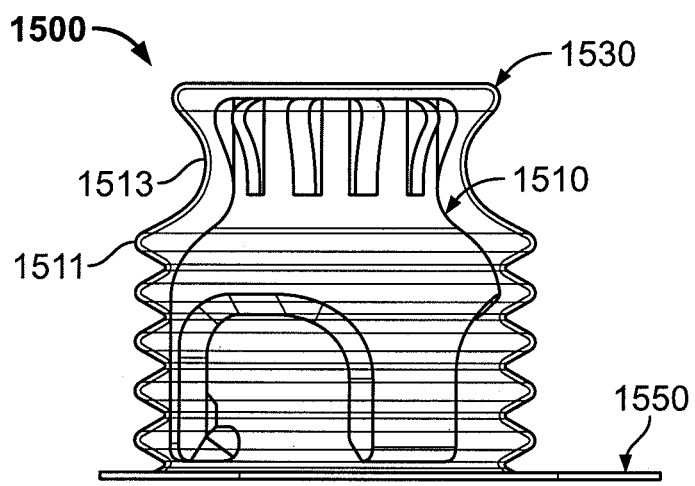
FIG. 15B is a side view of the cap holder and lid of FIG. 15A.
Figure 15C:
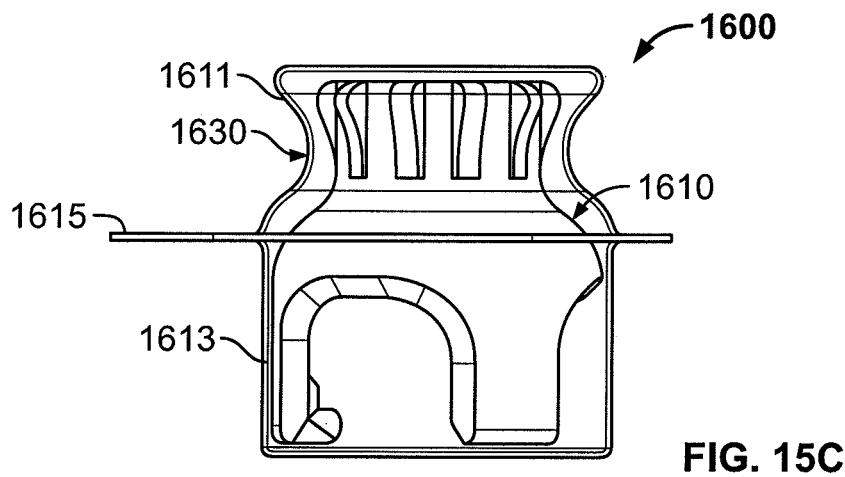
FIG. 15C is side view showing another embodiment of the cap assembly, wherein the cap holder includes a breakable portion.

FIGS. 15A-15C show packaging that could be used in connection with the antiseptic cap 910 (FIGS. 11A-11B), 1010 (FIGS. 11C-11D), 1110 (FIGS. 11E-11F), 1210 (FIGS. 12A-12B), 1310 (FIGS. 13A-13C), and 1410 (FIGS. 14A-14C). It will be understood that the packaging shown in FIGS. 15A-15C could be used in connection with other types of antiseptic caps.

FIGS. 15A-15B show a cap assembly 1500 that includes a cap 1510, a cap holder 1530 and a lid 1550. The cap holder 1530 has a generally accordion shape. In particular, the cap holder 1530 has a bellows section 1511 and a concave-shaped wall 1513 extending from the bellows section 1511. The bellows section 1511 is sized to compress when the antiseptic cap 1510 is applied to an injection site. The cap holder 1530 allows the cap 1510 to be applied aseptically. While the cap holder 1530 could be made from any suitable material, the cap holder 1530 is preferably made from a thermofoam material, a soft material, a flexible material, such as low density polyethylene, a thermoplastic elastomer, silicone, rubber, etc. The cap holder 1530 could be liquid-injected molded, blow-molded, etc. In one embodiment, the cap holder 1530 is transparent.

Alternatively, and as shown in FIG. 15C, the cap assembly 1600 includes a cap 1610 and a breakable cap holder 1630. The cap holder 1630 has a top housing portion 1611, a bottom housing portion 1613 removably and sealably attached to the top housing portion 1611, and a clamp-like handle 1615 separating the top housing portion 1611 and the bottom housing portion 1613. The top housing portion 1611 and the bottom housing portion 1613 cooperate to seal the cap 1610 within the cap holder 1630. Once the bottom housing portion 1613 is removed, the top housing portion 1611 of the cap holder 1630 could be used to aseptically apply the cap 1610 to the injection site.

Figure 16A:
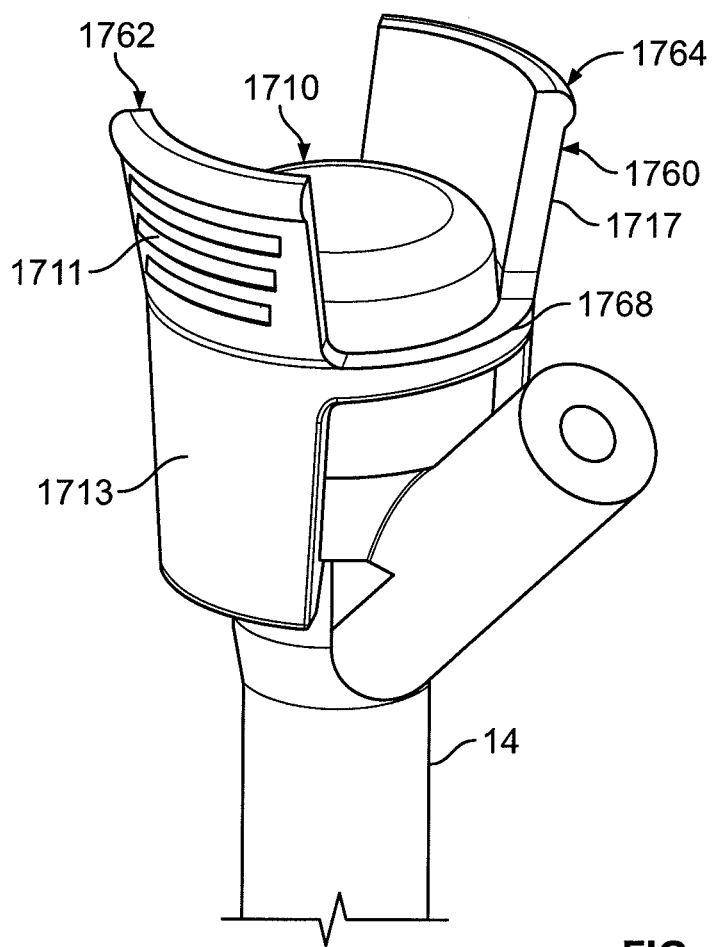
FIG. 16A is a perspective view showing another embodiment of the antiseptic cap with an 'H' clip.
Figure 16B:
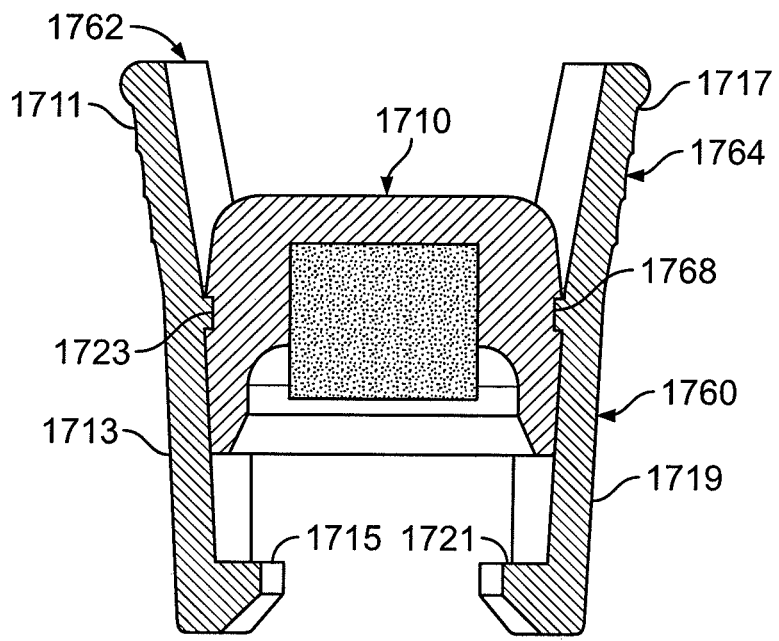
FIG. 16B is a cross-sectional view of the cap of FIG. 16A.

FIGS. 16A-16B show an antiseptic cap 1710 with an 'H' clip 1760 having two pivotable side portions 1762, 1764 and a hinge section 1768 connecting the two side portions 1762, 1764. The side portion 1762 has a top portion 1711 and a bottom portion 1713 with an engagement protrusion 1715, and likewise, the side portion 1764 has a top portion 1717 and a bottom portion 1719 with an engagement protrusion 1721. The bottom portions 1713, 1719 are sized to move apart from each other by pivoting about hinges 1768 when the top portions 1711, 1717 are squeezed against each other. The 'H' clip 1760 could be made from polypropylene and polycarbonate, or any other suitable material. In one embodiment, the 'H' clip 1760 could be made from a harder material than the antiseptic cap. The 'H' clip 1760 could be removable from the cap 1710. The cap 1710 includes an indentation 1723 for securing the hinge section 1768. The hinge section 1768 could be formed from the inherent resilience of the 'H' clip material or it can be formed as a living hinge or otherwise.

To apply or remove the cap 1710, the top portions 1711, 1717 of the side portions 1762, 1764 are squeezed causing the bottom portions 1713, 1719 to pivot about the hinge section 1768. By pivoting about the hinge section 1768, the engagement protrusions 1715, 1721 of the bottom portions 1713, 1719 move away from each other providing sufficient space to remove the cap 1710 from, or apply the cap 1710 to, an injection site 14.

Figure 17A:
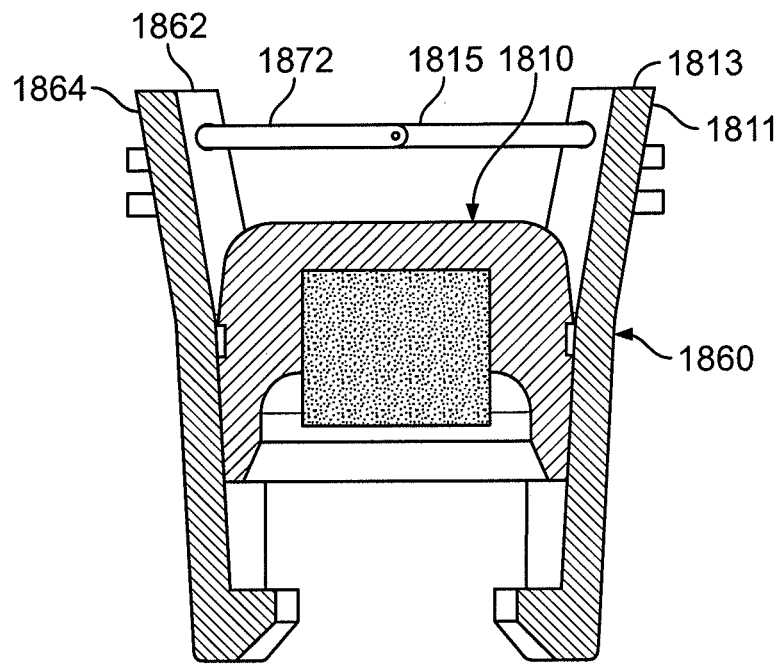
FIG. 17A is a cross-sectional view showing another embodiment of the antiseptic cap with an 'H' clip and connecting segments in a relaxed configuration.
Figure 17B:
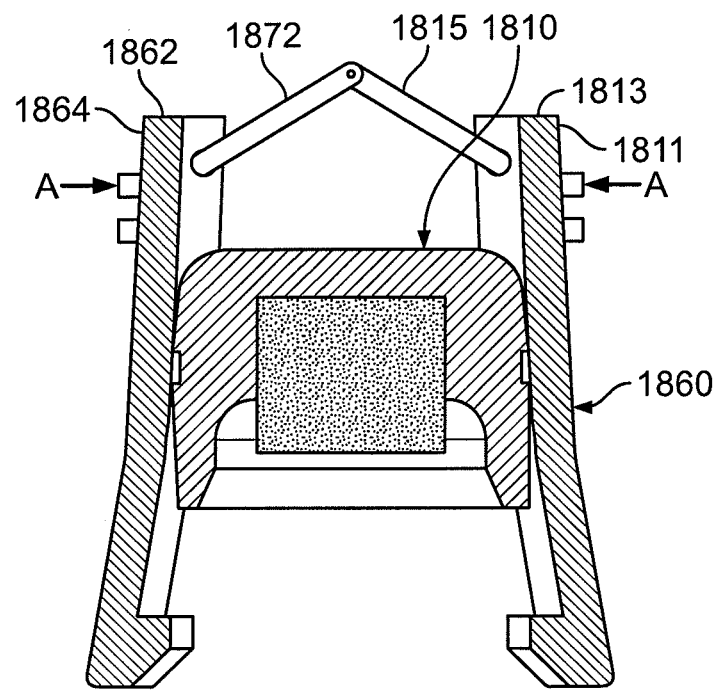
FIG. 17B is a cross-sectional view of the cap with an 'H' clip of FIG. 17A when a force is applied to the 'H' clip in the direction of Arrows A.

FIGS. 17A-17B show another embodiment of an antiseptic cap 1810 with an 'H' clip 1860. The top portion 1864 of the side portion 1862 of the 'H' clip 1860 includes a segment 1872, and the top portion 1811 of the side portion 1813 of the 'H' clip 1860 includes a segment 1815 pivotably connected to the segment 1872. The segments 1815, 1872 are in a linear position when force is not applied to the top portions 1811, 1864. When the top portions 1811, 1864 of the 'H' clip 1860 are squeezed, the two segments 1813, 1862 pivot upwardly, allowing the application or removal of the cap 1810 from an injection site. A user can axially push down on the segments 1815, 1872 to further facilitate application of the cap 1810 to the injection site.

Figure 18:
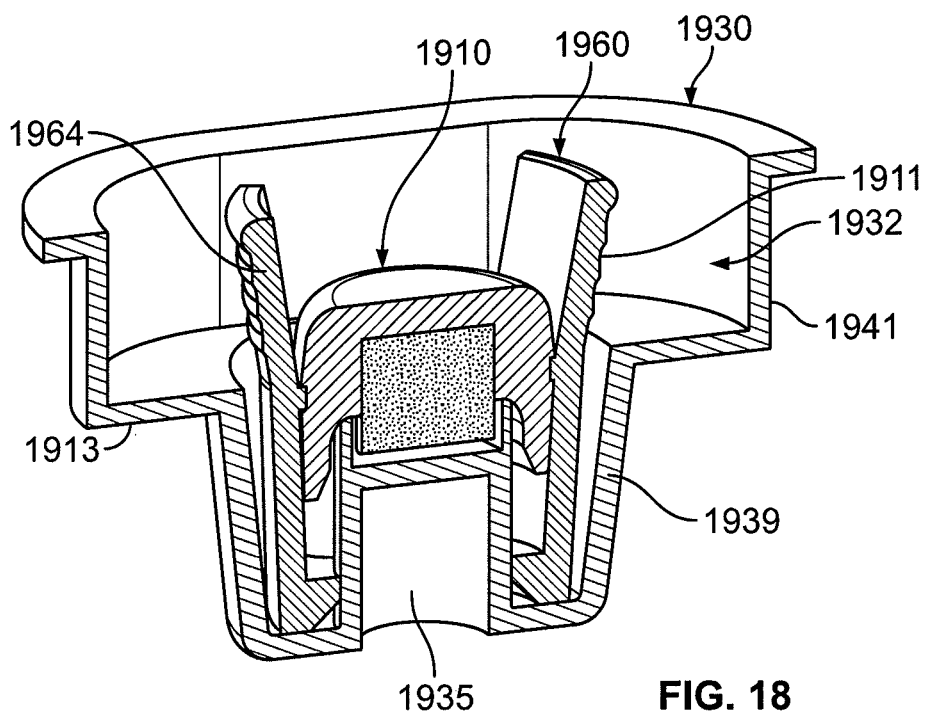
FIG. 18 is a perspective view showing another embodiment of the cap assembly, wherein the cap holder includes an upper cylindrical wall.

There are several options for packaging the cap and the 'H' clip shown in FIGS. 16A-16B and the cap and the 'H' clip shown in FIGS. 17A-17B. An example of packaging is shown in FIG. 18, where the cap holder 1930 comprises a lower cylindrical wall 1939 and an upper cylindrical wall 1941 having a larger diameter than the diameter of the lower cylindrical wall 1939. The cap holder 1930 could include an annular shelf 1913 connecting the lower cylindrical wall 1939 and the upper cylindrical wall 1941, and an axial protrusion 1935, which can retain antiseptic within the antiseptic cap. The increased diameter of the upper cylindrical wall 1941 of the chamber 1932 provides increased access for a user to remove the cap 1910 from the cap holder 1930 by use of the top portions 1911, 1964 of the 'H' clip 1960. In this embodiment, there could a lid or cover.

Figure 19A:
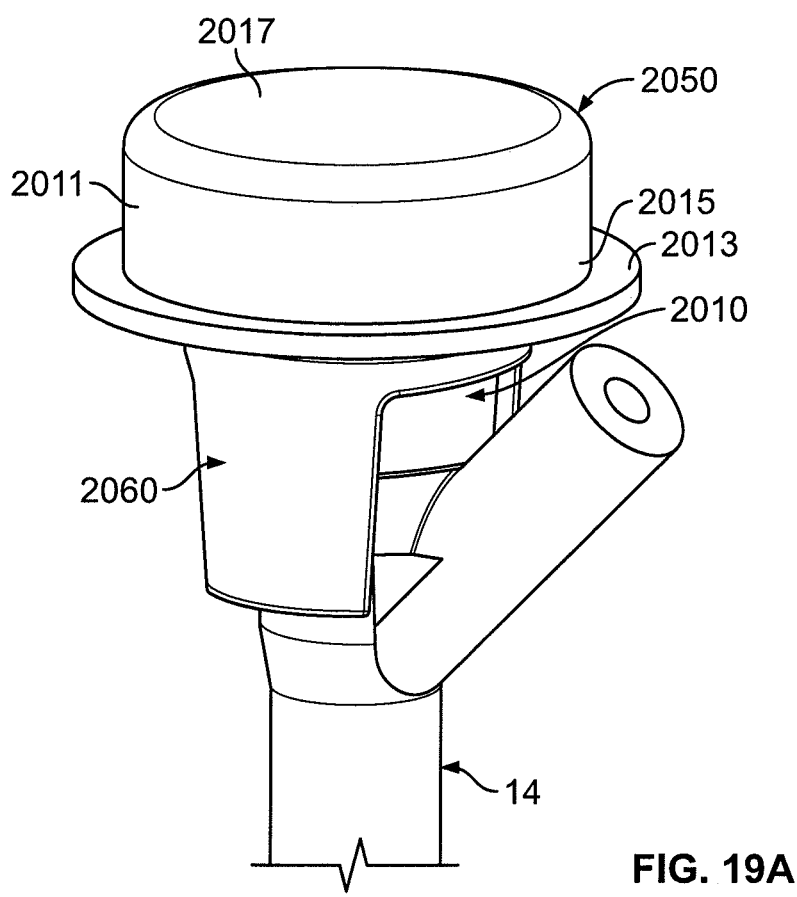
FIG. 19A is a perspective view showing another embodiment of the cap assembly, wherein the cap holder is used as an applicator.

Another example of packaging is shown in FIG. 19A, where the lid 2050 could be used as an applicator. The lid 2050 includes a cylindrical sidewall 2011 defining a chamber. The sidewall 2011 has a flange 2013 protruding from an edge 2015 that defines an open end. The lid 2050 could include a substantially flat surface 2017 that defines an opposite, closed end. The chamber has a depth that receives a portion of the 'H' clip 2060 and the antiseptic cap 2010. As shown in FIG. 19A, a user could push down on the lid 2050, applying force to the 'H' clip 2060 and thereby engage the antiseptic cap 2010 onto an injection site.

Figure 19B:
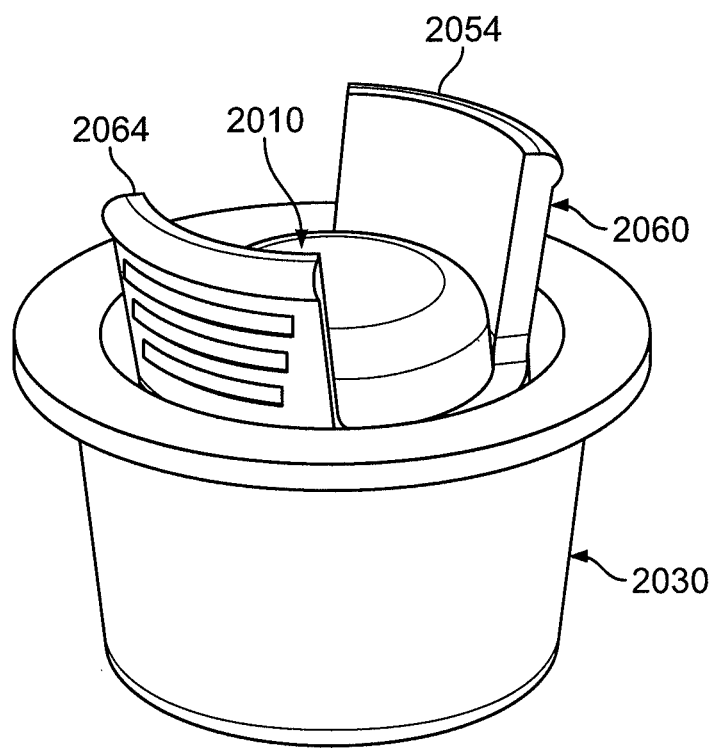
FIG. 19B is a perspective view of a cap with an 'H' clip in a cap holder, where the top portions of the 'H' clip are accessible.
Figure 19C:
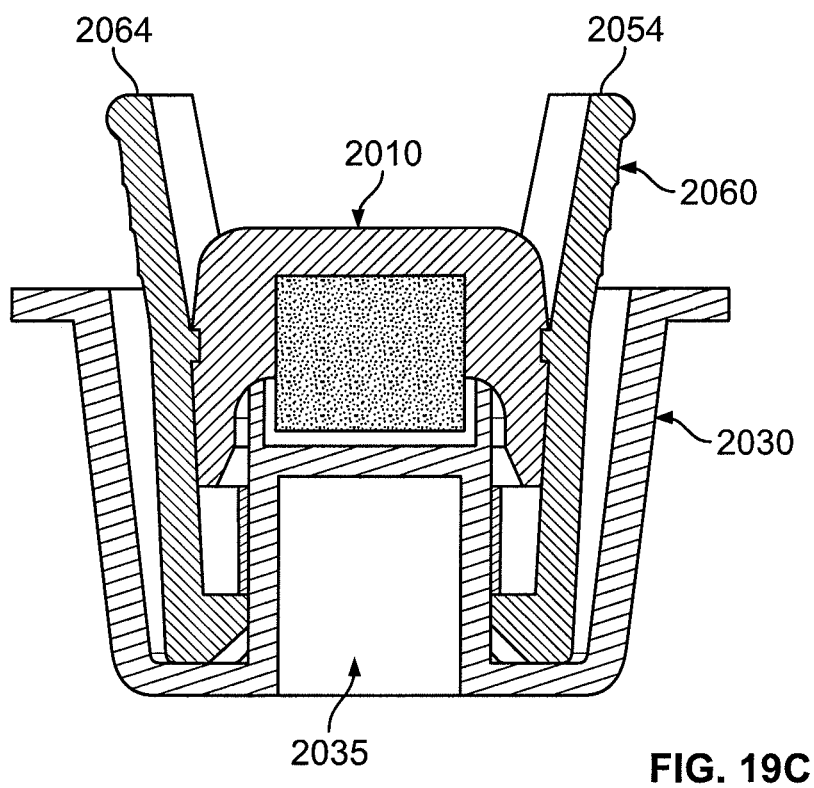
FIG. 19C is a cross-sectional view of the cap and cap holder of FIG. 19B.

Another example of packaging is shown in FIGS. 19B-19C. A user could remove the cap 2010 from the cap holder 2030 by the top portions 2054, 2064 of the 'H' clip 2060. As in previous embodiments, the cap holder 2030 could comprise an axial protrusion 2035.

Figure 20A:
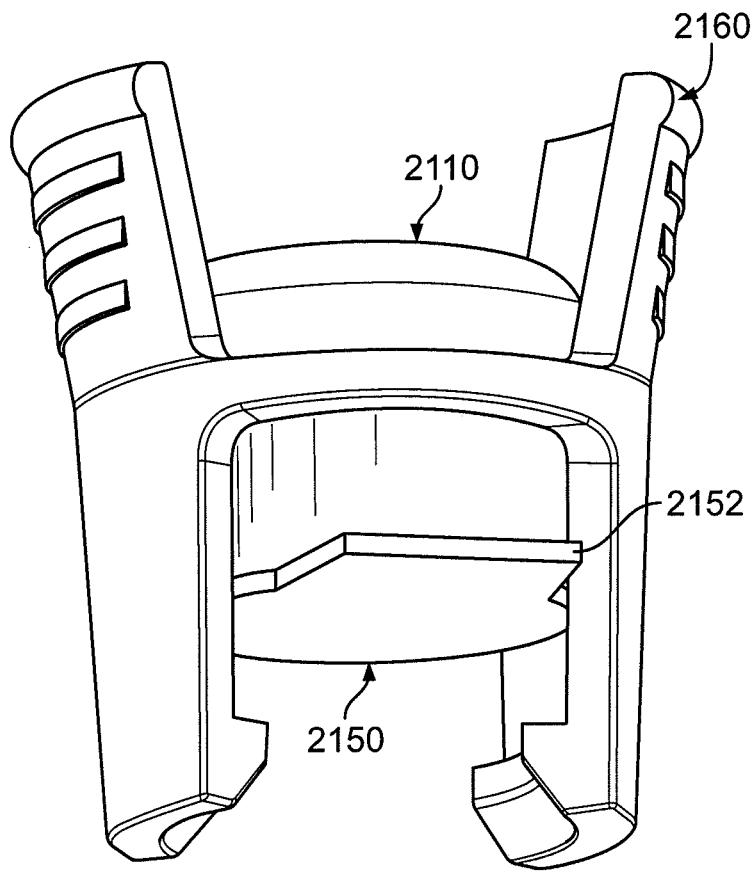
FIG. 20A is a perspective view showing another embodiment of the cap assembly having an 'H' clip and a lid.
Figure 20B:
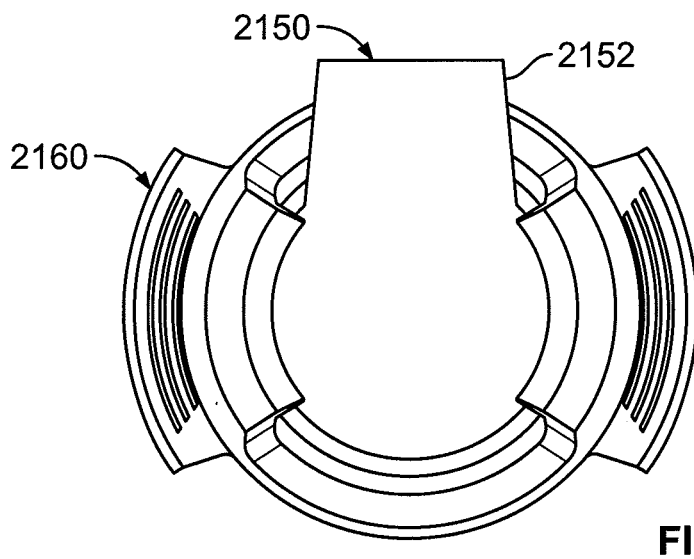
FIG. 20B is a bottom view of a cap and a lid of FIG. 20A.

Another example of packaging is shown in FIGS. 20A-20B, where, instead of a cap holder, the chamber of the cap 2110 with a 'H' clip 2160 is sealed with a blister pack that includes a lid 2150 having a tab 2152 applied directly to the bottom surface of the cap 2110. The blister pack serves to maintain the antiseptic volume over the shelf life. The lid 2150 can be attached in any manner such as by an adhesive, and can be removed by peeling it off of the cap 2110.

Figure 21A:
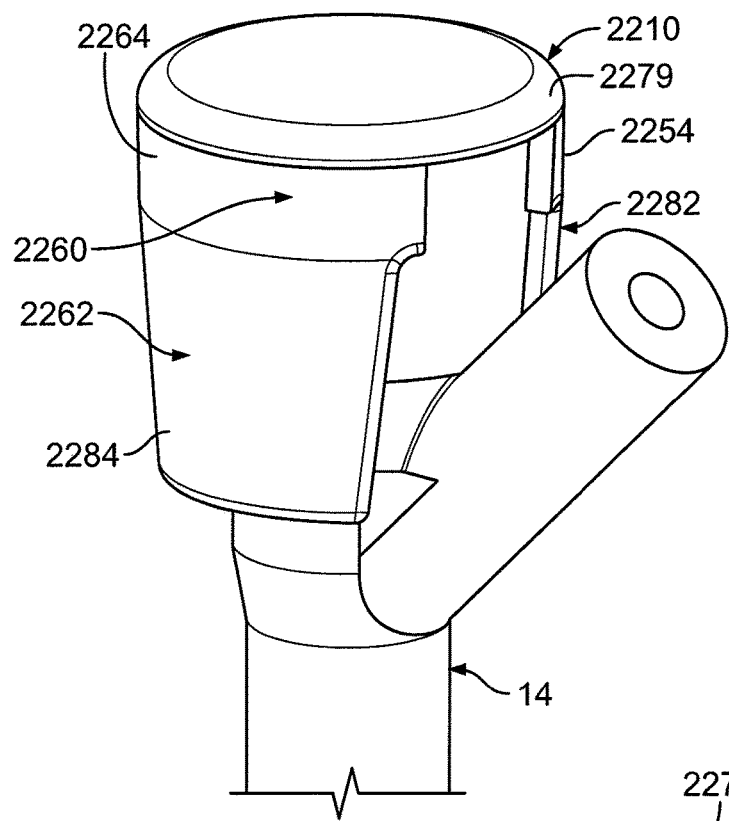
FIG. 21A is a perspective view showing another embodiment of the antiseptic cap having a lower clip configuration.
Figure 21B:
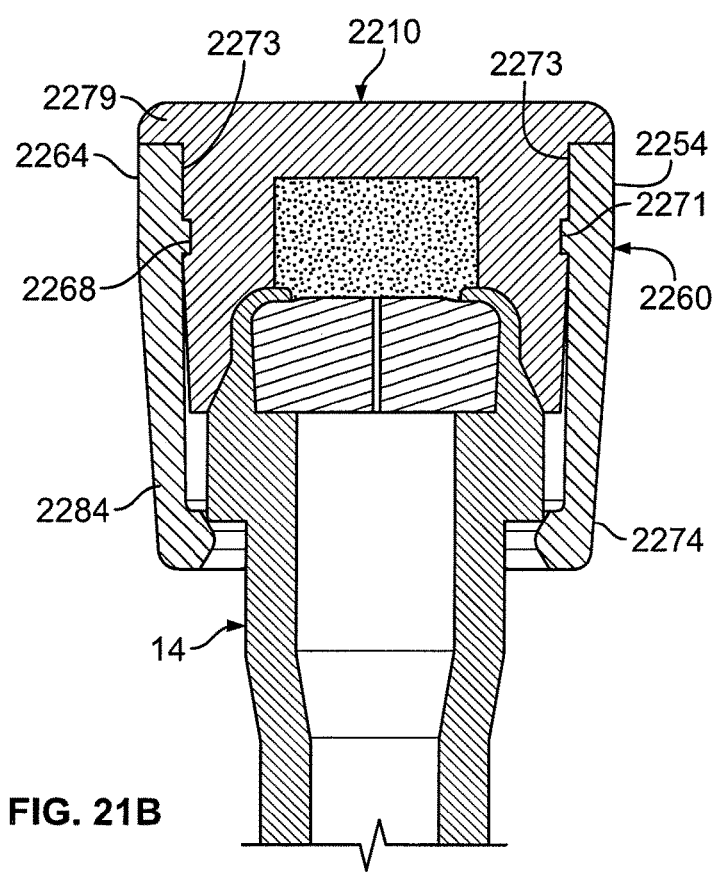
FIG. 21B is a cross-sectional view of the cap and the injection site of FIG. 21A.

Another embodiment of the present invention is shown in FIGS. 21A-21B. Shown is a cap 2210 having a clip 2260 with top portions 2254, 2264 and bottom portions 2274, 2284. The cap 2210 has an indentation 2273 that serves to prevent the clip 2260 from sliding off past the top 2279 of the cap 2210. The clip 2260 has a key 2271 that fits into the indentation 2273 to secure the clip 2260 to the cap 2210.

When the clip 2260 engages the cap, the clip 2260 is positioned such that the top portions 2254, 2264 are below the top 2279 of the cap 2210. When the top portions 2254, 2264 of the cap 2260 are squeezed, the cap 2210 itself is also squeezed and deforms. This temporary deformation allows the side portions 2262, 2282 to pivot around the hinge 2268 so that the cap 2210 can be applied to an injection site 12.

Figure 22A:
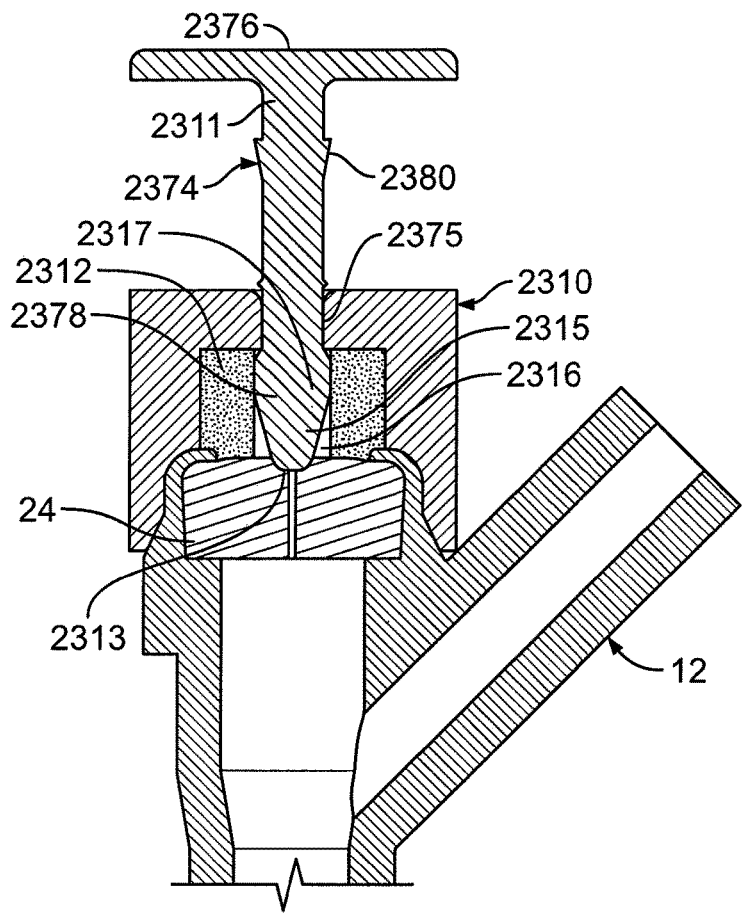
FIG. 22A is a cross-sectional view showing another embodiment of an antiseptic cap with a plunger applied to an injection site.
Figure 22B:
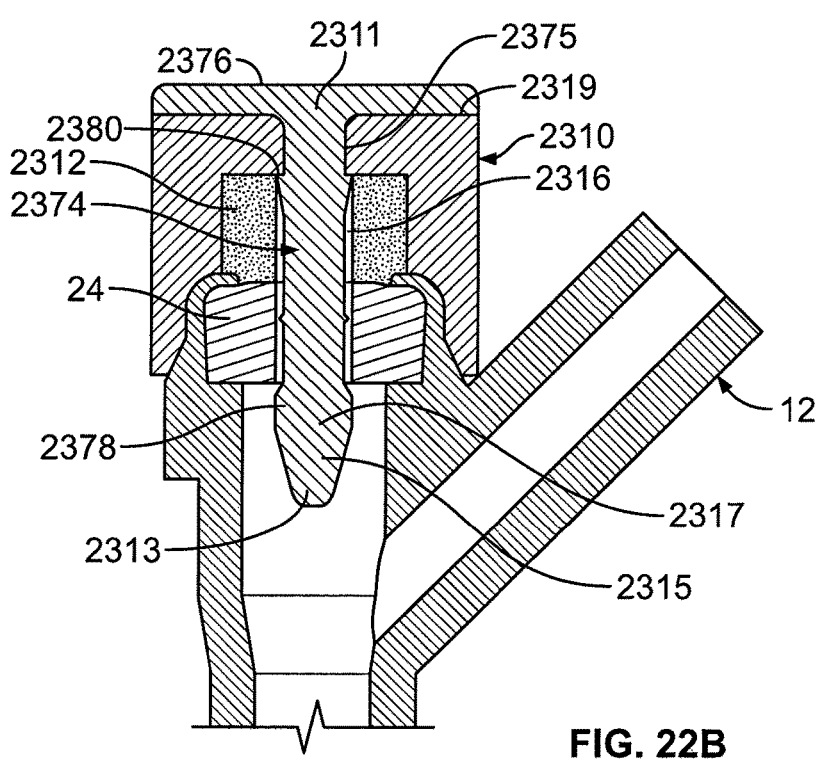
FIG. 22B is a cross-sectional view of the cap of FIG. 22A with the plunger fully engaged with the cap.

FIGS. 22A-22B are cross sectional views of a further embodiment of the present invention. The cap 2310 comprises an aperture 2375, an antiseptic laden material 2312 with a cylindrical hole 2316 located within the cap 2310, and a push pin 2374 in communication with the aperture 2375 and the cylindrical hole 2316. The push pin 2374 includes an enlarged top portion 2376 and an arm 2378 having one end 2311 extending from the enlarged top portion 2376, and a tip 2313 at an opposite end 2315. The arm 2378 has a tapered section 2317 that tapers (becomes smaller) toward the tip 2313. An annular protrusion 2380 is provided on the push pin 2374.

The push pin 2374 is originally provided in a retracted position, where the tip 2313 is positioned within the cylindrical hole 2316. The push pin 2374 can move from the retracted position to an extended position, where the enlarged top portion 2376 is positioned against the substantially flat top surface 2319 of the cap 2310.

When the cap 2310 is applied to an injection site 12, as shown in FIG. 22A, the user pushes down on an enlarged top portion 2376 of the pin 2374. Once the pin 2374 is fully pushed down, as shown in FIG. 22B, the arm 2378 is engaged and inserted through the septum 24, where the tapered section 2317 of the arm 2378 contacts the underside of the septum 24 to secure the cap 2310 to the injection site 12. Once fully engaged, the annular protrusion 2380 on the push pin 2374 locks the cap 2310 on the injection site. It will be understood that the push pin 2374 could be non-movable.

Figures 23A, 23B:
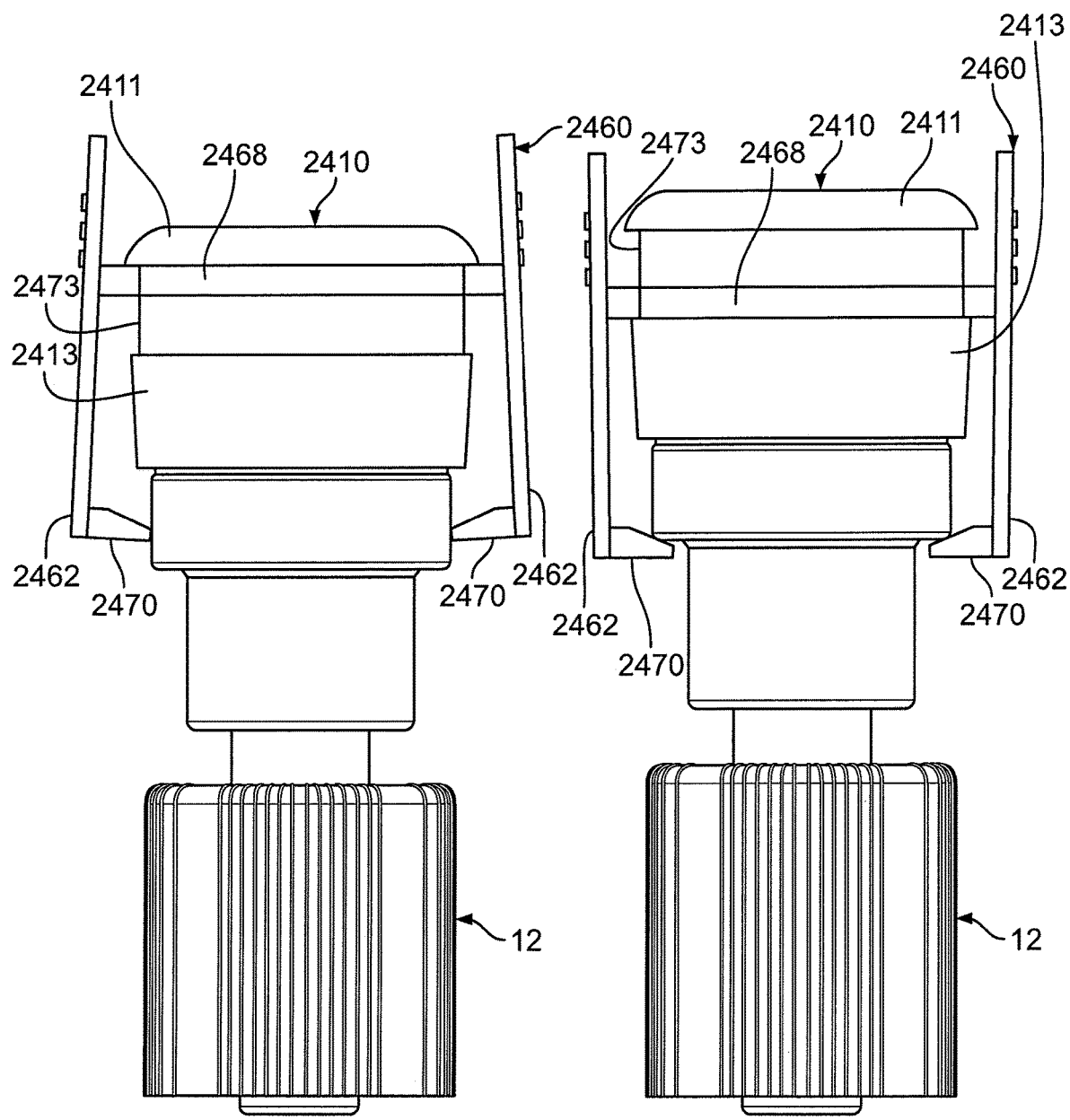
FIG. 23A is a side-view showing another embodiment of the antiseptic cap with a sliding 'H' clip.
FIG. 23B is a side-view of a cap with the sliding 'H' clip cap shown in FIG. 23A fully engaged with an injection site.

Shown in FIGS. 23A-23B is another embodiment of the present invention where the cap 2410 comprises a sliding 'H' clip 2460. The two sides 2462 of the 'H' clip 2460 are connected by a hinged section 2468, where the cap 2410 comprises an upper section 2411, a lower section 2413, an indentation 2473 between the upper section 2411 and the lower section 2413. The indentation 2473 has a diameter less than the diameter of the upper section 2411 and the lower section 2413, and the indentation 2473 is slightly less in diameter than the diameter of the hinged section 2468 of the 'H' clip 2460. The cap 2410 is applied to an injection site 12, as shown in FIG. 23A, with the 'H' clip 2460 at the top of the indentation 2473 of the cap 2410 and the side portions 2462 flared out over the injection site 12. When the 'H' clip 2460 is pushed down on the cap 2410, as shown in FIG. 23B, the 'H' clip 2460 slides down the indentation 2473 of the cap 2410 until the hinge section 2468 is in contact with the lower section 2413. In this position, the engagement protrusions 2470 of the side portions 2462 engage the injection site 12, thereby securing the cap 2410 to the injection site 12. The indentation 2473 prevents the 'H' clip 2460 from sliding off the top or bottom of the cap 2410.

Figures 23C, 23D:
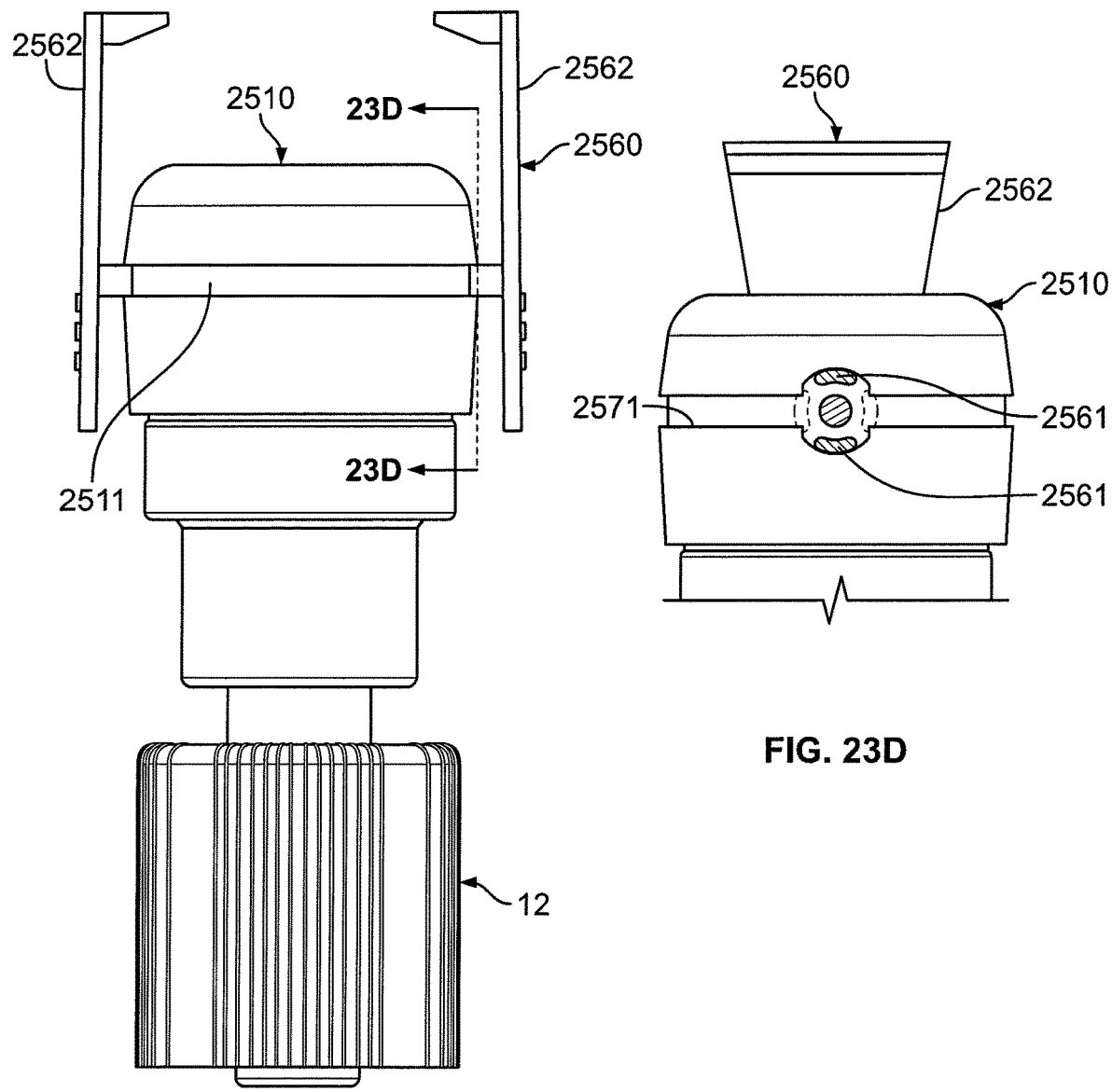
FIG. 23C is a side-view showing another embodiment of the antiseptic cap with a rotating 'H' clip applied to an injection site.
FIG. 23D is a partial cross-sectional view of the 'H' clip of the cap shown in FIG. 23C.

Shown in FIG. 23C is another variation of the previous embodiment, where the side portions 2562 of the cap 2510 rotate in separate parallel planes, instead of bending, to engage the injection site 21. In particular, the side portions 2562 rotate in a direction parallel to each other, in such a manner to rotate completely. FIG. 23D shows a locking mechanism of the 'H' clip 2560 of FIG. 23C. Locking protrusions 2561 in the side portions 2562 could be used in conjunction with the geometry of a groove 2571 in the cap 2510 or the geometry of the hinge section 2511, to lock the side portions 2562, where the side portions 2562 would be pulled out and rotated, such as by 180 degrees, before locking again.

Figure 23E:
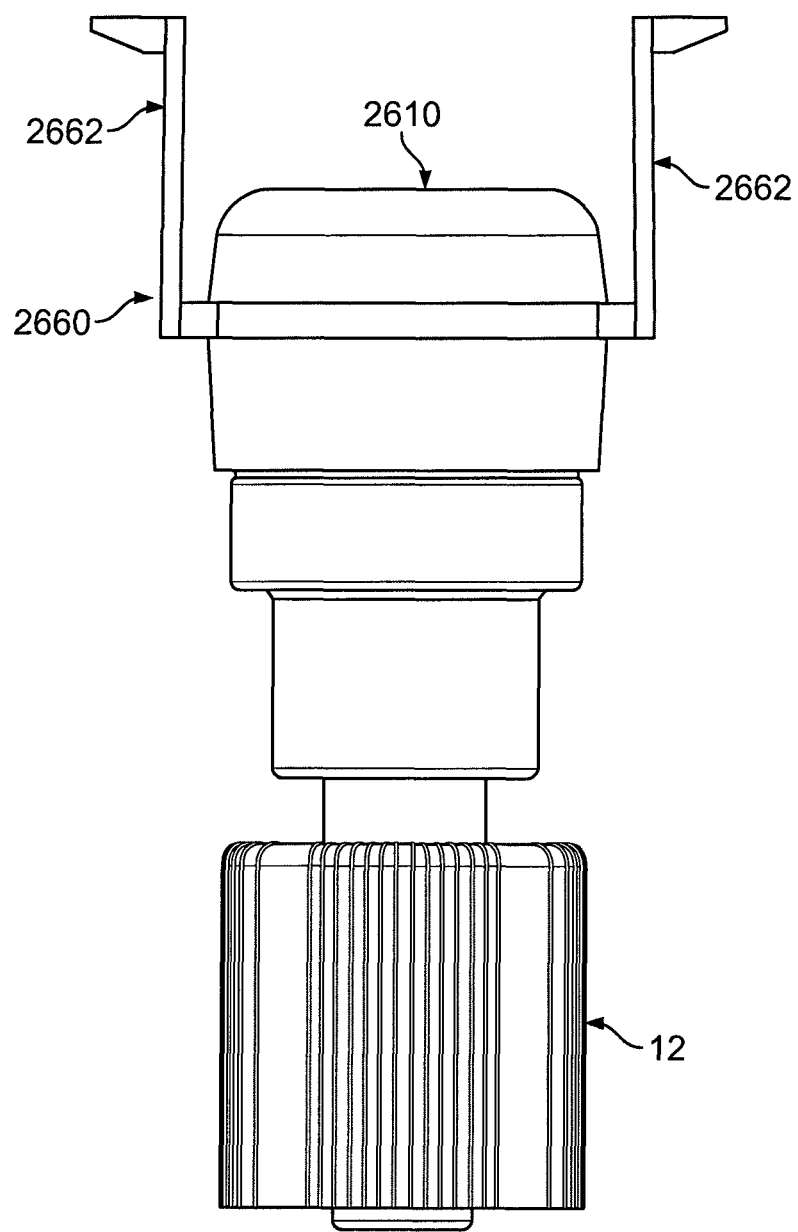
FIG. 23E is a side-view showing another embodiment of the antiseptic cap with a rotating 'H' clip applied to an injection site, where the legs rotate in the same plane.

Shown in FIG. 23E is a further embodiment of the present invention where the side portions 2662 of the 'H' clip 2660 rotate in the same plane to engage and disengage the cap 2610 from the injection site 12. In particular, the side portions 2662 rotate in a manner to only complete a partial rotation.

Figure 24A:
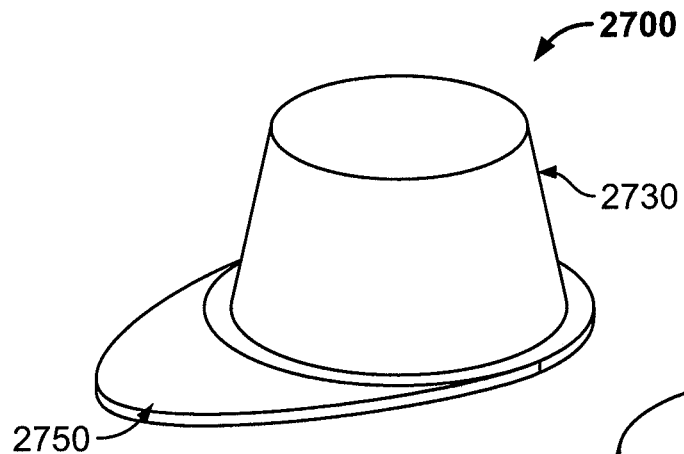
FIGS. 24A-24C are perspective views showing another embodiment of a cap holder with a frangible element.
Figure 24B:
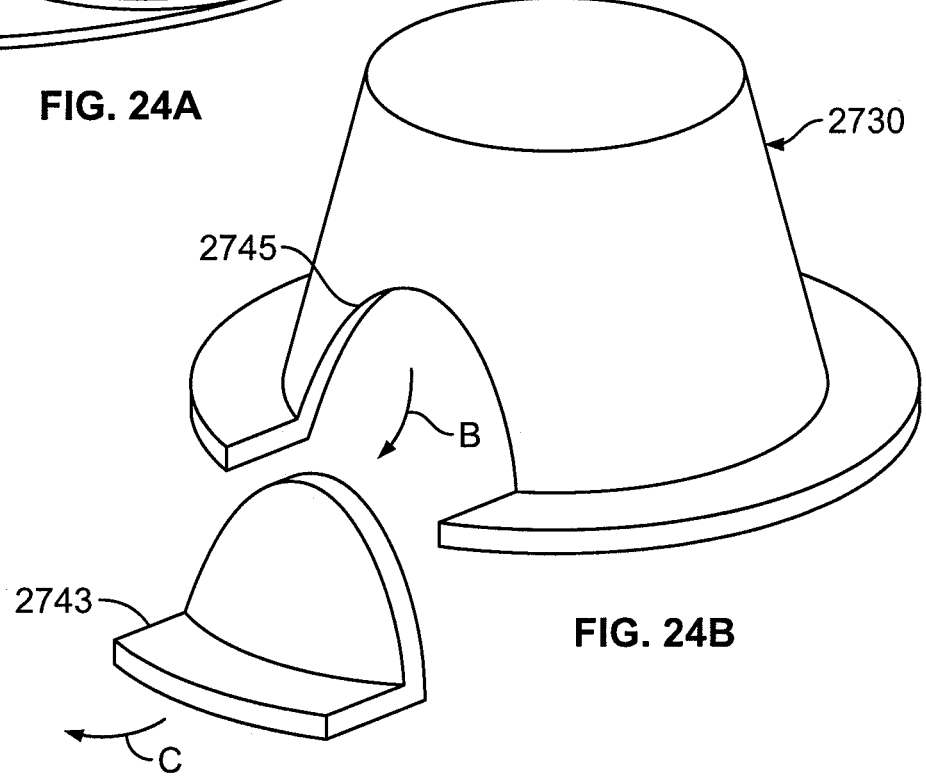
Figure 24C:
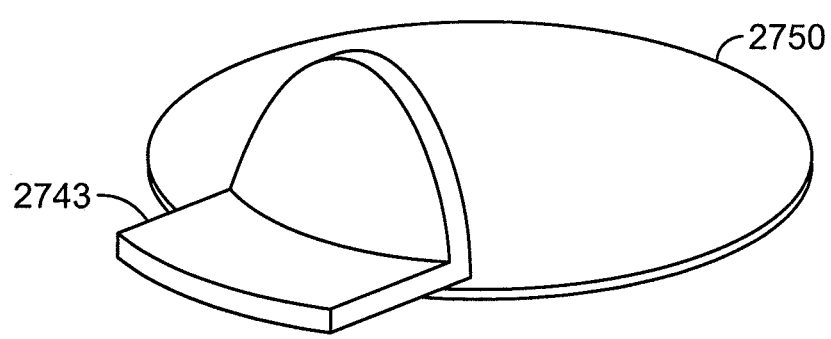

FIGS. 24A-24C is another embodiment of the present invention. The cap assembly 2700 could comprise a lid 2750 and cap holder 2730 having a frangible and removable element 2743. When the frangible element 2743 is removed by shown by arrows B and C, an undercut 2745 of the the cap holder 2730 defines a channel to apply an antiseptic cap to an injection site, including a 'Y' connector injection site or 'T' connector injection site. The frangible element 2743 may be attached to the lid 2750 such that removing the frangible element 2743 removes the lid 2750 as well.

Figure 25:
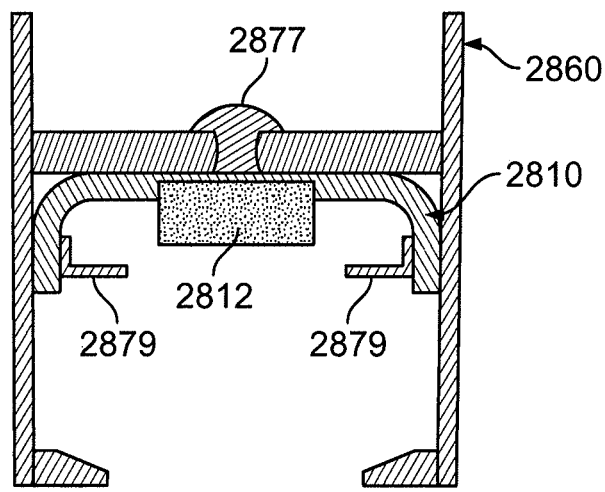
FIG. 25 is a cross-sectional view showing another embodiment of the antiseptic cap with a snap-on 'H' clip.

FIG. 25 is another embodiment showing an 'H' clip 2860 attached to the top of a cap 2810 by a snap-on protrusion 2877, preferably made of plastic. The cap 2810 also comprises an annular seal 2879 to maintain the antiseptic solution of the antiseptic material 2812 on the top of the septum of an injection site when applied to the injection site. The antiseptic cap 2810 could be made from a thermoplastic elastomer, such as the thermoplastic elastomer sold by ExxonMobil under the trademark Santoprene or any other suitable material.

Figure 26:
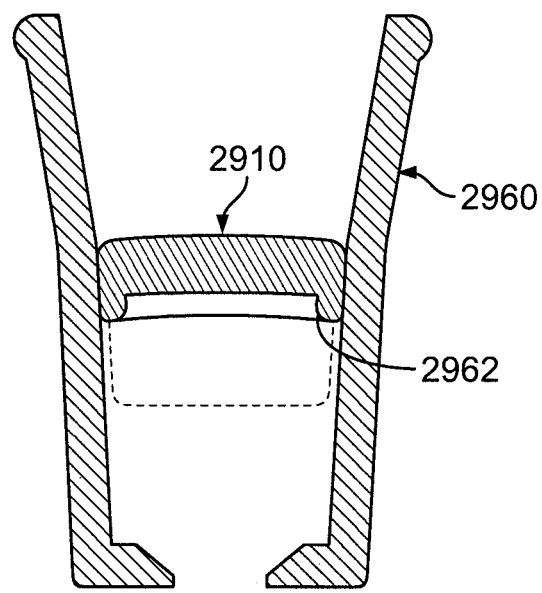
FIG. 26 is cross-sectional view showing another embodiment of the antiseptic cap with a 'H' clip.

FIG. 26 is another embodiment showing an 'H' clip with two legs 2960, a top 2910, and a hinge 2962.

It should be understood that various features of various embodiments disclosed herein could be used together without departing from the spirit or scope of the present invention. It should be understood that while the antiseptic cap is shown in connection with a 'Y' connector injection site 14 in certain embodiments, the antiseptic cap could engage other types of injection sites.

The antiseptic cap assembly could be incorporated in kits with flush syringes, caps for treating a catheter or needleless connector, and line access devices, etc. The antiseptic fluid used could include an anticoagulant material, and/or an antimicrobial material. Examples of antiseptic fluid that could be used are disclosed in U.S. patent application Ser. No. 11/821,190, filed on Jun. 22, 2007, and Ser. No. 12/214,526, filed on Jun. 19, 2008. The entire disclosures of U.S. patent application Ser. Nos. 11/821,190 and 12/214,526 are incorporated herein by reference in their entirety.

It is contemplated that the devices described herein can be coated with an antiseptic coating by any suitable technique such as immersion of the part into an antiseptic solution, by spray coating the part with the antiseptic solution, by blending the antiseptic solution or material into the polymeric material used to fabricate the device.

A quantity of physiological, antimicrobial metal compound is added to the resin for direct molding of an article. Physiological, antimicrobial metals are meant to include the precious metals, such as silver, gold and platinum, and copper and zinc. Physiological, antimicrobial metal compounds used herein include oxides and salts of preferably silver and also gold, for example: silver acetate, silver benzoate, silver carbonate, silver citrate, silver chloride, silver iodide, silver nitrate, silver oxide, silver sulfa diazine, silver sulfate, gold chloride and gold oxide.

Platinum compounds such as chloroplatinic acid or its salts (e.g., sodium and calcium chloroplatinate) may also be used. Also, compounds of copper and zinc may be used, for example: oxides and salts of copper and zinc such as those indicated above for silver. Single physiological, antimicrobial metal compounds or combinations of physiological, antimicrobial metal compounds may be used.

Preferred physiological, antimicrobial metal compounds used in this invention are silver acetate, silver oxide, silver sulfate, gold chloride and a combination of silver oxide and gold chloride. The particles of the silver compounds are sufficiently able to be extracted to form a zone of inhibition to prevent and kill bacteria growth.

In another preferred form of the invention the devices herein are impregnated with triclosan and silver compounds or triclosan and chlorhexidine, or chlorhexidine gluconate, or chlorhexidine acetate.

It will be understood that the embodiments described herein are merely exemplary and that a person skilled in the art may make many variations and modifications without departing from the spirit and scope of the invention. All such variations and modifications are intended to be included within the scope of the invention as defined by the appended claims.

What is claimed is:

1. An antiseptic cap for use with an access site, the antiseptic cap comprising:
   a cap body comprising a sidewall at least partially defining an opening, a permanently closed top wall being located opposite the opening, and a chamber configured to receive an access site such that the closed top wall is configured to serve as a physical barrier into the chamber;
   an antiseptic material contained within the cap body; and
   a clip being engaged with the cap body and having a first position and a second position, the clip being configured to be releasably engaged with at least a portion of the access site when in the second position, the clip being biased towards the second position, the clip comprising:
   a hinge section, and
   at least two side portions,
   wherein the at least two side portions are each configured to move relative to the hinge section as the clip transitions between the first position and the second position.

2. The antiseptic cap of claim 1, wherein each of the at least two side portions comprises:
   a first portion configured to facilitate transition of the clip between the first position and the second position, and
   a second portion configured to be releasably engaged with the access site when the clip is in the second position.

3. The antiseptic cap of claim 2, wherein the second portion of each of the at least two side portions comprises an engagement protrusion.

4. The antiseptic cap of claim 2, wherein the first portion and the second portion of each of the at least two side portions are configured to pivot about the hinge section of the clip when force is applied to the first portion.

5. The antiseptic cap of claim 2, wherein each of the at least two side portions further comprises a pivot segment having an engaged position and a disengaged position, and wherein the antiseptic cap is configured to be removed from the access site when each of the pivot segments are in the disengaged position.

6. The antiseptic cap of claim 1, wherein the cap body comprises an indentation configured to secure the hinge section of the clip.

7. The antiseptic cap of claim 1, wherein the cap body comprises a first material, wherein the clip comprises a second material, and wherein the first material is different from the second material.

8. The antiseptic cap of claim 1, wherein the access site is a luer access device.

9. An antiseptic cap assembly for use with an access site, the antiseptic cap assembly comprising:
the septic cap of claim 1; and
a cap holder comprising:
a cap holder sidewall at least partially defining a cap holder opening and a cap holder chamber configured to receive the antiseptic cap, and
a cover removably attached to the cap holder sidewall.

10. The antiseptic cap of claim 9, wherein each of the at least two side portions comprises:
a first portion configured to facilitate transition of the clip between the first position and the second position, and
a second portion configured to be releasably engaged with the access site when the clip is in the second position.

11. The antiseptic cap of claim 10, wherein the second portion of each of the at least two side portions comprises an engagement protrusion.

12. The antiseptic cap of claim 10, wherein the first portion and the second portion of each of the at least two side portions are configured to pivot about the hinge section of the clip when a squeezing force is applied to the first portion.

13. The antiseptic cap of claim 10, wherein each of the at least two side portions further comprises a pivot segment having an engaged position and a disengaged position, and wherein the antiseptic cap is configured to be removed from the access site when each of the pivot segments are in the disengaged position.

14. The antiseptic cap of claim 9, wherein the cap body comprises an indentation configured to secure the hinge section of the clip.

15. The antiseptic cap of claim 9, wherein the cap body comprises a first material, wherein the clip comprises a second material, and wherein the first material is different from the second material.

16. The antiseptic cap of claim 9, wherein the access site is a luer access device.

* * * * *

UNITED STATES PATENT AND TRADEMARK OFFICE
CERTIFICATE OF CORRECTION

Page 1 of 1

PATENT NO. : 10,695,550 B2
APPLICATION NO. : 16/016960
DATED : June 30, 2020
INVENTOR(S) : Christopher E. Gardner et al.

It is certified that error appears in the above-identified patent and that said Letters Patent is hereby corrected as shown below:

On the Title Page

On page 6, Column 2, item (56), Other Publications, Line 28, delete "redacted" and insert --copy of redacted--.

On page 6, Column 2, item (56), Other Publications, Line 30, delete "redacted" and insert --copy of redacted--.

In the Specification

Column 6, Line 35, delete "otherwise" and insert --otherwise.--.

In the Claims

Column 17, Line 3, Claim 9, delete "septic" and insert --antiseptic--.

Signed and Sealed this
Twenty-second Day of December, 2020

Andrei Iancu
*Director of the United States Patent and Trademark Office*